(12) United States Patent
Ran et al.

(10) Patent No.: US 12,102,695 B2
(45) Date of Patent: Oct. 1, 2024

(54) HALF-CURCUMINOIDS AS AMYLOID-BETA PET IMAGING AGENTS

(71) Applicant: The General Hospital Corporation, Boston, MA (US)

(72) Inventors: Chongzhao Ran, Winchester, MA (US); Anna Moore, Stoneham, MA (US); Jian Yang, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 167 days.

(21) Appl. No.: 17/480,924

(22) Filed: Sep. 21, 2021

(65) Prior Publication Data

US 2022/0001036 A1 Jan. 6, 2022

Related U.S. Application Data

(62) Division of application No. 16/314,153, filed as application No. PCT/US2017/039885 on Jun. 29, 2017, now Pat. No. 11,135,318.

(60) Provisional application No. 62/451,433, filed on Jan. 27, 2017, provisional application No. 62/356,116, filed on Jun. 29, 2016.

(51) Int. Cl.
| | |
|---|---|
| *A61K 51/04* | (2006.01) |
| *A61P 25/28* | (2006.01) |
| *C07B 59/00* | (2006.01) |
| *C07C 49/248* | (2006.01) |
| *C07C 49/252* | (2006.01) |
| *C07F 5/02* | (2006.01) |
| *A61P 25/16* | (2006.01) |

(52) U.S. Cl.
CPC .......... *A61K 51/0453* (2013.01); *A61K 51/04* (2013.01); *A61K 51/0455* (2013.01); *C07B 59/002* (2013.01); *C07C 49/248* (2013.01); *C07C 49/252* (2013.01); *C07F 5/02* (2013.01); *A61K 2123/00* (2013.01); *A61P 25/16* (2018.01); *A61P 25/28* (2018.01); *C07B 2200/05* (2013.01); *C07F 5/022* (2013.01)

(58) Field of Classification Search
CPC ....... A61K 49/00; A61K 51/04; C07D 401/06
See application file for complete search history.

(56) References Cited

U.S. PATENT DOCUMENTS

| | | |
|---|---|---|
| 6,790,979 B2 | 9/2004 | Lee et al. |
| 7,507,864 B2 | 3/2009 | Miller et al. |
| 7,589,123 B2 | 9/2009 | Rees et al. |
| 8,841,326 B2 | 9/2014 | Vander Jagt |
| 2011/0208064 A1* | 8/2011 | Chongzhao ............ A61B 6/037 |
| | | 546/264 |
| 2012/0040976 A1 | 2/2012 | Cashman et al. |
| 2012/0122913 A1 | 5/2012 | Charbonneau et al. |
| 2012/0183474 A1* | 7/2012 | Ran ..................... C07D 213/02 |
| | | 422/69 |
| 2015/0158841 A1* | 6/2015 | Ran ..................... C07D 213/89 |
| | | 514/397 |
| 2016/0193363 A1 | 7/2016 | Ran et al. |

FOREIGN PATENT DOCUMENTS

WO WO 2010/132815 11/2010

OTHER PUBLICATIONS

Bateman et al., "Clinical and biomarker changes in dominantly inherited Alzheimer's disease," The New England Journal of Medicine, 2012, 367:795-804.
Brier et al., "Tau and abeta imaging, csf measures, and cognition in Alzheimer's disease," Sci Transl Med, 2016, 8:338ra366.
Brookmeyer et al., "Forecasting the global burden of Alzheimer's disease," Alzheimer's and Dementia, 2007, 3 186-191.
Cao et al., "Intake of Sucrose-sweetened Water Induces Insulin Resistance and Exacerbates Memory Deficits and Amyloidosis in a Transgenic Mouse Model of Alzheimer Disease," The Journal of Biological Chemistry, 2007, 282:36275-36282.
Chiotis et al., "Imaging in-vivo tau pathology in Alzheimer's disease with thk5317 pet in a multimodal paradigm," European Journal of Nuclear Medicine and Molecular Imaging, 2016, 43:1686-1699.
Ganguli et al., "Apolipoprotein e polymorphism and Alzheimer disease: The indo-us cross-national dementia study," Archives of Neurology, 2000, 57:824-830.
Goedert and Spillantini, "A century of Alzheimer's disease," Science, 2006, 314:777-781.
Gomperts et al., "Reply: Beyond the limits of detection: Failure of pib imaging to capture true abeta burden," Mov Disord, 2013, 28:407.
Hardy and Selkoe, "The Amyloid Hypothesis of Alzheimer's Disease: Progress and Problems on the Road to Therapeutics," Science, 2002, 297:353-356.
Hsiao et al, "Correlative memory deficits, Aβ elevation, and amyloid plaques in transgenic mice," Science, 1996, 274:99-102.
Ikonomovic et al., "Post-mortem correlates of in vivo pib-pet amyloid imaging in a typical case of Alzheimer's disease," Brain : a Journal of Neurology, 2008, 131:1630-1645.
International Preliminary Report on Patentability in International Application No. PCT/US2017/039885, dated Jan. 1, 2019, 7 pages.
International Search Report and Written Opinion in International Application No. PCT/US2017/039885, dated Nov. 6, 2017, 17 pages.
Johnson et al., "Tau positron emission tomographic imaging in aging and early Alzheimer disease," Annals of Neurology, 2016, 79:110-119.

(Continued)

*Primary Examiner* — Michael G. Hartley
*Assistant Examiner* — Jagadishwar R Samala
(74) *Attorney, Agent, or Firm* — Fish & Richardson P.C.

(57) ABSTRACT

Provided herein are curcumin analogues that are able to interact with amyloid beta (Aβ) and to attenuate the copper-induced crosslinking of Aβ. Also provided herein are methods of using the compounds as imaging agents of amyloid beta and for the treatment of diseases associated with amyloid beta. Methods of preparing unlabeled and radiolabeled compounds useful for interacting with amyloid beta and pharmaceutical compositions are also provided.

20 Claims, 7 Drawing Sheets

(56) References Cited

OTHER PUBLICATIONS

Kalaitzakis and Pearce, "Beyond the limits of detection: Failure of pib imaging to capture true Aβ burden," Mov Disord, 2013, 28:406.
Kantarci et al., "Antemortem amyloid imaging and beta-amyloid pathology in a case with dementia with lewy bodies," Neurobiology of Aging, 2012, 33:878-885.
Klafki et al., "Therapeutic approaches to Alzheimer's disease," Brain, 2006, 129:2840-2855.
Kuntner et al., "Limitations of small animal pet imaging with [18f]fddnp and fdg for quantitative studies in a transgenic mouse model of Alzheimer's disease," Molecular Imaging and Biology, 2009, 11:236-240.
Lue et al, "Soluble Amyloid β Peptide Concentration as a Predictor of Synaptic Change in Alzheimer's Disease," Am. J. Pathol. 1999, 155:853-862.
Maeda et al., "Longitudinal, quantitative assessment of amyloid, neuroinflammation, and anti-amyloid treatment in a living mouse model of Alzheimer's disease enabled by positron emission tomography," The Journal of Neuroscience, 2007, 27:10957-10968.
Mathis et al., "Development of positron emission tomography beta-amyloid plaque imaging agents," Semin Nucl Med, 2012, 42:423-432.
Mawuenyega et al, "Decreased Clearance of CNS Amyloid-β in Alzheimer's Disease," Science, 2011, 330:1774-1776.
McLean et al, "Soluble pool of Aβ amyloid as a determinant of severity of neurodegeneration in Alzheimer's disease," Ann. Neurol. 1999, 46:860-866.
Melnikova, "Therapies for Alzheimer's disease," Nature Rev Drug Discov, 2007, 6:341-342.
Mori et al., "Molecular imaging of dementia," Psychogeriatrics, 2012, 12:106-114.
Ossenkoppele et al., "Tau pet patterns mirror clinical and neuroanatomical variability in Alzheimer's disease," Brain : a Journal of Neurology, 2016, 139:1551-1567.
Patel et al., "18f-fluoropropyl curcumin: A potential pet tracer for imaging inflammation and aβ-plaques," J. Nucl. Med, 2007, 48:22p-22p.
pubchem.ncbi.nlm.nih.gov [online]. "Substance Record for SID 163719244," dated Aug. 5, 2013 [retrieved on Aug. 9, 2017]. Retrieved from the Internet: URL: https://pubchem.ncbi.nlm.nih.gov/substance/163719244>. 5 pages.
Ran et al., "Design, synthesis, and testing of difluoroboron-derivatized curcumins as near-infrared probes for in vivo detection of amyloid-beta deposits," J Am Chem Soc, 2009, 131:15257-15261.
Rokka et al., "Synthesis and evaluation of a (18)f-curcumin derivate for beta-amyloid plaque imaging," Bioorganic & Medicinal Chemistry, 2014, 22:2753-2762.
Ryu et al., "Curcumin and dehydrozingerone derivatives: Synthesis, radiolabeling, and evaluation for beta-amyloid plaque imaging," Journal of Medicinal Chemistry, 2006, 49:6111-6119.
Scholl et al., "Pet imaging of tau deposition in the aging human brain," Neuron, 2016, 89:971-982.
Selkoe et al, "Translating cell biology into therapeutic advances in Alzheimer's disease," Nature, 1999, 399:A23-31.
Selkoe, "Resolving controversies on the path to Alzheimer's therapeutics," Nature Medicine, 2011, 17:1060-1065.
Sepulcre et al., "In vivo tau, amyloid, and gray matter profiles in the aging brain," The Journal of Neuroscience, 2016, 36:7364-7374.
Shah and Catafau, "Molecular imaging insights into neurodegeneration: Focus on tau pet radiotracers," Journal of Nuclear Medicine, 2014, 55:871-874.
Snellman et al., "Longitudinal amyloid imaging in mouse brain with 11c-pib: Comparison of app23, tg2576, and appswe-ps1de9 mouse models of Alzheimer disease," Journal of Nuclear Medicine, 2013, 54:1434-1441.
Sperling et al., "Preclinical Alzheimer disease-the challenges ahead," Nature Reviews, 2012, 9:54-58.
Spires-Jones and Hyman, "The intersection of amyloid beta and tau at synapses in Alzheimer's disease," Neuron, 2014, 82:756-771.
Stancu et al., "Tauopathy contributes to synaptic and cognitive deficits in a murine model for Alzheimer's disease," FASEB Journal, 2014, 28:2620-2631.
Terry et al., "Physical basis of cognitive alterations in Alzheimer's disease: Synapse loss is the major correlate of cognitive impairment," Ann. Neurol, 1991, 30:572-580.
Thapa et al., "Curcumin attenuates amyloid-beta aggregate toxicity and modulates amyloid-beta aggregation pathway," ACS Chem Neurosci, 2016, 7:56-68.
Wang et al., "Evaluation of tau imaging in staging Alzheimer disease and revealing interactions between beta-amyloid and tauopathy," JAMA Neurol, 2016, 73:1070-1077.
Zhang et al., "A bifunctional curcumin analogue for two-photon imaging and inhibiting crosslinking of amyloid beta in Alzheimer's disease," Chemical Communications, 2014, 50:11550-11553.
Zhang et al., "Current neuroimaging techniques in Alzheimer's disease and applications in animal models," Am J Nucl Med Mol Imaging, 2012, 2:386-404.
Zhang et al., "Design and synthesis of curcumin analogues for in vivo fluorescence imaging and inhibiting copper-induced cross-linking of amyloid beta species in Alzheimer's disease," Journal of the American Chemical Society, 2013, 135:16397-16409.
Zhang et al., "Near-infrared fluorescence molecular imaging of amyloid beta species and monitoring therapy in animal models of Alzheimer's disease," PNAS, 2015, 112:9734-9739.
Zhao et al., "The toxicity of amyloid beta oligomers," Int J Mol Sci, 2012, 13:7303-7327.

* cited by examiner

FIGs. 3C-3D

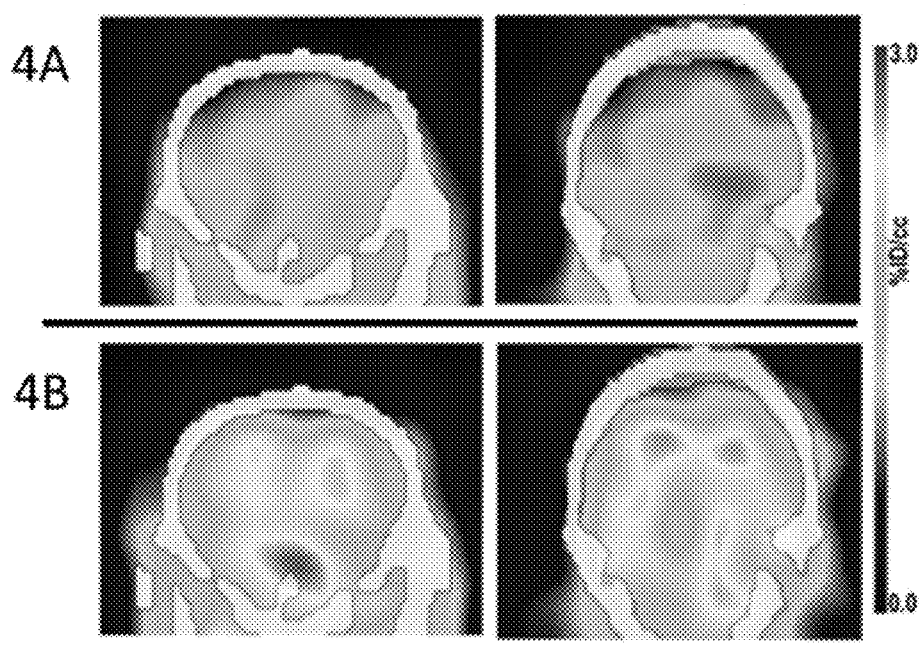
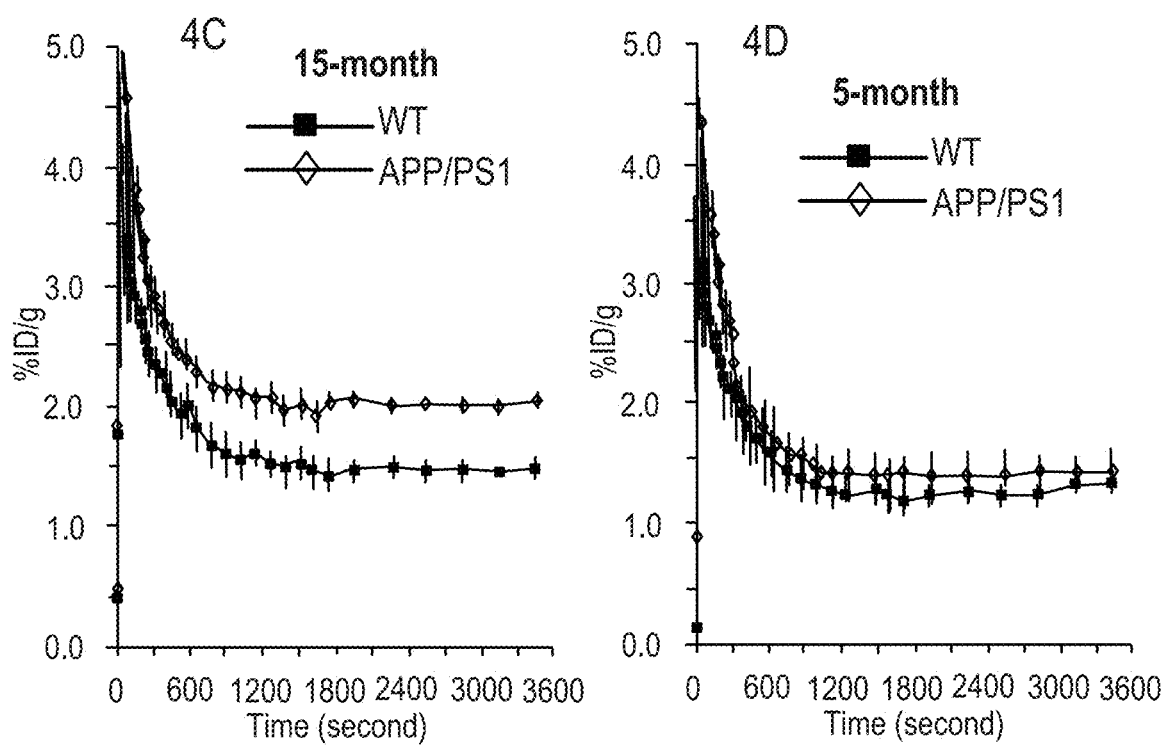
FIGs. 4A-4D

HALF-CURCUMINOIDS AS AMYLOID-BETA PET IMAGING AGENTS

CROSS REFERENCE TO RELATED APPLICATION

This application is a divisional of U.S. patent application Ser. No. 16/314,153, filed Dec. 28, 2018, which is a U.S. National Phase Application under 35 U.S.C. § 371 of International Patent Application No. PCT/US2017/039885, filed on Jun. 29, 2017, which claims the benefit of U.S. Application Nos. 62/451,433, filed on Jan. 27, 2017; and 62/356,116, filed on Jun. 29, 2016, which are incorporated by reference in their entirety.

FEDERALLY SPONSORED RESEARCH OR DEVELOPMENT

This invention was made with Government support under Grant No. K25AG036760, awarded by the National Institute of Health. The Government has certain rights in the invention.

TECHNICAL FIELD

Provided herein are curcumin analogues that are able to interact with amyloid beta (Aβ). Also provided herein are methods of using the compounds as imaging agents of amyloid beta and for the treatment of diseases associated with Aβ.

BACKGROUND

Three amyloid beta (Aβ) PET tracers have been approved by the FDA for clinical applications. However, they are only approved for exclusion of Alzheimer's disease (AD), and not for positive imaging diagnosis of AD. The fundamental limitation of the three approved tracers is that they are primarily useful for detecting insoluble Aβs, but not the more toxic soluble Aβ. Reports have indicated that curcumin may be a promising scaffold for developing PET tracer for Aβs, and many attempts have been made by many different groups, but none of them has been successful.

SUMMARY

The present application provides, inter alia, a compound of Formula I:

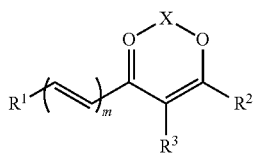

I a pharmaceutically acceptable salt thereof, or a tautomer thereof, wherein:

X is absent or $BR^4R^5$;

$R^1$ is selected from the group consisting of $C_{3-10}$ cycloalkyl, $C_{6-10}$ aryl, 4-10 membered heterocycloalkyl, and 5-10 membered heteroaryl, each of which may be optionally substituted by 1, 2, 3, or 4 independently selected $R^{1A}$ groups;

each $R^{1A}$ is independently selected from the group consisting of halo, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, $NR^{N1}R^{N2}$, $C_{3-10}$ cycloalkyl, $C_{6-10}$ aryl, 4-10 membered heterocycloalkyl, and 5-10 membered heteroaryl, wherein the $C_{1-6}$ alkyl, $C_{1-6}$ alkoxy, $C_{3-10}$ cycloalkyl, $C_{6-10}$ aryl, 4-10 membered heterocycloalkyl, and 5-10 membered heteroaryl are each optionally substituted by 1, 2, 3, or 4 independently selected $R^6$ groups;

$R^2$ is selected from the group consisting of $C_{1-6}$ alkyl, $C_{3-10}$ cycloalkyl, $C_{6-10}$ aryl, 4-10 membered heterocycloalkyl, and 5-10 membered heteroaryl, each of which may be optionally substituted by 1, 2, 3, or 4 independently selected $R^{2A}$ groups;

each $R^{2A}$ is independently selected from the group consisting of halo, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, $NR^{N1}R^{N2}$, $C_{3-10}$ cycloalkyl, $C_{6-10}$ aryl, 4-10 membered heterocycloalkyl, and 5-10 membered heteroaryl, wherein the $C_{1-6}$ alkyl, $C_{3-10}$ cycloalkyl, $C_{6-10}$ aryl, 4-10 membered heterocycloalkyl, and 5-10 membered heteroaryl are each optionally substituted by 1, 2, 3, or 4 independently selected $R^6$ groups;

$R^3$ is selected from the group consisting of H, $C_{1-6}$ alkyl, $C_{2-6}$ alkenyl, $C_{2-6}$ alkynyl, $C_{1-6}$ haloalkyl, $C_{1-6}$ alkoxy, and $C_{1-6}$ haloalkoxy;

$R^4$ and $R^5$ are each independently selected from the group consisting of H, halo, and $C_{1-6}$ alkoxy;

each $R^6$ is independently selected from the group consisting of OH, $NO_2$, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, and $-(C_{1-6}$ alkoxy)-$(C_{1-6}$ haloalkoxy);

each $R^{N1}$ is independently selected from the group consisting of H and $C_{1-6}$ alkyl;

each $R^{N2}$ is independently selected from the group consisting of $C_{2-6}$ alkyl, $C_{2-6}$ alkenyl, $C_{2-6}$ alkynyl, $C_{1-6}$ haloalkyl, $C_{1-6}$ alkoxy, and $C_{1-6}$ haloalkoxy; and m is 1 or 2.

In some embodiments, $R^1$ is selected from the group consisting of $C_{6-10}$ aryl and 5-10 membered heteroaryl, each of which may be optionally substituted by 1, 2, 3, or 4 independently selected $R^{1A}$ groups. In some embodiments, $R^1$ is selected from the group consisting of phenyl and 5-6 membered heteroaryl, each of which may be optionally substituted by 1, 2, 3, or 4 independently selected $R^{1A}$ groups. In some embodiments, $R^1$ is selected from the group consisting of phenyl, imidazolyl, pyrazolyl, triazolyl, and pyridyl, each of which may be optionally substituted by 1 or 2 independently selected $R^{1A}$ groups.

In some embodiments, each $R^{1A}$ is independently selected from the group consisting of halo, $C_{1-6}$ alkyl, $C_{1-6}$ haloalkyl, $C_{1-6}$ alkoxy, $C_{1-6}$ haloalkoxy, $NR^{N1}R^{N2}$ and $C_{6-10}$ aryl, wherein the $C_{1-6}$ alkyl, $C_{1-6}$ alkoxy, and $C_{6-10}$ aryl are each optionally substituted by 1, 2, 3, or 4 independently selected $R^6$ groups. In some embodiments, each $R^{1A}$ is independently selected from the group consisting of $C_{1-6}$ alkyl, $C_{1-6}$ alkoxy, $C_{1-6}$ haloalkoxy, $NR^{N1}R^{N2}$, and phenyl, wherein the $C_{1-6}$ alkyl, $C_{1-6}$ alkoxy, and phenyl are each optionally substituted by 1 or 2 independently selected $R^6$ groups. In some embodiments, each $R^{1A}$ is independently selected from the group consisting of methyl, $-CH_2CH_2OH$, $-OCH_2CH_2CH_2F$, $-OCH_2CH_2CH_2CH_2CH_2F$, $-OCH_2CH_2CH_2CH_2CH_2CH_2F$, $-OCH_2CH_2OCH_2CH_2F$, $-N(CH_2CH_3)_2$, $-N(CH_3)CH_2CH_2F$, and phenyl, wherein the phenyl is optionally substituted by $NO_2$, $C_{1-6}$ alkoxy, $C_{1-6}$ haloalkoxy, and $-(C_{1-6}$ alkoxy)-$(C_{1-6}$ haloalkoxy). In some embodiments, each $R^{1A}$ is independently selected from the group consisting of methyl, $-CH_2CH_2OH$, —OCH$_2$CH$_2$CH$_2$F, —OCH$_2$CH$_2$CH$_2$CH$_2$F, —OCH$_2$CH$_2$CH$_2$CH$_2$CH$_2$CH$_2$F, —OCH$_2$CH$_2$OCH$_2$CH$_2$F, —N(CH$_2$CH$_3$)$_2$, —N(CH$_3$)CH$_2$CH$_2$F, and phenyl, wherein the phenyl is optionally substituted by NO$_2$, —OCH$_3$, —OCH$_2$CH$_2$CH$_2$F, and —OCH$_2$CH$_2$OCH$_2$CH$_2$F.

In some embodiments, R$^2$ is selected from the group consisting of C$_{1-6}$ alkyl, C$_{3-6}$ cycloalkyl, and phenyl, each of which may be optionally substituted by 1, 2, 3, or 4 independently selected R$^{2A}$ groups. In some embodiments, R$^2$ is selected from the group consisting of C$_{1-6}$ alkyl, C$_{3-6}$ cycloalkyl, and phenyl. In some embodiments, R$^2$ is selected from the group consisting of methyl, cyclobutyl, and phenyl.

In some embodiments, R$^3$ is H.

In some embodiments, X is BR$^4$R$^5$. In some embodiments, X is absent, e.g., as shown below in Formula Ia:

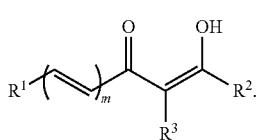

In some embodiments, R$^4$ and R$^5$ are each halo. In some embodiments, R$^4$ and R$^5$ are each fluoro.

In some embodiments, m is 1.

In some embodiments:
X is BR$^4$R$^5$;
R$^1$ is selected from the group consisting of C$_{6-10}$ aryl and 5-10 membered heteroaryl, each of which may be optionally substituted by 1, 2, 3, or 4 independently selected R$^{1A}$ groups;
each R$^{1A}$ is independently selected from the group consisting of halo, C$_{1-6}$ alkyl, C$_{1-6}$ haloalkyl, C$_{1-6}$ alkoxy, C$_{1-6}$ haloalkoxy, NR$^{N1}$R$^{N2}$, and C$_{6-10}$ aryl, wherein the C$_{1-6}$ alkyl, C$_{1-6}$ alkoxy, and C$_{6-10}$ aryl are each optionally substituted by 1, 2, 3, or 4 independently selected R$^6$ groups;
R$^2$ is selected from the group consisting of C$_{1-6}$ alkyl, C$_{3-6}$ cycloalkyl, and phenyl, each of which may be optionally substituted by 1, 2, 3, or 4 independently selected R$^{2A}$ groups;
R$^3$ is H;
R$^4$ and R$^5$ are each halo; and
m is 1.

In some embodiments:
X is BR$^4$R$^5$;
R$^1$ is selected from the group consisting of phenyl and 5-6 membered heteroaryl, each of which may be optionally substituted by 1, 2, 3, or 4 independently selected R$^{1A}$ group;
R$^{1A}$ is independently selected from the group consisting of C$_{1-6}$ alkyl, C$_{1-6}$ alkoxy, C$_{1-6}$ haloalkoxy, NR$^{N1}$R$^{N2}$ and phenyl, wherein the C$_{1-6}$ alkyl, C$_{1-6}$ alkoxy, and phenyl are each optionally substituted by 1 or 2 independently selected R$^6$ groups;
R$^2$ is selected from the group consisting of C$_{1-6}$ alkyl, C$_{3-6}$ cycloalkyl, and phenyl;
R$^3$ is H;
R$^4$ and R$^5$ are each halo; and
m is 1.

In some embodiments:
X is BR$^4$R$^5$;
R$^1$ is selected from the group consisting of phenyl, imidazolyl, pyrazolyl, triazolyl, and pyridyl, each of which may be optionally substituted by 1 or 2 independently selected R$^{1A}$ groups;

each R$^{1A}$ is independently selected from the group consisting of C$_{1-6}$ alkyl, C$_{1-6}$ alkoxy, C$_{1-6}$ haloalkoxy, NR$^{N1}$R$^{N2}$ and phenyl, wherein the C$_{1-6}$ alkyl, C$_{1-6}$ alkoxy, and phenyl are each optionally substituted by 1 or 2 independently selected R$^6$ groups;

R$^2$ is selected from the group consisting of methyl, cyclobutyl, and phenyl;

R$^3$ is H;

R$^4$ and R$^5$ are each halo; and m is 1.

In some embodiments, the compound of Formula I is a compound of Formula II:

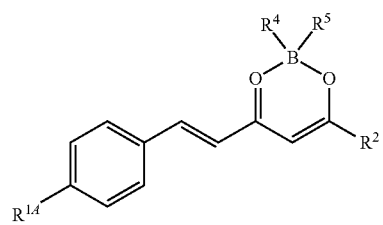

a pharmaceutically acceptable salt thereof, or a tautomer thereof.

In some embodiments, the compound of Formula I is a compound of Formula III:

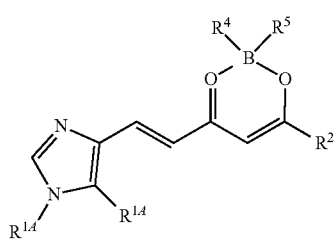

a pharmaceutically acceptable salt thereof, or a tautomer thereof.

In some embodiments, the compound of Formula I is a compound of Formula IV:

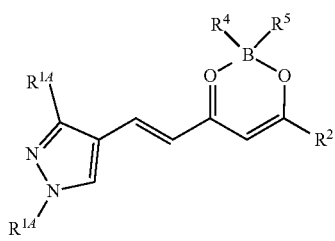

a pharmaceutically acceptable salt thereof, or a tautomer thereof.

In some embodiments, the compound of Formula I is a compound of Formula V:

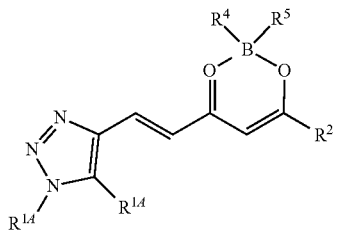

a pharmaceutically acceptable salt thereof, or a tautomer thereof.

In some embodiments, the compound of Formula I, a pharmaceutically acceptable salt thereof, or a tautomer thereof, comprises at least one radioisotope.

In some embodiments, the compound of Formula I, a pharmaceutically acceptable salt thereof, or a tautomer thereof, comprises at least one radioisotope selected from the group consisting of $^{11}$C, $^{13}$N, $^{15}$O, $^{18}$F, $^{68}$Ga, $^{89}$Zr, $^{82}$Rb, $^{124}$I, and $^{131}$I.

In some embodiments, the compound of Formula I, a pharmaceutically acceptable salt thereof, or a tautomer thereof, comprises at least one $^{18}$F radioisotope.

In some embodiments, the compound is selected from the group consisting of:

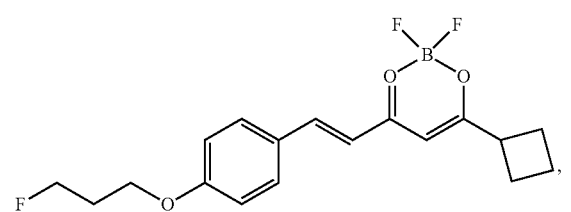

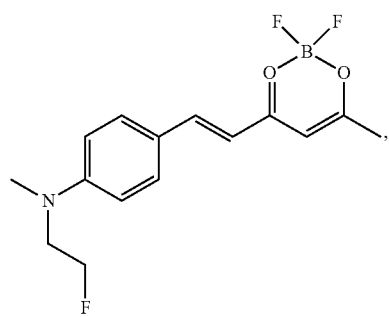

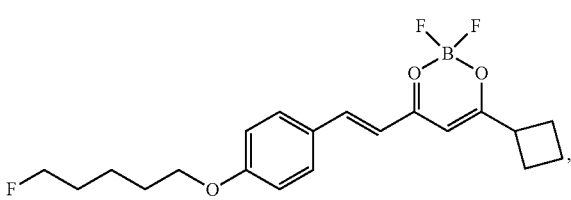

-continued

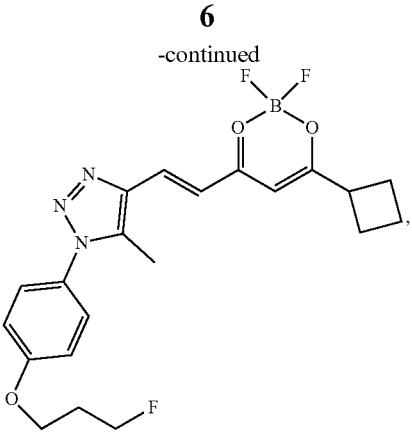

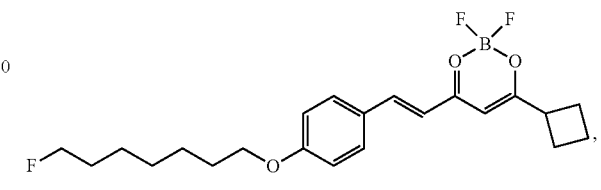

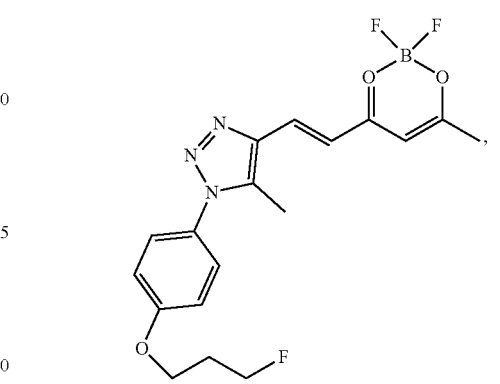

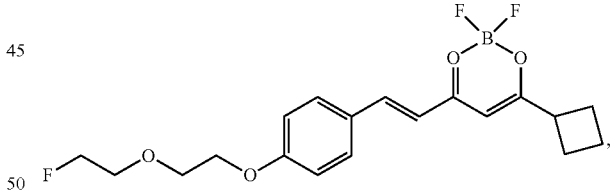

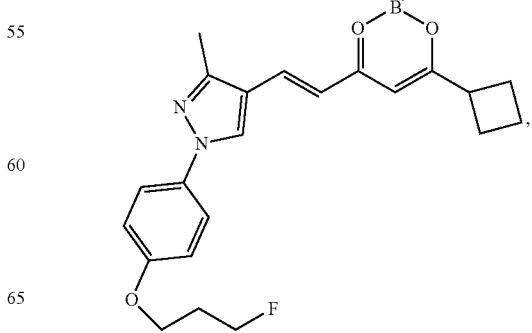

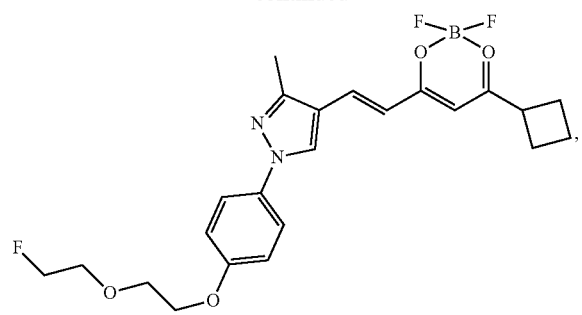
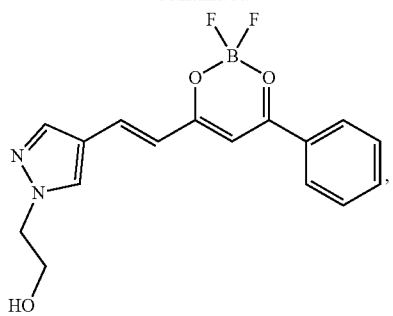
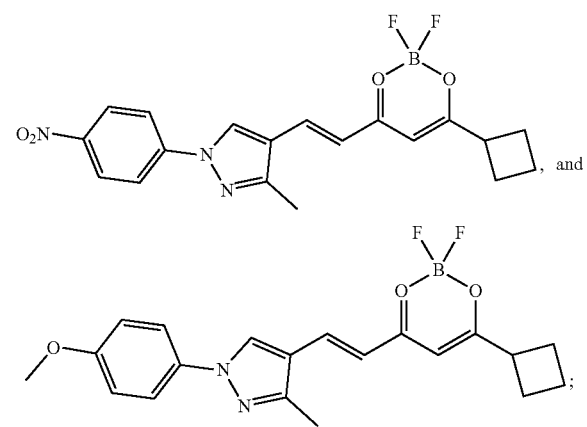
a pharmaceutically acceptable salt thereof, or a tautomer thereof.
In some embodiments, the compound is selected from the group consisting of:
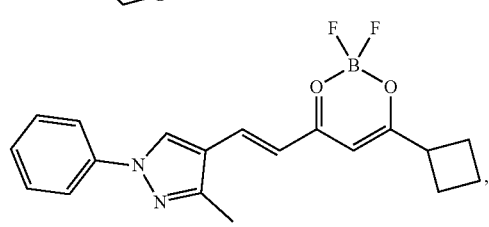
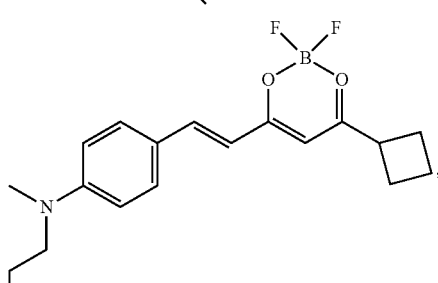
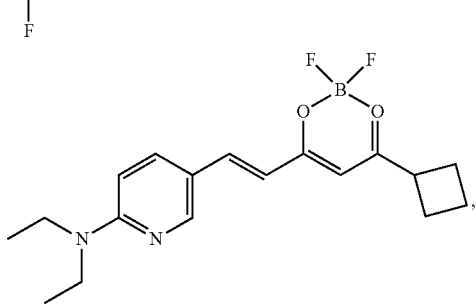
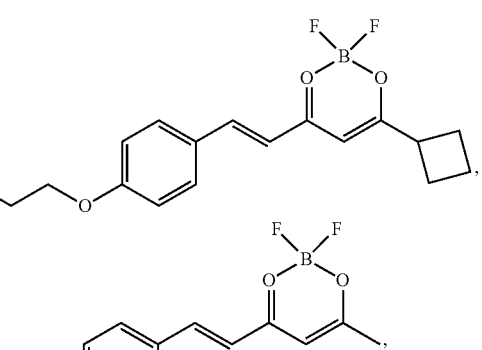
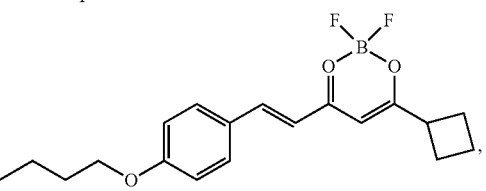

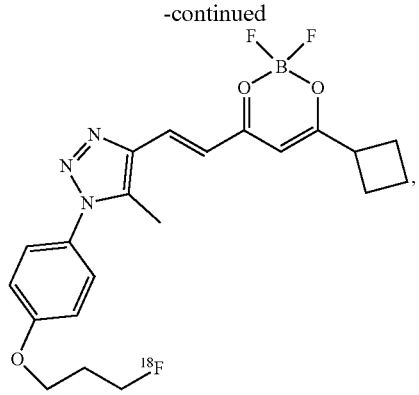
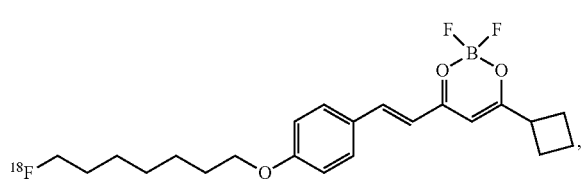
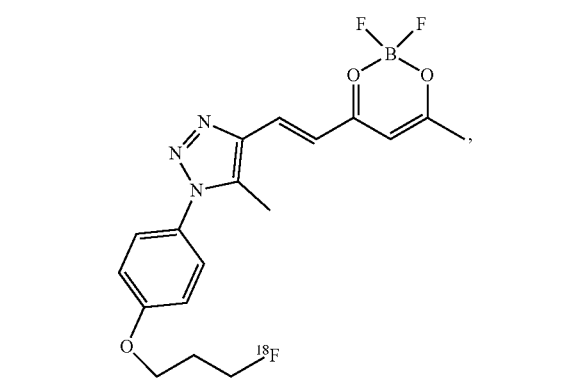
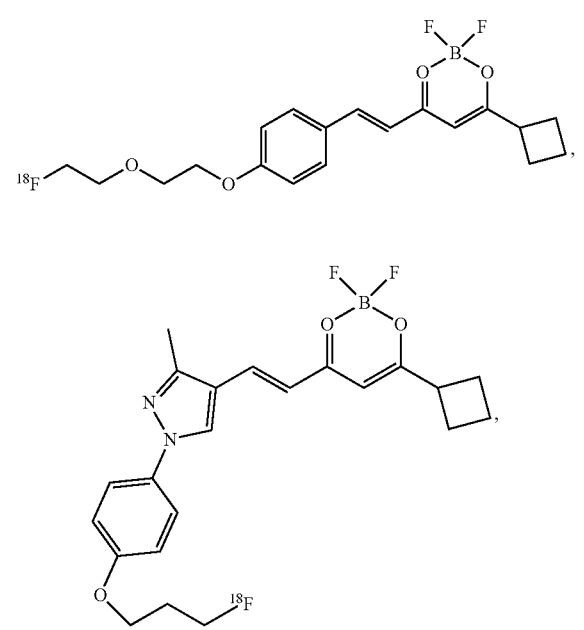

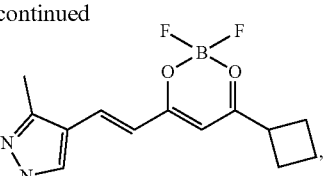
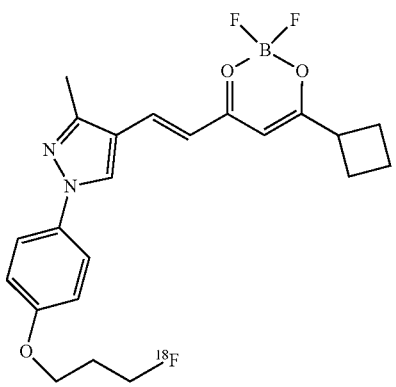

a pharmaceutically acceptable salt thereof, or a tautomer thereof.

In some embodiments, the compound is:

a pharmaceutically acceptable salt thereof, or a tautomer thereof.

The present application further provides a pharmaceutical composition, comprising a compound provided herein, a pharmaceutically acceptable salt thereof, or a tautomer thereof, and a pharmaceutically acceptable excipient.

The present application further provides a method of imaging amyloid beta in a subject, comprising:

i) administering to the subject a compound provided herein, a pharmaceutically acceptable salt thereof, or a tautomer thereof, and ii) imaging the cell or tissue with an imaging technique.

The present application further provides a method of diagnosing a disease associated with amyloid beta, comprising:

i) administering to the subject a compound provided herein, a pharmaceutically acceptable salt thereof, or a tautomer thereof, and ii) imaging the cell or tissue with an imaging technique.

In some embodiments, the disease is associated with amyloid beta plaque formation. In some embodiments, the disease is associated with amyloid beta crosslinking. In some embodiments, the disease is associated with copper-induced amyloid beta crosslinking.

In some embodiments, the disease is a disease of the central nervous system or a neurodegenerative disease. In some embodiments, the disease is selected from the group consisting of Alzheimer's Disease, senile dementia of AD type (SDAT), Parkinson's disease, Lewis body dementia, vascular dementia, mild cognitive impairment (MCI), age-associated memory impairment (AAMI) and problems associated with ageing, post-encephalitic Parkinsonism, Amyotrophic lateral sclerosis (ALS), multiple sclerosis (MS) and Down syndrome. In some embodiments, the disease is Alzheimer's Disease.

In some embodiments, the imaging technique is selected from the group consisting of fluorescence imaging, positron emission tomography imaging, magnetic resonance imaging, single-photon emission computed tomography, positron emission tomography with computed tomography imaging, and positron emission tomography with magnetic resonance imaging. In some embodiments, the imaging technique is selected from the group consisting of fluorescence imaging, position emission tomography imaging, and single-photon emission computed tomography.

In some embodiments, the amyloid beta comprises soluble amyloid beta. In some embodiments, the amyloid beta comprises insoluble amyloid beta.

The present application further provides a method for treating a disease selected from the group consisting of senile dementia of AD type (SDAT), Parkinson's disease, Lewis body dementia, vascular dementia, mild cognitive impairment (MCI), age-associated memory impairment (AAMI) and problems associated with ageing, post-encephalitic Parkinsonism, Amyotrophic lateral sclerosis (ALS), multiple sclerosis, (MS) and Down syndrome in a subject, the method comprising administering to the subject a therapeutically effective amount of a compound provided herein, a pharmaceutically acceptable salt thereof, or a tautomer thereof. In some embodiments, the disease is Alzheimer's Disease.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

DESCRIPTION OF DRAWINGS

FIG. 3C shows representative autoradiography images of an AD patient and control (non-AD) brain slices with CRANAD-101[$^{18}$F].

FIG. 3D shows fluorescence microscopic images of an AD patient brain slice with CRANAD-101. The image shows that CRANAD-101 can stain diffusible Aβ deposits (arrows).

FIG. 4A-4B show in vivo PET images using CRANAD-101[$^{18}$F]. The images are summed PET signal of 6-18 minutes post intravenous (i.v.) injection, and were co-registered with CT atlas image. Transverse images (left) and coronal brain images (right) of 14-month wild type mouse (FIG. 4A) and age-matched AD mouse (FIG. 4B) are shown.

FIG. 4C shows a time-activity curve of the CRANAD-101[$^{18}$F] in whole brains of 15-month WT mice and AD mice (APP/PS1 mice) (n=4).

FIG. 4D shows a time-activity curve of the CRANAD-101[$^{18}$F] in whole brains of 5-month WT mice and AD mice (APP/PS1 mice) (n=3).

DETAILED DESCRIPTION

Amyloid-beta (Aβ) deposits/plaques and tau tangles are indicators of Alzheimer's Disease (AD) (see e.g., Selkoe et al, Nature, 1999, 399: A23-31). During the progression of AD, Aβ peptides can form various sub-type species, which can be divided into two categories: soluble Aβs that include monomers, dimers, oligomers, and insoluble Aβs that include fibrils/aggregates and plaques. It has been reported that insoluble deposits/plaques in an AD brain solely cause neurodegeneration, however, evidence indicates that soluble Aβ species are more neurotoxic than insoluble deposits (see e.g., McLean et al, Ann. Neurol. 1999, 46:860-866; Lue et al, Am. J. Pathol. 1999, 155:853-862; and Terry et al, Ann. Neurol. 1991, 30:572-580).

Figure 1:
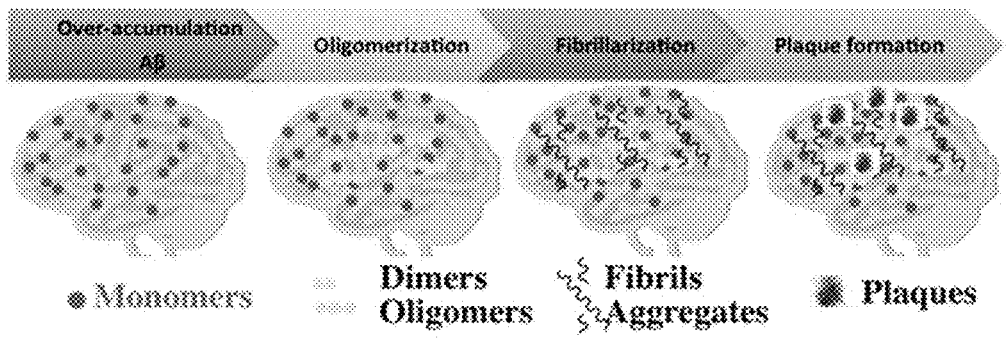
FIG. 1 shows a representative scheme of the progression of amyloidosis pathology.

For AD pathology, the initial stage is represented by the excessive accumulation of Aβ monomers caused by imbalanced Aβ clearance (see e.g., Hardy et al, Science, 2002, 297:353-356; and Mawuenyega et al, Science, 2011, 330: 1774-1776). The total accumulated Aβ then increases with the progression of the disease, and the early predominance of soluble species gradually shifts to primarily insoluble species (see also e.g., Hsiao et al, Science, 1996, 274:99-102; and Cao et al, The Journal of Biological Chemistry, 2007, 282:36275-36282). As shown in FIG. 1, both soluble and insoluble species co-exist during the disease progression, and both contribute to the AD pathology, indicating that imaging probes capable of detecting both soluble and insoluble Aβs would be useful. Accordingly, the present application provides compounds which are useful for interacting with and binding Aβ and may further be useful as imaging agents for imaging soluble and insoluble Aβ.

Compounds

The present application provides, inter alia, a compound of Formula I:

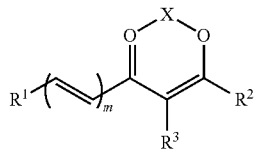

a pharmaceutically acceptable salt thereof, or a tautomer thereof, wherein:

X is absent or $BR^4R^5$;

$R^1$ is selected from the group consisting of $C_{3-10}$ cycloalkyl, $C_{6-10}$ aryl, 4-10 membered heterocycloalkyl, and 5-10 membered heteroaryl, each of which may be optionally substituted by 1, 2, 3, or 4 independently selected $R^{1A}$ groups;

each $R^{1A}$ is independently selected from the group consisting of halo, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, $NR^{N1}R^{N2}$, $C_{3-10}$ cycloalkyl, $C_{6-10}$ aryl, 4-10 membered heterocycloalkyl, and 5-10 membered heteroaryl, wherein the $C_{1-6}$ alkyl, $C_{1-6}$ alkoxy, $C_{3-10}$ cycloalkyl, $C_{6-10}$ aryl, 4-10 membered heterocycloalkyl, and 5-10 membered heteroaryl are each optionally substituted by 1, 2, 3, or 4 independently selected $R^6$ groups;

$R^2$ is selected from the group consisting of $C_{1-6}$ alkyl, $C_{3-10}$ cycloalkyl, $C_{6-10}$ aryl, 4-10 membered heterocycloalkyl, and 5-10 membered heteroaryl, each of which may be optionally substituted by 1, 2, 3, or 4 independently selected $R^{2A}$ groups;

each $R^{2A}$ is independently selected from the group consisting of halo, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, $NR^{N1}R^{N2}$, $C_{3-10}$ cycloalkyl, $C_{6-10}$ aryl, 4-10 membered heterocycloalkyl, and 5-10 membered heteroaryl, wherein the $C_{1-6}$ alkyl, $C_{3-10}$ cycloalkyl, $C_{6-10}$ aryl, 4-10 membered heterocycloalkyl, and 5-10 membered heteroaryl are each optionally substituted by 1, 2, 3, or 4 independently selected $R^6$ groups;

$R^3$ is selected from the group consisting of H, $C_{1-6}$ alkyl, $C_{2-6}$ alkenyl, $C_{2-6}$ alkynyl, $C_{1-6}$ haloalkyl, $C_{1-6}$ alkoxy, and $C_{1-6}$ haloalkoxy;

$R^4$ and $R^5$ are each independently selected from the group consisting of H, halo, and $C_{1-6}$ alkoxy;

each $R^6$ is independently selected from the group consisting of OH, $NO_2$, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, and —($C_{1-6}$ alkoxy)-($C_{1-6}$ haloalkoxy);

each $R^{N1}$ is independently selected from the group consisting of H and $C_{1-6}$ alkyl; each $R^{N2}$ is independently selected from the group consisting of $C_{2-6}$ alkyl, $C_{2-6}$ alkenyl, $C_{2-6}$ alkynyl, $C_{1-6}$ haloalkyl, $C_{1-6}$ alkoxy, and $C_{1-6}$ haloalkoxy; and m is 1 or 2.

In some embodiments:

X is absent or $BR^4R^5$;

$R^1$ is selected from the group consisting of $C_{3-10}$ cycloalkyl, $C_{6-10}$ aryl, 4-10 membered heterocycloalkyl, and 5-10 membered heteroaryl, each of which may be optionally substituted by 1, 2, 3, or 4 independently selected $R^{1A}$ groups;

each $R^{1A}$ is independently selected from the group consisting of halo, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, $NR^{N1}R^{N2}$, $C_{3-10}$ cycloalkyl, $C_{6-10}$ aryl, 4-10 membered heterocycloalkyl, and 5-10 membered heteroaryl, wherein the $C_{1-6}$ alkyl, $C_{1-6}$ alkoxy, $C_{3-10}$ cycloalkyl, $C_{6-10}$ aryl, 4-10 membered heterocycloalkyl, and 5-10 membered heteroaryl are each optionally substituted by 1, 2, 3, or 4 independently selected $R^6$ groups;

$R^2$ is selected from the group consisting of $C_{1-6}$ alkyl, $C_{3-10}$ cycloalkyl, $C_{6-10}$ aryl, 4-10 membered heterocycloalkyl, and 5-10 membered heteroaryl, each of which may be optionally substituted by 1, 2, 3, or 4 independently selected $R^{2A}$ groups;

each $R^{2A}$ is independently selected from the group consisting of halo, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, $NR^{N1}R^{N2}$, $C_{3-10}$ cycloalkyl, $C_{6-10}$ aryl, 4-10 membered heterocycloalkyl, and 5-10 membered heteroaryl, wherein the $C_{1-6}$ alkyl, $C_{3-10}$ cycloalkyl, $C_{6-10}$ aryl, 4-10 membered heterocycloalkyl, and 5-10 membered heteroaryl are each optionally substituted by 1, 2, 3, or 4 independently selected $R^6$ groups;

$R^3$ is selected from the group consisting of H, $C_{1-6}$ alkyl, $C_{2-6}$ alkenyl, $C_{2-6}$ alkynyl, $C_{1-6}$ haloalkyl, $C_{1-6}$ alkoxy, and $C_{1-6}$ haloalkoxy;

$R^4$ and $R^5$ are each independently selected from the group consisting of H, halo, and $C_{1-6}$ alkoxy;

each $R^6$ is independently selected from the group consisting of OH, $NO_2$, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, and —($C_{1-6}$ alkoxy)-($C_{1-6}$ haloalkoxy);

each $R^{N1}$ is independently selected from the group consisting of H and $C_{1-6}$ alkyl;

each $R^{N2}$ is independently selected from the group consisting of $C_{2-6}$ alkenyl, $C_{2-6}$ alkynyl, $C_{1-6}$ haloalkyl, $C_{1-6}$ alkoxy, and $C_{1-6}$ haloalkoxy; and m is 1 or 2.

In some embodiments, $R^1$ is selected from the group consisting of $C_{6-10}$ aryl and 5-10 membered heteroaryl, each of which may be optionally substituted by 1, 2, 3, or 4 independently selected $R^{1A}$ groups.

In some embodiments, $R^1$ is selected from the group consisting of $C_{6-10}$ aryl and 5-10 membered heteroaryl, each of which may be optionally substituted by 1 or 2 independently selected $R^{1A}$ groups.

In some embodiments, $R^1$ is selected from the group consisting of phenyl and 5-6 membered heteroaryl, each of which may be optionally substituted by 1, 2, 3, or 4 independently selected $R^{1A}$ groups.

In some embodiments, $R^1$ is selected from the group consisting of phenyl and 5-6 membered heteroaryl, each of which may be optionally substituted by 1 or 2 independently selected $R^{1A}$ groups. In some embodiments, $R^1$ is selected from the group consisting of phenyl, imidazolyl, pyrazolyl, triazolyl, and pyridyl, each of which may be optionally substituted by 1, 2, 3, or 4 independently selected $R^{1A}$ groups. In some embodiments, $R^1$ is selected from the group consisting of phenyl, imidazolyl, pyrazolyl, triazolyl, and pyridyl, each of which may be optionally substituted by 1 or 2 independently selected $R^{1A}$ groups. In some embodiments, $R^1$ is selected from the group consisting of phenyl, imidazolyl, and pyrazolyl, each of which may be optionally substituted by 1 or 2 independently selected $R^{14}$ groups.

In some embodiments, each $R^{14}$ is independently selected from the group consisting of halo, $C_{1-6}$ alkyl, $C_{1-6}$ haloalkyl, $C_{1-6}$ alkoxy, $C_{1-6}$ haloalkoxy, $NR^{N1}R^{N2}$ and $C_{6-10}$ aryl, wherein the $C_{1-6}$ alkyl, $C_{1-6}$ alkoxy, and $C_{6-10}$ aryl are each optionally substituted by 1, 2, 3, or 4 independently selected $R^6$ groups. In some embodiments, each $R^{14}$ is independently selected from the group consisting of halo, $C_{1-6}$ alkyl, $C_{1-6}$ haloalkyl, $C_{1-6}$ alkoxy, $C_{1-6}$ haloalkoxy, $NR^{N1}R^{N2}$, and $C_{6-10}$ aryl, wherein the $C_{1-6}$ alkyl, $C_{1-6}$ alkoxy, and $C_{6-10}$ aryl are each optionally substituted by 1 or 2 independently selected $R^6$ groups. In some embodiments, each $R^{14}$ is independently selected from the group consisting of $C_{1-6}$ alkyl, $C_{1-6}$ alkoxy, $C_{1-6}$ haloalkoxy, $NR^{N1}R^{N2}$ and phenyl, wherein the $C_{1-6}$ alkyl, $C_{1-6}$ alkoxy, and phenyl are each optionally substituted by 1, 2, 3, or 4 independently selected $R^6$ groups. In some embodiments, each $R^{14}$ is independently selected from the group consisting of $C_{1-6}$ alkyl, $C_{1-6}$ alkoxy, $C_{1-6}$ haloalkoxy, $NR^{N1}R^{N2}$ and phenyl, wherein the $C_{1-6}$ alkyl, $C_{1-6}$ alkoxy, and phenyl are each optionally substituted by 1 or 2 independently selected $R^6$ groups.

In some embodiments, each $R^{14}$ is independently selected from the group consisting of methyl, —$CH_2CH_2OH$, —$OCH_2CH_2CH_2F$, —$OCH_2CH_2CH_2CH_2CH_2F$, —$OCH_2CH_2CH_2CH_2CH_2CH_2F$, —$OCH_2CH_2OCH_2CH_2F$, —$N(CH_2CH_3)_2$, —$N(CH_3)CH_2CH_2F$, and phenyl, wherein the phenyl is optionally substituted by $NO_2$, $C_{1-6}$ alkoxy, $C_{1-6}$ haloalkoxy, and —($C_{1-6}$ alkoxy)-($C_{1-6}$ haloalkoxy). In some embodiments, each $R^{14}$ is independently selected from the group consisting of methyl, —$CH_2CH_2OH$, —$OCH_2CH_2CH_2^{18}F$, —$OCH_2CH_2CH_2CH_2CH_2^{18}F$, —$OCH_2CH_2CH_2CH_2CH_2CH_2^{18}F$, —$OCH_2CH_2OCH_2CH_2^{18}F$, —$N(CH_2CH_3)_2$, —$N(CH_3)CH_2CH_2^{18}F$, and phenyl, wherein the phenyl is optionally substituted by $NO_2$, $C_{1-6}$ alkoxy, $C_{1-6}$ haloalkoxy, and —($C_{1-6}$ alkoxy)-($C_{1-6}$ haloalkoxy).

In some embodiments, each $R^{14}$ is independently selected from the group consisting of methyl, —$CH_2CH_2OH$, —$OCH_2CH_2CH_2F$, —$OCH_2CH_2CH_2CH_2CH_2F$, —$OCH_2CH_2CH_2CH_2CH_2CH_2F$, —$OCH_2CH_2OCH_2CH_2F$, —$N(CH_2CH_3)_2$, —$N(CH_3)CH_2CH_2F$, and phenyl, wherein the phenyl is optionally substituted by $NO_2$, —$OCH_3$, —$OCH_2CH_2CH_2F$, and —$OCH_2CH_2OCH_2CH_2F$. In some embodiments, each $R^{14}$ is independently selected from the group consisting of methyl, —$CH_2CH_2OH$, —$OCH_2CH_2CH_2F$, —$OCH_2CH_2CH_2CH_2CH_2^{18}F$, —$OCH_2CH_2CH_2CH_2CH_2CH_2^{18}F$, —$OCH_2CH_2OCH_2CH_2^{18}F$, —$N(CH_2CH_3)_2$, —$N(CH_3)CH_2CH_2^{18}F$, and phenyl, wherein the phenyl is optionally substituted by $NO_2$, —$OCH_3$, —$OCH_2CH_2CH_2^{18}F$, and —$OCH_2CH_2OCH_2CH_2^{18}F$.

In some embodiments, $R^2$ is selected from the group consisting of $C_{1-6}$ alkyl, $C_{3-10}$ cycloalkyl, $C_{6-10}$ aryl, 4-10 membered heterocycloalkyl, and 5-10 membered heteroaryl. In some embodiments, $R^2$ is selected from the group consisting of $C_{1-6}$ alkyl, $C_{3-10}$ cycloalkyl, and $C_{6-10}$ aryl each of which may be optionally substituted by 1, 2, 3, or 4 independently selected $R^{24}$ groups. In some embodiments, $R^2$ is selected from the group consisting of $C_{1-6}$ alkyl, $C_{3-6}$ cycloalkyl, and phenyl, each of which may be optionally substituted by 1, 2, 3, or 4 independently selected $R^{24}$ groups. In some embodiments, $R^2$ is selected from the group consisting of $C_{1-6}$ alkyl, $C_{3-10}$ cycloalkyl, and phenyl. In some embodiments, $R^2$ is selected from the group consisting of $C_{1-6}$ alkyl, cyclobutyl, adamantyl, and phenyl. In some embodiments, $R^2$ is selected from the group consisting of $C_{1-6}$ alkyl, $C_{3-6}$ cycloalkyl, and phenyl. In some embodiments, $R^2$ is selected from the group consisting of methyl, cyclobutyl, adamantyl, and phenyl. In some embodiments, $R^2$ is selected from the group consisting of methyl, cyclobutyl, and phenyl.

In some embodiments, $R^3$ is selected from the group consisting of H and $C_{1-6}$ alkyl, $C_{2-6}$ alkenyl, and $C_{2-6}$ alkynyl. In some embodiment, $R^3$ is selected from the group consisting of $C_{1-6}$ haloalkyl, $C_{1-6}$ alkoxy, and $C_{1-6}$ haloalkoxy. In some embodiments, $R^3$ is selected from the group consisting of H and $C_{1-6}$ alkyl. In some embodiments, $R^3$ is H.

In some embodiments, X is absent. In some embodiments, X is —$BR^4R^5$. In some embodiments, $R^4$ is halo. In some embodiments, $R^4$ is fluoro. In some embodiments, $R^5$ is halo. In some embodiments, $R^5$ is fluoro. In some embodiments, $R^4$ and $R^5$ are each halo. In some embodiments, $R^4$ and $R^5$ are each fluoro.

In some embodiments, m is 1. In some embodiments, m is 2.

In some embodiments:
X is $BR^4R^5$;
$R^1$ is selected from the group consisting of $C_{6-10}$ aryl and 5-10 membered heteroaryl, each of which may be optionally substituted by 1, 2, 3, or 4 independently selected $R^{14}$ groups;
each $R^{14}$ is independently selected from the group consisting of halo, $C_{1-6}$ alkyl, $C_{1-6}$ haloalkyl, $C_{1-6}$ alkoxy, $C_{1-6}$ haloalkoxy, $NR^{N1}R^{N2}$, and $C_{6-10}$ aryl, wherein the $C_{1-6}$ alkyl, $C_{1-6}$ alkoxy, and $C_{6-10}$ aryl are each optionally substituted by 1, 2, 3, or 4 independently selected $R^6$ groups;
$R^2$ is selected from the group consisting of $C_{1-6}$ alkyl, $C_{3-6}$ cycloalkyl, and phenyl, each of which may be optionally substituted by 1, 2, 3, or 4 independently selected $R^{24}$ groups;
$R^3$ is H;
$R^4$ and $R^5$ are each halo; and
m is 1.

In some embodiments:
X is $BR^4R^5$;
$R^1$ is selected from the group consisting of phenyl and 5-6 membered heteroaryl, each of which may be optionally substituted by 1, 2, 3, or 4 independently selected $R^{14}$ group;
$R^{14}$ is independently selected from the group consisting of $C_{1-6}$ alkyl, $C_{1-6}$ alkoxy, $C_{1-6}$ haloalkoxy, $NR^{N1}R^{N2}$, and phenyl, wherein the $C_{1-6}$ alkyl, $C_{1-6}$ alkoxy, and phenyl are each optionally substituted by 1 or 2 independently selected $R^6$ groups;
$R^2$ is selected from the group consisting of $C_{1-6}$ alkyl, $C_{3-6}$ cycloalkyl, and phenyl;
$R^3$ is H;
$R^4$ and $R^5$ are each halo; and
m is 1.

In some embodiments:
X is $BR^4R^5$;
$R^1$ is selected from the group consisting of phenyl, imidazolyl, pyrazolyl, triazolyl, and pyridyl, each of which may be optionally substituted by 1 or 2 independently selected $R^{14}$ groups;
each $R^{14}$ is independently selected from the group consisting of $C_{1-6}$ alkyl, $C_{1-6}$ alkoxy, $C_{1-6}$ haloalkoxy, $NR^{N1}R^{N2}$, and phenyl, wherein the $C_{1-6}$ alkyl, $C_{1-6}$ alkoxy, and phenyl are each optionally substituted by 1 or 2 independently selected $R^6$ groups;

$R^2$ is selected from the group consisting of methyl, cyclobutyl, and phenyl;

$R^3$ is H;

$R^4$ and $R^5$ are each halo; and m is 1.

In some embodiments, each $R^6$ is independently selected from the group consisting of OH, $NO_2$, $C_{1-6}$ alkyl, $C_{1-6}$ haloalkyl, $C_{1-6}$ alkoxy, $C_{1-6}$ haloalkoxy, and $-(C_{1-6}$ alkoxy)-$(C_{1-6}$ haloalkoxy). In some embodiments, each $R^6$ is independently selected from the group consisting of OH, $NO_2$, $C_{1-6}$ haloalkyl, $C_{1-6}$ alkoxy, $C_{1-6}$ haloalkoxy, and $-(C_{1-6}$ alkoxy)-$(C_{1-6}$ haloalkoxy). In some embodiments, each $R^6$ is independently selected from the group consisting of OH, $NO_2$, $-OCH_3$, $-CH_2F$, $-CH_2CH_2CH_2F$, and $-OCH_2CH_2OCH_2CH_2F$. In some embodiments, each $R^6$ is independently selected from the group consisting of OH, $NO_2$, $-OCH_3$, $-CH_2{}^{18}F$, $-CH_2CH_2CH_2{}^{18}F$, and $-OCH_2CH_2OCH_2CH_2{}^{18}F$.

In some embodiments, the compound of Formula I is a compound of Formula II.

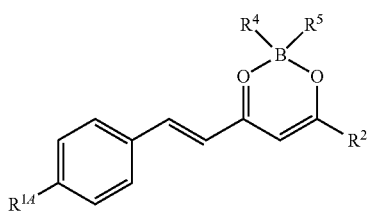

II a pharmaceutically acceptable salt thereof, or a tautomer thereof, wherein variables $R^{1A}$, $R^2$, $R^4$, and $R^5$ are defined according to the definitions provided herein for compounds of Formula I.

In some embodiments, each $R^{1A}$ is independently selected from the group consisting of halo, $C_{1-6}$ alkyl, $C_{1-6}$ haloalkyl, $C_{1-6}$ alkoxy, $C_{1-6}$ haloalkoxy, $NR^{N1}R^{N2}$ and $C_{6-10}$ aryl, wherein the $C_{1-6}$ alkyl, $C_{1-6}$ alkoxy, and $C_{6-10}$ aryl are each optionally substituted by 1, 2, 3, or 4 independently selected $R^6$ groups. In some embodiments, each $R^{1A}$ is independently selected from the group consisting of halo, $C_{1-6}$ alkyl, $C_{1-6}$ haloalkyl, $C_{1-6}$ alkoxy, $C_{1-6}$ haloalkoxy, $NR^{N1}R^{N2}$, and $C_{6-10}$ aryl, wherein the $C_{1-6}$ alkyl, $C_{1-6}$ alkoxy, and $C_{6-10}$ aryl are each optionally substituted by 1 or 2 independently selected $R^6$ groups. In some embodiments, each $R^{1A}$ is independently selected from the group consisting of $C_{1-6}$ alkyl, $C_{1-6}$ alkoxy, $C_{1-6}$ haloalkoxy, $NR^{N1}R^{N2}$ and phenyl, wherein the $C_{1-6}$ alkyl, $C_{1-6}$ alkoxy, and phenyl are each optionally substituted by 1, 2, 3, or 4 independently selected $R^6$ groups. In some embodiments, each $R^{1A}$ is independently selected from the group consisting of $C_{1-6}$ alkyl, $C_{1-6}$ alkoxy, $C_{1-6}$ haloalkoxy, $NR^{N1}R^{N2}$ and phenyl, wherein the $C_{1-6}$ alkyl, $C_{1-6}$ alkoxy, and phenyl are each optionally substituted by 1 or 2 independently selected $R^6$ groups.

In some embodiments, each $R^{1A}$ is independently selected from the group consisting of methyl, $-CH_2CH_2OH$, $-OCH_2CH_2CH_2F$, $-OCH_2CH_2CH_2CH_2CH_2F$, $-OCH_2CH_2CH_2CH_2CH_2CH_2F$, $-OCH_2CH_2OCH_2CH_2F$, $-N(CH_2CH_3)_2$, $-N(CH_3)CH_2CH_2F$, and phenyl, wherein the phenyl is optionally substituted by $NO_2$, $-OCH_3$, $-OCH_2CH_2CH_2F$, and $-OCH_2CH_2OCH_2CH_2F$. In some embodiments, each $R^{1A}$ is independently selected from the group consisting of methyl, $-CH_2CH_2OH$, $-OCH_2CH_2CH_2F$, $-OCH_2CH_2CH_2CH_2CH_2{}^{18}F$, $-OCH_2CH_2CH_2CH_2CH_2CH_2{}^{18}F$, $-OCH_2CH_2{}^{18}F$, $-N(CH_2CH_3)_2$, $-N(CH_3)CH_2CH_2{}^{18}F$, and phenyl, wherein the phenyl is optionally substituted by $NO_2$, $-OCH_3$, $-OCH_2CH_2CH_2{}^{18}F$, and $-OCH_2CH_2OCH_2CH_2{}^{18}F$.

In some embodiments, $R^2$ is selected from the group consisting of $C_{1-6}$ alkyl, $C_{3-10}$ cycloalkyl, $C_{6-10}$ aryl, 4-10 membered heterocycloalkyl, and 5-10 membered heteroaryl. In some embodiments, $R^2$ is selected from the group consisting of $C_{1-6}$ alkyl, $C_{3-10}$ cycloalkyl, and $C_{6-10}$ aryl each of which may be optionally substituted by 1, 2, 3, or 4 independently selected $R^{2A}$ groups. In some embodiments, $R^2$ is selected from the group consisting of $C_{1-6}$ alkyl, $C_{3-6}$ cycloalkyl, and phenyl, each of which may be optionally substituted by 1, 2, 3, or 4 independently selected $R^{2A}$ groups. In some embodiments, $R^2$ is selected from the group consisting of $C_{1-6}$ alkyl, $C_{3-10}$ cycloalkyl, and phenyl. In some embodiments, $R^2$ is selected from the group consisting of $C_{1-6}$ alkyl, cyclobutyl, adamantyl, and phenyl. In some embodiments, $R^2$ is selected from the group consisting of $C_{1-6}$ alkyl, $C_{3-6}$ cycloalkyl, and phenyl. In some embodiments, $R^2$ is selected from the group consisting of methyl, cyclobutyl, adamantyl, and phenyl. In some embodiments, $R^2$ is selected from the group consisting of methyl, cyclobutyl, and phenyl.

In some embodiments, $R^4$ and $R^5$ are each halo. In some embodiments, $R^4$ and $R^5$ are each fluoro.

In some embodiments, each $R^6$ is independently selected from the group consisting of OH, $NO_2$, $C_{1-6}$ alkyl, $C_{1-6}$ haloalkyl, $C_{1-6}$ alkoxy, $C_{1-6}$ haloalkoxy, and $-(C_{1-6}$ alkoxy)-$(C_{1-6}$ haloalkoxy). In some embodiments, each $R^6$ is independently selected from the group consisting of OH, $NO_2$, $C_{1-6}$ haloalkyl, $C_{1-6}$ alkoxy, $C_{1-6}$ haloalkoxy, and $-(C_{1-6}$ alkoxy)-$(C_{1-6}$ haloalkoxy). In some embodiments, each $R^6$ is independently selected from the group consisting of OH, $NO_2$, $-OCH_3$, $-CH_2F$, $-CH_2CH_2CH_2F$, and $-OCH_2CH_2OCH_2CH_2F$. In some embodiments, each $R^6$ is independently selected from the group consisting of OH, $NO_2$, $-OCH_3$, $-CH_2{}^{18}F$, $-CH_2CH_2CH_2{}^{18}F$, and $-OCH_2CH_2OCH_2CH_2{}^{18}F$.

In some embodiments, the compound of Formula I is a compound of Formula III:

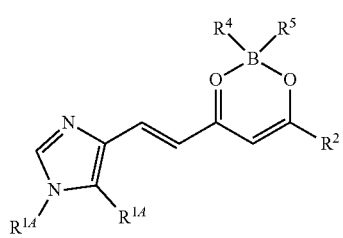

III a pharmaceutically acceptable salt thereof, or a tautomer thereof, wherein variables $R^{1A}$, $R^2$, $R^4$, and $R^5$ are defined according to the definitions provided herein for compounds of Formula I.

In some embodiments, each $R^{1A}$ is independently selected from the group consisting of halo, $C_{1-6}$ alkyl, $C_{1-6}$ haloalkyl, $C_{1-6}$ alkoxy, $C_{1-6}$ haloalkoxy, $NR^{N1}R^{N2}$ and $C_{6-10}$ aryl, wherein the $C_{1-6}$ alkyl, $C_{1-6}$ alkoxy, and $C_{6-10}$ aryl are each optionally substituted by 1, 2, 3, or 4 independently selected $R^6$ groups. In some embodiments, each $R^{1A}$ is independently selected from the group consisting of halo, $C_{1-6}$ alkyl, $C_{1-6}$ haloalkyl, $C_{1-6}$ alkoxy, $C_{1-6}$ haloalkoxy, $NR^{N1}R^{N2}$, and $C_{6-10}$ aryl, wherein the $C_{1-6}$ alkyl, $C_{1-6}$ alkoxy, and $C_{6-10}$ aryl are each optionally substituted by 1 or 2 independently selected $R^6$ groups. In some embodiments, each $R^{1A}$ is independently selected from the group consisting of $C_{1-6}$ alkyl, $C_{1-6}$ alkoxy, $C_{1-6}$ haloalkoxy, $NR^{N1}R^{N2}$ and phenyl, wherein the $C_{1-6}$ alkyl, $C_{1-6}$ alkoxy, and phenyl are each optionally substituted by 1, 2, 3, or 4 independently selected $R^6$ groups. In some embodiments, each $R^{1A}$ is independently selected from the group consisting of $C_{1-6}$ alkyl, $C_{1-6}$ alkoxy, $C_{1-6}$ haloalkoxy, $NR^{N1}R^{N2}$ and phenyl, wherein the $C_{1-6}$ alkyl, $C_{1-6}$ alkoxy, and phenyl are each optionally substituted by 1 or 2 independently selected $R^6$ groups.

In some embodiments, each $R^{1A}$ is independently selected from the group consisting of methyl, —$CH_2CH_2OH$, —$OCH_2CH_2CH_2F$, —$OCH_2CH_2CH_2CH_2CH_2F$, —$OCH_2CH_2CH_2CH_2CH_2CH_2F$, —$OCH_2CH_2OCH_2CH_2F$, —$N(CH_2CH_3)_2$, —$N(CH_3)CH_2CH_2F$, and phenyl, wherein the phenyl is optionally substituted by $NO_2$, —$OCH_3$, —$OCH_2CH_2CH_2F$, and —$OCH_2CH_2OCH_2CH_2F$. In some embodiments, each $R^{1A}$ is independently selected from the group consisting of methyl, —$CH_2CH_2OH$, —$OCH_2CH_2CH_2F$, —$OCH_2CH_2CH_2CH_2CH_2{}^{18}F$, —$OCH_2CH_2CH_2CH_2CH_2CH_2{}^{18}F$, —$OCH_2CH_2OCH_2CH_2{}^{18}F$, —$N(CH_2CH_3)_2$, —$N(CH_3)CH_2CH_2{}^{18}F$, and phenyl, wherein the phenyl is optionally substituted by $NO_2$, —$OCH_3$, —$OCH_2CH_2CH_2{}^{18}F$, and —$OCH_2CH_2OCH_2CH_2{}^{18}F$.

In some embodiments, $R^2$ is selected from the group consisting of $C_{1-6}$ alkyl, $C_{3-10}$ cycloalkyl, $C_{6-10}$ aryl, 4-10 membered heterocycloalkyl, and 5-10 membered heteroaryl. In some embodiments, $R^2$ is selected from the group consisting of $C_{1-6}$ alkyl, $C_{3-10}$ cycloalkyl, and $C_{6-10}$ aryl each of which may be optionally substituted by 1, 2, 3, or 4 independently selected $R^{2A}$ groups. In some embodiments, $R^2$ is selected from the group consisting of $C_{1-6}$ alkyl, $C_{3-6}$ cycloalkyl, and phenyl, each of which may be optionally substituted by 1, 2, 3, or 4 independently selected $R^{2A}$ groups. In some embodiments, $R^2$ is selected from the group consisting of $C_{1-6}$ alkyl, $C_{3-10}$ cycloalkyl, and phenyl. In some embodiments, $R^2$ is selected from the group consisting of $C_{1-6}$ alkyl, cyclobutyl, adamantyl, and phenyl. In some embodiments, $R^2$ is selected from the group consisting of $C_{1-6}$ alkyl, $C_{3-6}$ cycloalkyl, and phenyl. In some embodiments, $R^2$ is selected from the group consisting of methyl, cyclobutyl, adamantyl, and phenyl. In some embodiments, $R^2$ is selected from the group consisting of methyl, cyclobutyl, and phenyl.

In some embodiments, $R^4$ and $R^5$ are each halo. In some embodiments, $R^4$ and $R^5$ are each fluoro.

In some embodiments, each $R^6$ is independently selected from the group consisting of OH, $NO_2$, $C_{1-6}$ alkyl, $C_{1-6}$ haloalkyl, $C_{1-6}$ alkoxy, $C_{1-6}$ haloalkoxy, and —($C_{1-6}$ alkoxy)-($C_{1-6}$ haloalkoxy). In some embodiments, each $R^6$ is independently selected from the group consisting of OH, $NO_2$, $C_{1-6}$ haloalkyl, $C_{1-6}$ alkoxy, $C_{1-6}$ haloalkoxy, and —($C_{1-6}$ alkoxy)-($C_{1-6}$ haloalkoxy). In some embodiments, each $R^6$ is independently selected from the group consisting of OH, $NO_2$, —$OCH_3$, —$CH_2F$, —$CH_2CH_2CH_2F$, and —$OCH_2CH_2OCH_2CH_2F$. In some embodiments, each $R^6$ is independently selected from the group consisting of OH, $NO_2$, —$OCH_3$, —$CH_2{}^{11}F$, —$CH_2CH_2CH_2{}^{18}F$, and —$OCH_2CH_2OCH_2CH_2{}^{18}F$.

In some embodiments, the compound of Formula I is a compound of Formula IV:

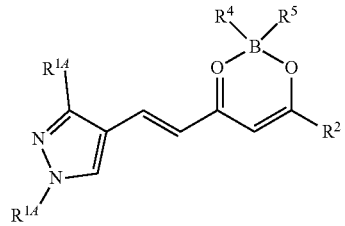

IV a pharmaceutically acceptable salt thereof, or a tautomer thereof, wherein variables $R^{1A}$, $R^2$, $R^4$, and $R^5$ are defined according to the definitions provided herein for compounds of Formula I.

In some embodiments, each $R^{1A}$ is independently selected from the group consisting of halo, $C_{1-6}$ alkyl, $C_{1-6}$ haloalkyl, $C_{1-6}$ alkoxy, $C_{1-6}$ haloalkoxy, $NR^{N1}R^{N2}$ and $C_{6-10}$ aryl, wherein the $C_{1-6}$ alkyl, $C_{1-6}$ alkoxy, and $C_{6-10}$ aryl are each optionally substituted by 1, 2, 3, or 4 independently selected $R^6$ groups. In some embodiments, each $R^{1A}$ is independently selected from the group consisting of halo, $C_{1-6}$ alkyl, $C_{1-6}$ haloalkyl, $C_{1-6}$ alkoxy, $C_{1-6}$ haloalkoxy, $NR^{N1}R^{N2}$, and $C_{6-10}$ aryl, wherein the $C_{1-6}$ alkyl, $C_{1-6}$ alkoxy, and $C_{6-10}$ aryl are each optionally substituted by 1 or 2 independently selected $R^6$ groups. In some embodiments, each $R^{1A}$ is independently selected from the group consisting of $C_{1-6}$ alkyl, $C_{1-6}$ alkoxy, $C_{1-6}$ haloalkoxy, $NR^{N1}R^{N2}$ and phenyl, wherein the $C_{1-6}$ alkyl, $C_{1-6}$ alkoxy, and phenyl are each optionally substituted by 1, 2, 3, or 4 independently selected $R^6$ groups. In some embodiments, each $R^{1A}$ is independently selected from the group consisting of $C_{1-6}$ alkyl, $C_{1-6}$ alkoxy, $C_{1-6}$ haloalkoxy, $NR^{N1}R^{N2}$ and phenyl, wherein the $C_{1-6}$ alkyl, $C_{1-6}$ alkoxy, and phenyl are each optionally substituted by 1 or 2 independently selected $R^6$ groups.

In some embodiments, each $R^{1A}$ is independently selected from the group consisting of methyl, —$CH_2CH_2OH$, —$OCH_2CH_2CH_2F$, —$OCH_2CH_2CH_2CH_2CH_2F$, —$OCH_2CH_2CH_2CH_2CH_2CH_2F$, —$OCH_2CH_2OCH_2CH_2F$, —$N(CH_2CH_3)_2$, —$N(CH_3)CH_2CH_2F$, and phenyl, wherein the phenyl is optionally substituted by $NO_2$, —$OCH_3$, —$OCH_2CH_2CH_2F$, and —$OCH_2CH_2OCH_2CH_2F$. In some embodiments, each $R^{1A}$ is independently selected from the group consisting of methyl, —$CH_2CH_2OH$, —$OCH_2CH_2CH_2F$, —$OCH_2CH_2CH_2CH_2CH_2{}^{18}F$, —$OCH_2CH_2CH_2CH_2CH_2CH_2{}^{18}F$, —$OCH_2CH_2OCH_2CH_2{}^{18}F$, —$N(CH_2CH_3)_2$, —$N(CH_3)CH_2CH_2{}^{18}F$, and phenyl, wherein the phenyl is optionally substituted by $NO_2$, —$OCH_3$, —$OCH_2CH_2CH_2{}^{18}F$, and —$OCH_2CH_2OCH_2CH_2{}^{18}F$.

In some embodiments, $R^2$ is selected from the group consisting of $C_{1-6}$ alkyl, $C_{3-10}$ cycloalkyl, $C_{6-10}$ aryl, 4-10 membered heterocycloalkyl, and 5-10 membered heteroaryl. In some embodiments, $R^2$ is selected from the group consisting of $C_{1-6}$ alkyl, $C_{3-10}$ cycloalkyl, and $C_{6-10}$ aryl each of which may be optionally substituted by 1, 2, 3, or 4 independently selected $R^{2A}$ groups. In some embodiments, $R^2$ is selected from the group consisting of $C_{1-6}$ alkyl, $C_{3-6}$ cycloalkyl, and phenyl, each of which may be optionally substituted by 1, 2, 3, or 4 independently selected $R^{2A}$ groups. In some embodiments, $R^2$ is selected from the group consisting of $C_{1-6}$ alkyl, $C_{3-10}$ cycloalkyl, and phenyl. In some embodiments, $R^2$ is selected from the group consisting of $C_{1-6}$ alkyl, cyclobutyl, adamantyl, and phenyl. In some embodiments, $R^2$ is selected from the group consisting of $C_{1-6}$ alkyl, $C_{3-6}$ cycloalkyl, and phenyl. In some embodiments, $R^2$ is selected from the group consisting of methyl, cyclobutyl, adamantyl, and phenyl. In some embodiments, $R^2$ is selected from the group consisting of methyl, cyclobutyl, and phenyl.

In some embodiments, $R^4$ and $R^5$ are each halo. In some embodiments, $R^4$ and $R^5$ are each fluoro.

In some embodiments, each $R^6$ is independently selected from the group consisting of OH, $NO_2$, $C_{1-6}$ alkyl, $C_{1-6}$ haloalkyl, $C_{1-6}$ alkoxy, $C_{1-6}$ haloalkoxy, and —($C_{1-6}$ alkoxy)-($C_{1-6}$ haloalkoxy). In some embodiments, each $R^6$ is independently selected from the group consisting of OH, $NO_2$, $C_{1-6}$ haloalkyl, $C_{1-6}$ alkoxy, $C_{1-6}$ haloalkoxy, and —($C_{1-6}$ alkoxy)-($C_{1-6}$ haloalkoxy). In some embodiments, each $R^6$ is independently selected from the group consisting of OH, $NO_2$, —$OCH_3$, —$CH_2F$, —$CH_2CH_2CH_2F$, and —$OCH_2CH_2OCH_2CH_2F$. In some embodiments, each $R^6$ is independently selected from the group consisting of OH, $NO_2$, —$OCH_3$, —$CH_2{}^{11}F$, —$CH_2CH_2CH_2{}^{18}F$, and —$OCH_2CH_2OCH_2CH_2{}^{18}F$.

In some embodiments, the compound of Formula I is a compound of Formula V:

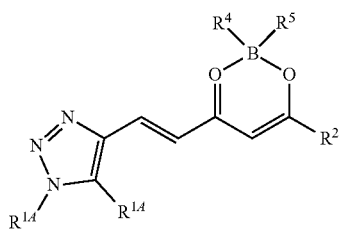

V a pharmaceutically acceptable salt thereof, or a tautomer thereof, wherein variables $R^{1A}$, $R^2$, $R^4$, and $R^5$ are defined according to the definitions provided herein for compounds of Formula I.

In some embodiments, each $R^{1A}$ is independently selected from the group consisting of halo, $C_{1-6}$ alkyl, $C_{1-6}$ haloalkyl, $C_{1-6}$ alkoxy, $C_{1-6}$ haloalkoxy, $NR^{N1}R^{N2}$ and $C_{6-10}$ aryl, wherein the $C_{1-6}$ alkyl, $C_{1-6}$ alkoxy, and $C_{6-10}$ aryl are each optionally substituted by 1, 2, 3, or 4 independently selected $R^6$ groups. In some embodiments, each $R^{1A}$ is independently selected from the group consisting of halo, $C_{1-6}$ alkyl, $C_{1-6}$ haloalkyl, $C_{1-6}$ alkoxy, $C_{1-6}$ haloalkoxy, $NR^{N1}R^{N2}$, and $C_{6-10}$ aryl, wherein the $C_{1-6}$ alkyl, $C_{1-6}$ alkoxy, and $C_{6-10}$ aryl are each optionally substituted by 1 or 2 independently selected $R^6$ groups. In some embodiments, each $R^{1A}$ is independently selected from the group consisting of $C_{1-6}$ alkyl, $C_{1-6}$ alkoxy, $C_{1-6}$ haloalkoxy, $NR^{N1}R^{N2}$ and phenyl, wherein the $C_{1-6}$ alkyl, $C_{1-6}$ alkoxy, and phenyl are each optionally substituted by 1, 2, 3, or 4 independently selected $R^6$ groups. In some embodiments, each $R^{1A}$ is independently selected from the group consisting of $C_{1-6}$ alkyl, $C_{1-6}$ alkoxy, $C_{1-6}$ haloalkoxy, $NR^{N1}R^{N2}$ and phenyl, wherein the $C_{1-6}$ alkyl, $C_{1-6}$ alkoxy, and phenyl are each optionally substituted by 1 or 2 independently selected $R^6$ groups.

In some embodiments, each $R^{1A}$ is independently selected from the group consisting of methyl, —$CH_2CH_2OH$, —$OCH_2CH_2CH_2F$, —$OCH_2CH_2CH_2CH_2CH_2F$, —$OCH_2CH_2CH_2CH_2CH_2CH_2CH_2F$, —$OCH_2CH_2OCH_2CH_2F$, —$N(CH_2CH_3)_2$, —$N(CH_3)CH_2CH_2F$, and phenyl, wherein the phenyl is optionally substituted by $NO_2$, —$OCH_3$, —$OCH_2CH_2CH_2F$, and —$OCH_2CH_2OCH_2CH_2F$. In some embodiments, each $R^{1A}$ is independently selected from the group consisting of methyl, —$CH_2CH_2OH$, —$OCH_2CH_2CH_2F$, —$OCH_2CH_2CH_2CH_2CH_2{}^{18}F$, —$OCH_2CH_2CH_2CH_2CH_2CH_2CH_2{}^{18}F$, —$OCH_2CH_2OCH_2CH_2{}^{18}F$, —$N(CH_2CH_3)_2$, —$N(CH_3)CH_2CH_2{}^{18}F$, and phenyl, wherein the phenyl is optionally substituted by $NO_2$, —$OCH_3$, —$OCH_2CH_2CH_2{}^{18}F$, and —$OCH_2CH_2OCH_2CH_2{}^{18}F$.

In some embodiments, $R^2$ is selected from the group consisting of $C_{1-6}$ alkyl, $C_{3-10}$ cycloalkyl, $C_{6-10}$ aryl, 4-10 membered heterocycloalkyl, and 5-10 membered heteroaryl. In some embodiments, $R^2$ is selected from the group consisting of $C_{1-6}$ alkyl, $C_{3-10}$ cycloalkyl, and $C_{6-10}$ aryl each of which may be optionally substituted by 1, 2, 3, or 4 independently selected $R^{2A}$ groups. In some embodiments, $R^2$ is selected from the group consisting of $C_{1-6}$ alkyl, $C_{3-6}$ cycloalkyl, and phenyl, each of which may be optionally substituted by 1, 2, 3, or 4 independently selected $R^{2A}$ groups. In some embodiments, $R^2$ is selected from the group consisting of $C_{1-6}$ alkyl, $C_{3-10}$ cycloalkyl, and phenyl. In some embodiments, $R^2$ is selected from the group consisting of $C_{1-6}$ alkyl, cyclobutyl, adamantyl, and phenyl. In some embodiments, $R^2$ is selected from the group consisting of $C_{1-6}$ alkyl, $C_{3-6}$ cycloalkyl, and phenyl. In some embodiments, $R^2$ is selected from the group consisting of methyl, cyclobutyl, adamantyl, and phenyl. In some embodiments, $R^2$ is selected from the group consisting of methyl, cyclobutyl, and phenyl.

In some embodiments, $R^4$ and $R^5$ are each halo. In some embodiments, $R^4$ and $R^5$ are each fluoro.

In some embodiments, each $R^6$ is independently selected from the group consisting of OH, $NO_2$, $C_{1-6}$ alkyl, $C_{1-6}$ haloalkyl, $C_{1-6}$ alkoxy, $C_{1-6}$ haloalkoxy, and —($C_{1-6}$ alkoxy)-($C_{1-6}$ haloalkoxy). In some embodiments, each $R^6$ is independently selected from the group consisting of OH, $NO_2$, $C_{1-6}$ haloalkyl, $C_{1-6}$ alkoxy, $C_{1-6}$ haloalkoxy, and —($C_{1-6}$ alkoxy)-($C_{1-6}$ haloalkoxy). In some embodiments, each $R^6$ is independently selected from the group consisting of OH, $NO_2$, —$OCH_3$, —$CH_2F$, —$CH_2CH_2CH_2F$, and —$OCH_2CH_2OCH_2CH_2F$. In some embodiments, each $R^6$ is independently selected from the group consisting of OH, $NO_2$, —$OCH_3$, —$CH_2{}^{11}F$, —$CH_2CH_2CH_2{}^{18}F$, and —$OCH_2CH_2OCH_2CH_2{}^{18}F$.

In some embodiments, the compound of Formula I is a compound of Formula VI:

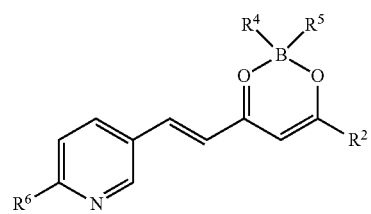

VI a pharmaceutically acceptable salt thereof, or a tautomer thereof, wherein variables $R^2$, $R^4$, $R^5$, and $R^6$ are defined according to the definitions provided herein for compounds of Formula I.

In some embodiments, each $R^{1A}$ is independently selected from the group consisting of halo, $C_{1-6}$ alkyl, $C_{1-6}$ haloalkyl, $C_{1-6}$ alkoxy, $C_{1-6}$ haloalkoxy, $NR^{N1}R^{N2}$ and $C_{6-10}$ aryl, wherein the $C_{1-6}$ alkyl, $C_{1-6}$ alkoxy, and $C_{6-10}$ aryl are each optionally substituted by 1, 2, 3, or 4 independently selected $R^6$ groups. In some embodiments, each $R^{1A}$ is independently selected from the group consisting of halo, $C_{1-6}$ alkyl, $C_{1-6}$ haloalkyl, $C_{1-6}$ alkoxy, $C_{1-6}$ haloalkoxy, $NR^{N1}R^{N2}$, and $C_{6-10}$ aryl, wherein the $C_{1-6}$ alkyl, $C_{1-6}$ alkoxy, and $C_{6-10}$ aryl are each optionally substituted by 1 or 2 independently selected $R^6$ groups. In some embodiments, each $R^{1A}$ is independently selected from the group consisting of $C_{1-6}$ alkyl, $C_{1-6}$ alkoxy, $C_{1-6}$ haloalkoxy, $NR^{N1}R^{N2}$ and phenyl, wherein the $C_{1-6}$ alkyl, $C_{1-6}$ alkoxy, and phenyl are each optionally substituted by 1, 2, 3, or 4 independently selected $R^6$ groups. In some embodiments, each $R^{1A}$ is independently selected from the group consisting of $C_{1-6}$ alkyl, $C_{1-6}$ alkoxy, $C_{1-6}$ haloalkoxy, $NR^{N1}R^{N2}$ and phenyl, wherein the $C_{1-6}$ alkyl, $C_{1-6}$ alkoxy, and phenyl are each optionally substituted by 1 or 2 independently selected $R^6$ groups.

In some embodiments, each $R^{1A}$ is independently selected from the group consisting of methyl, —$CH_2CH_2OH$, —$OCH_2CH_2CH_2F$, —$OCH_2CH_2CH_2CH_2CH_2F$, —$OCH_2CH_2CH_2CH_2CH_2CH_2F$, —$OCH_2CH_2OCH_2CH_2F$, —$N(CH_2CH_3)_2$, —$N(CH_3)CH_2CH_2F$, and phenyl, wherein the phenyl is optionally substituted by $NO_2$, —$OCH_3$, —$OCH_2CH_2CH_2F$, and —$OCH_2CH_2OCH_2CH_2F$. In some embodiments, each $R^{1A}$ is independently selected from the group consisting of methyl, —$CH_2CH_2OH$, —$OCH_2CH_2CH_2F$, —$OCH_2CH_2CH_2CH_2CH_2^{18}F$, —$OCH_2CH_2CH_2CH_2CH_2CH_2^{18}F$, —$OCH_2CH_2OCH_2CH_2^{18}F$, —$N(CH_2CH_3)_2$, —$N(CH_3)CH_2CH_2^{18}F$, and phenyl, wherein the phenyl is optionally substituted by $NO_2$, —$OCH_3$, —$OCH_2CH_2CH_2^{18}F$, and —$OCH_2CH_2OCH_2CH_2^{18}F$.

In some embodiments, $R^2$ is selected from the group consisting of $C_{1-6}$ alkyl, $C_{3-10}$ cycloalkyl, $C_{6-10}$ aryl, 4-10 membered heterocycloalkyl, and 5-10 membered heteroaryl. In some embodiments, $R^2$ is selected from the group consisting of $C_{1-6}$ alkyl, $C_{3-10}$ cycloalkyl, and $C_{6-10}$ aryl each of which may be optionally substituted by 1, 2, 3, or 4 independently selected $R^{2A}$ groups. In some embodiments, $R^2$ is selected from the group consisting of $C_{1-6}$ alkyl, $C_{3-6}$ cycloalkyl, and phenyl, each of which may be optionally substituted by 1, 2, 3, or 4 independently selected $R^{2A}$ groups. In some embodiments, $R^2$ is selected from the group consisting of $C_{1-6}$ alkyl, $C_{3-10}$ cycloalkyl, and phenyl. In some embodiments, $R^2$ is selected from the group consisting of $C_{1-6}$ alkyl, cyclobutyl, adamantyl, and phenyl. In some embodiments, $R^2$ is selected from the group consisting of $C_{1-6}$ alkyl, $C_{3-6}$ cycloalkyl, and phenyl. In some embodiments, $R^2$ is selected from the group consisting of methyl, cyclobutyl, adamantyl, and phenyl. In some embodiments, $R^2$ is selected from the group consisting of methyl, cyclobutyl, and phenyl.

In some embodiments, $R^4$ and $R^5$ are each halo. In some embodiments, $R^4$ and $R^5$ are each fluoro.

In some embodiments, each $R^6$ is independently selected from the group consisting of OH, $NO_2$, $C_{1-6}$ alkyl, $C_{1-6}$ haloalkyl, $C_{1-6}$ alkoxy, $C_{1-6}$ haloalkoxy, and —($C_{1-6}$ alkoxy)-($C_{1-6}$ haloalkoxy). In some embodiments, each $R^6$ is independently selected from the group consisting of OH, $NO_2$, $C_{1-6}$ haloalkyl, $C_{1-6}$ alkoxy, $C_{1-6}$ haloalkoxy, and —($C_{1-6}$ alkoxy)-($C_{1-6}$ haloalkoxy). In some embodiments, each $R^6$ is independently selected from the group consisting of OH, $NO_2$, —$OCH_3$, —$CH_2F$, —$CH_2CH_2CH_2F$, and —$OCH_2CH_2OCH_2CH_2F$. In some embodiments, each $R^6$ is independently selected from the group consisting of OH, $NO_2$, —$OCH_3$, —$CH_2^{18}F$, —$CH_2CH_2CH_2^{18}F$, and —$OCH_2CH_2OCH_2CH_2^{18}F$.

In some embodiments, the compound of Formula I is a compound of Formula VII:

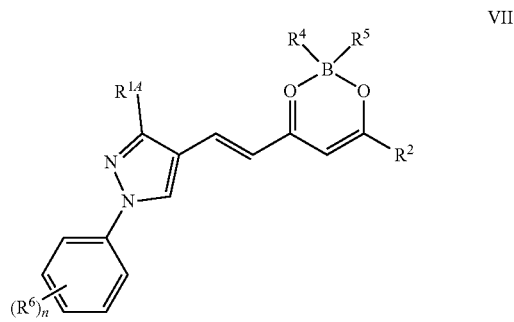

a pharmaceutically acceptable salt thereof, or a tautomer thereof, wherein n is 0 or 1, and variables $R^{1A}$, $R^2$, $R^4$, $R^5$, and $R^6$ are defined according to the definitions provided herein for compounds of Formula I.

In some embodiments, $R^{1A}$ is selected from the group consisting of H and $C_{1-6}$ alkyl.

In some embodiments, $R^2$ is selected from the group consisting of $C_{1-6}$ alkyl, $C_{3-10}$ cycloalkyl, $C_{6-10}$ aryl, 4-10 membered heterocycloalkyl, and 5-10 membered heteroaryl. In some embodiments, $R^2$ is selected from the group consisting of $C_{1-6}$ alkyl, $C_{3-10}$ cycloalkyl, and $C_{6-10}$ aryl each of which may be optionally substituted by 1, 2, 3, or 4 independently selected $R^{2A}$ groups. In some embodiments, $R^2$ is selected from the group consisting of $C_{1-6}$ alkyl, $C_{3-6}$ cycloalkyl, and phenyl, each of which may be optionally substituted by 1, 2, 3, or 4 independently selected $R^{2A}$ groups. In some embodiments, $R^2$ is selected from the group consisting of $C_{1-6}$ alkyl, $C_{3-10}$ cycloalkyl, and phenyl. In some embodiments, $R^2$ is selected from the group consisting of $C_{1-6}$ alkyl, cyclobutyl, adamantyl, and phenyl. In some embodiments, $R^2$ is selected from the group consisting of $C_{1-6}$ alkyl, $C_{3-6}$ cycloalkyl, and phenyl. In some embodiments, $R^2$ is selected from the group consisting of methyl, cyclobutyl, adamantyl, and phenyl. In some embodiments, $R^2$ is selected from the group consisting of methyl, cyclobutyl, and phenyl.

In some embodiments, each $R^6$ is independently selected from the group consisting of OH, $NO_2$, $C_{1-6}$ alkyl, $C_{1-6}$ haloalkyl, $C_{1-6}$ alkoxy, $C_{1-6}$ haloalkoxy, and —($C_{1-6}$ alkoxy)-($C_{1-6}$ haloalkoxy). In some embodiments, each $R^6$ is independently selected from the group consisting of OH, $NO_2$, $C_{1-6}$ haloalkyl, $C_{1-6}$ alkoxy, $C_{1-6}$ haloalkoxy, and —($C_{1-6}$ alkoxy)-($C_{1-6}$ haloalkoxy). In some embodiments, each $R^6$ is independently selected from the group consisting of OH, $NO_2$, —$OCH_3$, —$CH_2F$, —$CH_2CH_2CH_2F$, and —$OCH_2CH_2OCH_2CH_2F$. In some embodiments, each $R^6$ is independently selected from the group consisting of OH, $NO_2$, —$OCH_3$, —$CH_2^{18}F$, —$CH_2CH_2CH_2^{18}F$, and —$OCH_2CH_2OCH_2CH_2^{18}F$.

In some embodiments, the compound of Formula I is a compound of Formula VIII:

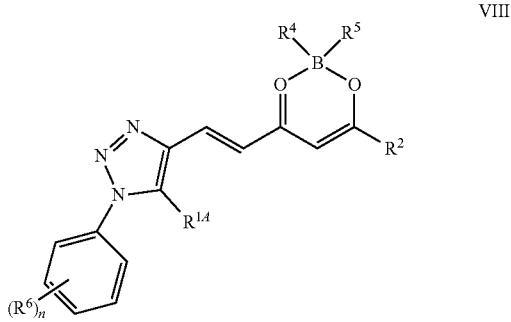

VIII

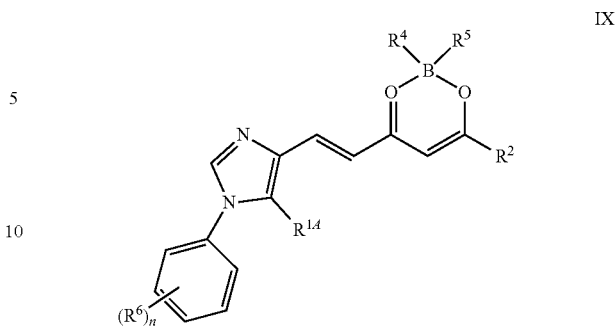

IX a pharmaceutically acceptable salt thereof, or a tautomer thereof, wherein n is 0 or 1, and variables $R^{1A}$, $R^2$, $R^4$, $R^5$, and $R^6$ are defined according to the definitions provided herein for compounds of Formula I.

In some embodiments, $R^{1A}$ is selected from the group consisting of H and $C_{1-6}$ alkyl.

In some embodiments, $R^2$ is selected from the group consisting of $C_{1-6}$ alkyl, $C_{3-10}$ cycloalkyl, $C_{6-10}$ aryl, 4-10 membered heterocycloalkyl, and 5-10 membered heteroaryl. In some embodiments, $R^2$ is selected from the group consisting of $C_{1-6}$ alkyl, $C_{3-10}$ cycloalkyl, and $C_{6-10}$ aryl each of which may be optionally substituted by 1, 2, 3, or 4 independently selected $R^{2A}$ groups. In some embodiments, $R^2$ is selected from the group consisting of $C_{1-6}$ alkyl, $C_{3-6}$ cycloalkyl, and phenyl, each of which may be optionally substituted by 1, 2, 3, or 4 independently selected $R^{2A}$ groups. In some embodiments, $R^2$ is selected from the group consisting of $C_{1-6}$ alkyl, $C_{3-10}$ cycloalkyl, and phenyl. In some embodiments, $R^2$ is selected from the group consisting of $C_{1-6}$ alkyl, cyclobutyl, adamantyl, and phenyl. In some embodiments, $R^2$ is selected from the group consisting of $C_{1-6}$ alkyl, $C_{3-6}$ cycloalkyl, and phenyl. In some embodiments, $R^2$ is selected from the group consisting of methyl, cyclobutyl, adamantyl, and phenyl. In some embodiments, $R^2$ is selected from the group consisting of methyl, cyclobutyl, and phenyl.

In some embodiments, each $R^6$ is independently selected from the group consisting of OH, $NO_2$, $C_{1-6}$ alkyl, $C_{1-6}$ haloalkyl, $C_{1-6}$ alkoxy, $C_{1-6}$ haloalkoxy, and —($C_{1-6}$ alkoxy)-($C_{1-6}$ haloalkoxy). In some embodiments, each $R^6$ is independently selected from the group consisting of OH, $NO_2$, $C_{1-6}$ haloalkyl, $C_{1-6}$ alkoxy, $C_{1-6}$ haloalkoxy, and —($C_{1-6}$ alkoxy)-($C_{1-6}$ haloalkoxy). In some embodiments, each $R^6$ is independently selected from the group consisting of OH, $NO_2$, —$OCH_3$, —$CH_2F$, —$CH_2CH_2CH_2F$, and —$OCH_2CH_2OCH_2CH_2F$. In some embodiments, each $R^6$ is independently selected from the group consisting of OH, $NO_2$, —$OCH_3$, —$CH_2{}^{18}F$, —$CH_2CH_2CH_2{}^{18}F$, and —$OCH_2CH_2OCH_2CH_2{}^{18}F$.

In some embodiments, the compound of Formula I is a compound of Formula IX:

a pharmaceutically acceptable salt thereof, or a tautomer thereof, wherein n is 0 or 1, and variables $R^{1A}$, $R^2$, $R^4$, $R^5$, and $R^6$ are defined according to the definitions provided herein for compounds of Formula I.

In some embodiments, $R^{1A}$ is selected from the group consisting of H and $C_{1-6}$ alkyl.

In some embodiments, $R^2$ is selected from the group consisting of $C_{1-6}$ alkyl, $C_{3-10}$ cycloalkyl, $C_{6-10}$ aryl, 4-10 membered heterocycloalkyl, and 5-10 membered heteroaryl. In some embodiments, $R^2$ is selected from the group consisting of $C_{1-6}$ alkyl, $C_{3-10}$ cycloalkyl, and $C_{6-10}$ aryl each of which may be optionally substituted by 1, 2, 3, or 4 independently selected $R^{2A}$ groups. In some embodiments, $R^2$ is selected from the group consisting of $C_{1-6}$ alkyl, $C_{3-6}$ cycloalkyl, and phenyl, each of which may be optionally substituted by 1, 2, 3, or 4 independently selected $R^{2A}$ groups. In some embodiments, $R^2$ is selected from the group consisting of $C_{1-6}$ alkyl, $C_{3-10}$ cycloalkyl, and phenyl. In some embodiments, $R^2$ is selected from the group consisting of $C_{1-6}$ alkyl, cyclobutyl, adamantyl, and phenyl. In some embodiments, $R^2$ is selected from the group consisting of $C_{1-6}$ alkyl, $C_{3-6}$ cycloalkyl, and phenyl. In some embodiments, $R^2$ is selected from the group consisting of methyl, cyclobutyl, adamantyl, and phenyl. In some embodiments, $R^2$ is selected from the group consisting of methyl, cyclobutyl, and phenyl.

In some embodiments, each $R^6$ is independently selected from the group consisting of OH, $NO_2$, $C_{1-6}$ alkyl, $C_{1-6}$ haloalkyl, $C_{1-6}$ alkoxy, $C_{1-6}$ haloalkoxy, and —($C_{1-6}$ alkoxy)-($C_{1-6}$ haloalkoxy). In some embodiments, each $R^6$ is independently selected from the group consisting of OH, $NO_2$, $C_{1-6}$ haloalkyl, $C_{1-6}$ alkoxy, $C_{1-6}$ haloalkoxy, and —($C_{1-6}$ alkoxy)-($C_{1-6}$ haloalkoxy). In some embodiments, each $R^6$ is independently selected from the group consisting of OH, $NO_2$, —$OCH_3$, —$CH_2F$, —$CH_2CH_2CH_2F$, and —$OCH_2CH_2OCH_2CH_2F$. In some embodiments, each $R^6$ is independently selected from the group consisting of OH, $NO_2$, —$OCH_3$, —$CH_2{}^{18}F$, —$CH_2CH_2CH_2{}^{18}F$, and —$OCH_2CH_2OCH_2CH_2{}^{18}F$.

Unless specifically defined, compounds and salts provided herein can also include all isotopes of atoms occurring in the intermediates or final compounds. Isotopes include those atoms having the same atomic number but different mass numbers.

In some embodiments, a compound provided herein (e.g., a compound of any of Formulas I-IX), a pharmaceutically acceptable salt thereof, or a tautomer thereof, comprises at least one radioisotope. As used herein, the term "radioisotope" refers to an atom having an atomic mass or mass number different from the atomic mass or mass number typically found in nature (i.e., naturally occurring). A "radiolabeled" compound is a compound provided herein where one or more atoms are replaced or substituted by an atom having an atomic mass or mass number different from the atomic mass or mass number typically found in nature (i.e., naturally occurring). Example radioisotopes include, but are not limited to, $^{11}$C, $^{13}$N, $^{15}$O, $^{18}$F, $^{34m}$Cl, $^{38}$K, $^{45}$Ti, $^{51}$Mn, $^{52m}$Mn, $^{52}$Fe, $^{55}$Co, $^{60}$Cu, $^{61}$Cu, $^{62}$Cu, $^{64}$Cu, $^{66}$Ga, $^{67}$Ga, $^{68}$Ga, $^{71}$As, $^{72}$As, $^{74}$As, $^{75}$Br, $^{76}$Br, $^{82}$Rb, $^{86}$Y, $^{89}$Zr, $^{90}$N, $^{94m}$Tc, $^{99m}$Tc, $^{110m}$In, $^{111}$In, $^{118}$Sb, $^{120}$I, $^{121}$I, $^{122}$I, $^{123}$I, $^{124}$I, $^{124}$I, $^{131}$I, and $^{201}$Tl.

In some embodiments, the compound provided herein, a pharmaceutically acceptable salt thereof, or a tautomer thereof, comprises at least one radioisotope selected from the group consisting of $^{11}$C, $^{13}$N, $^{15}$O, $^{18}$F, $^{68}$Ga, $^{89}$Zr, $^{82}$Rb, $^{124}$I, and $^{131}$I. In some embodiments, the radioisotope is a positron emitter. As used herein the term "positron emitter" refers to a radioisotope wherein a proton is converted to a neutron, thereby releasing a positron and an electron neutrino. In some embodiments, the positron emitter is $^{11}$C or $^{18}$F. In some embodiments, the compound provided herein, a pharmaceutically acceptable salt thereof, or a tautomer thereof, comprises at least one $^{18}$F radioisotope. In some embodiments at least one halo group of a compound provided herein is $^{18}$F. In some embodiments, at least one halo, haloalkyl, fluoroalkyl, or haloalkoxy group of a compound provided herein comprises at least one radioisotope. In some embodiments, at least one haloalkyl, fluoroalkyl, or haloalkoxy group of a compound provided herein comprises at least one $^{18}$F radioisotope.

In some embodiments, at least one $R^{1A}$ group comprises at least one radioisotope. In some embodiments, one $R^{1A}$ group comprises one radioisotope. In some embodiments, one $R^{1A}$ group comprises one $^{18}$F group.

In some embodiments, at least one $R^{2A}$ group comprises at least one radioisotope. In some embodiments, one $R^{2A}$ group comprises one radioisotope. In some embodiments, one $R^{2A}$ group comprises one $^{18}$F group.

In some embodiments, $R^3$ comprises at least one radioisotope. In some embodiments, $R^3$ comprises one radioisotope. In some embodiments, $R^3$ comprises one $^{18}$F group.

In some embodiments, $R^4$ is a radioisotope. In some embodiments, $R^4$ is $^{18}$F. In some embodiments, $R^5$ is a radioisotope. In some embodiments, $R^5$ is $^{18}$F.

In some embodiments, at least one $R^6$ group comprises at least one radioisotope. In some embodiments, one $R^6$ group comprises one radioisotope. In some embodiments, one $R^6$ group comprises one $^{18}$F group.

In some embodiments, at least one $R^{N2}$ group comprises at least one radioisotope. In some embodiments, one $R^{N2}$ group comprises one radioisotope. In some embodiments, one $R^{N2}$ group comprises one $^{18}$F group.

In some embodiments, the compound provided herein is selected from the group consisting of:

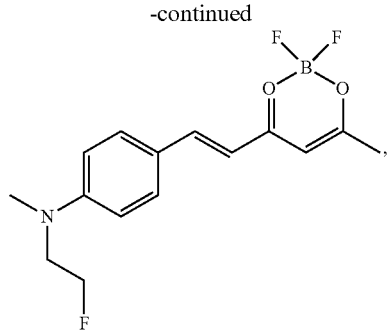

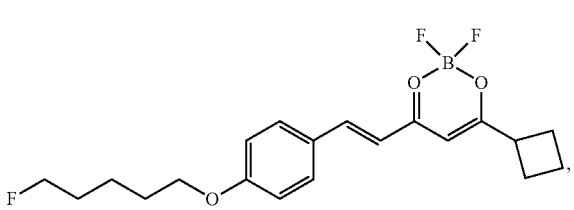

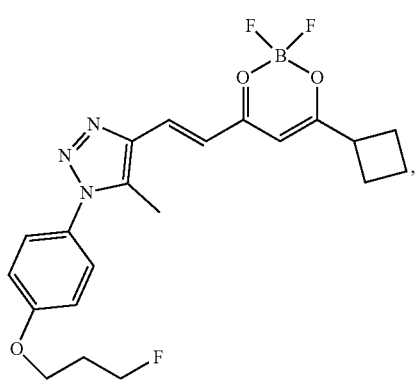

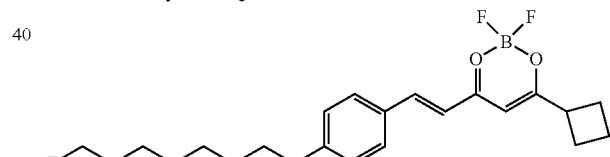

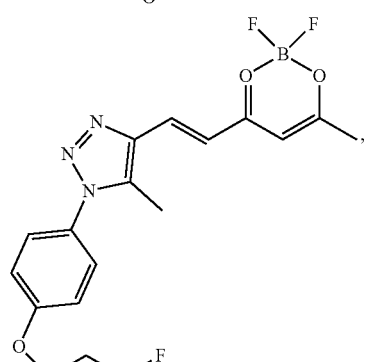

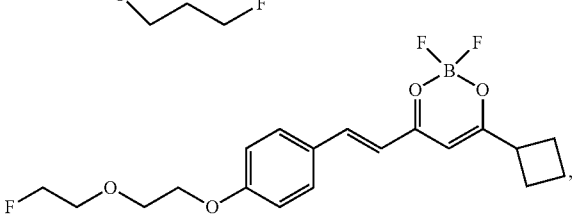

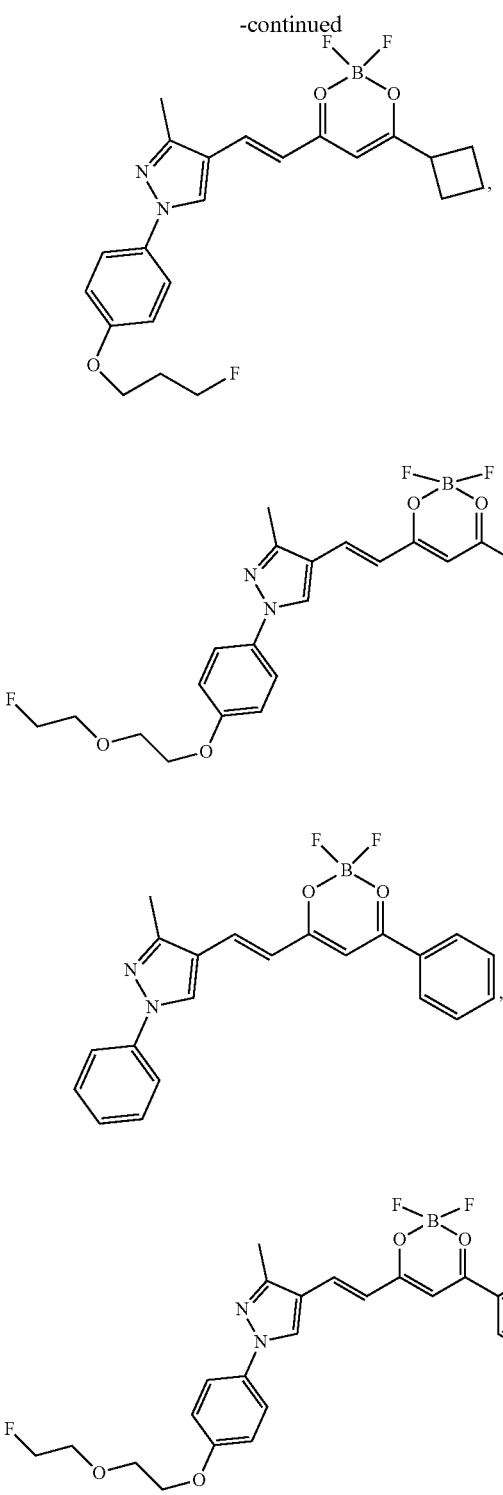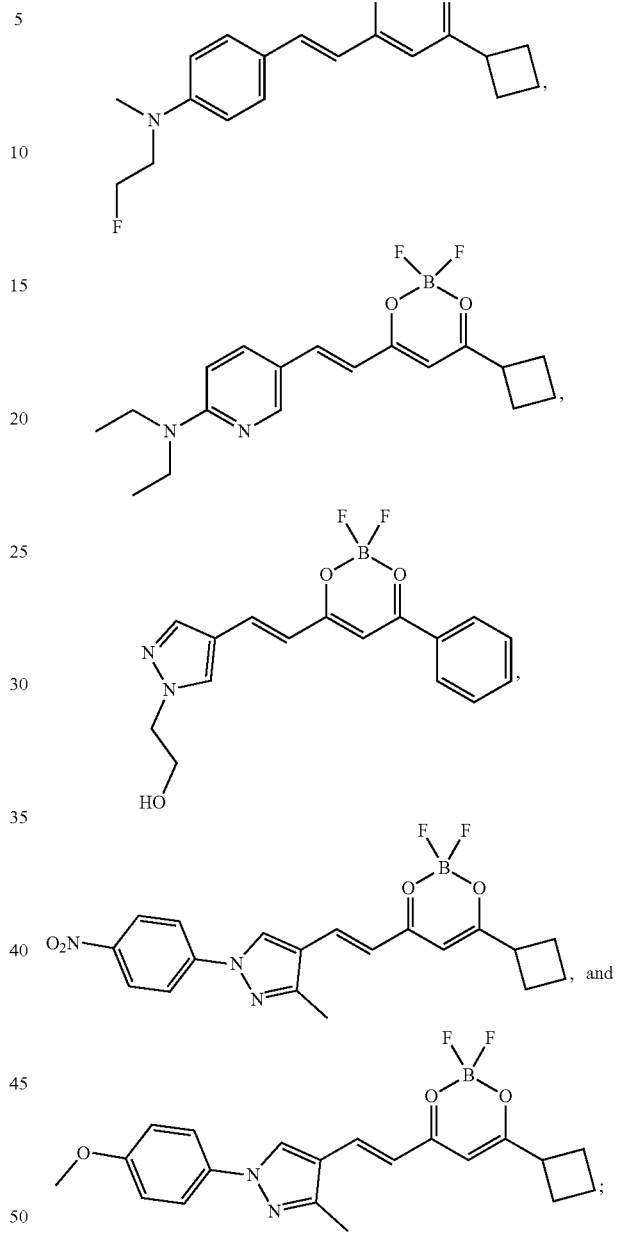
a pharmaceutically acceptable salt thereof, or a tautomer thereof.
In some embodiments, the compound provided herein is selected from the group consisting of:
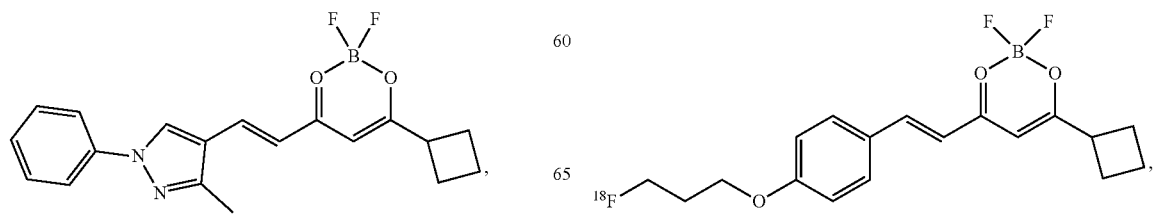

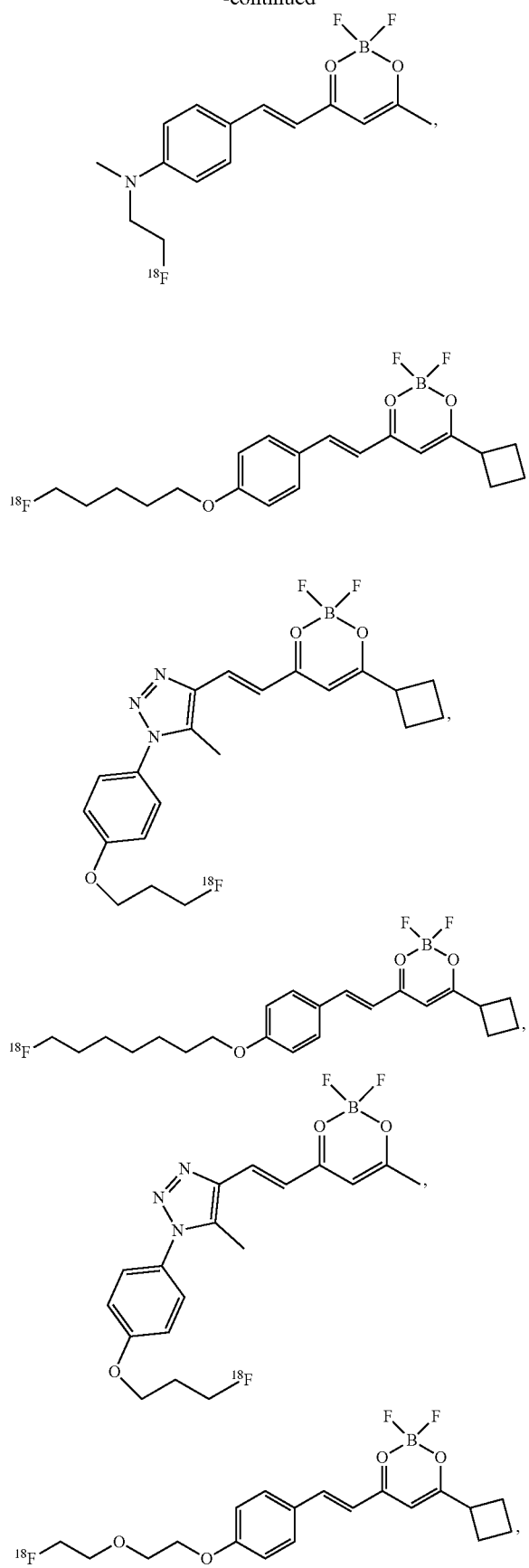
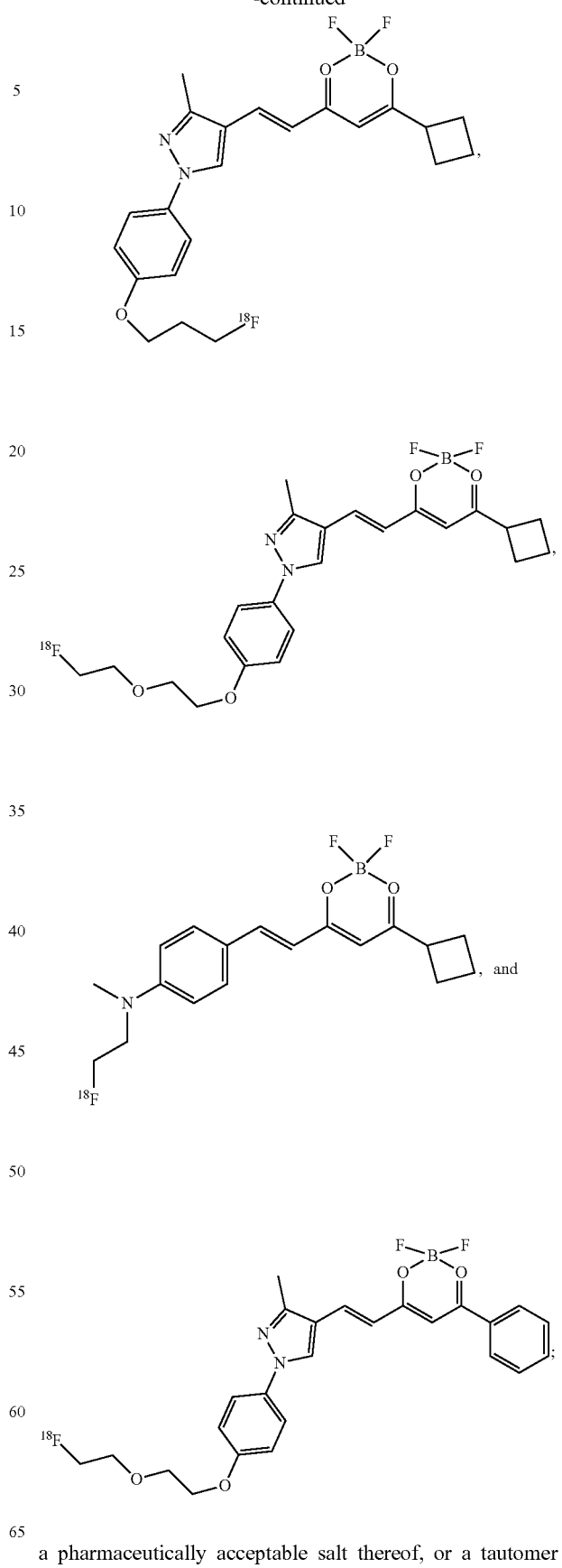
a pharmaceutically acceptable salt thereof, or a tautomer thereof.

In some embodiments, the compound provided herein is:

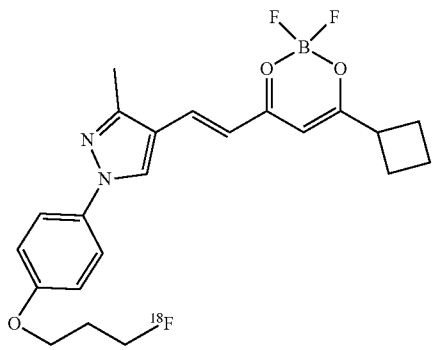

a pharmaceutically acceptable salt thereof, or a tautomer thereof.

Unless otherwise stated, when an atom is designated as an isotope or radioisotope (e.g., deuterium, $^{11}$C, $^{18}$F), the atom is understood to comprise the isotope or radioisotope in an amount at least greater than the natural abundance of the isotope or radioisotope. For example, when an atom is designated as "D" or "deuterium", the position is understood to have deuterium at an abundance that is at least 3000 times greater than the natural abundance of deuterium, which is 0.015% (i.e., at least 45% incorporation of deuterium).

As used herein, the term "Ci", refers to "Curie", a unit of radioactivity.

As used herein, the term "specific activity" refers to the activity of a given radioisotope per unit mass, for example, Ci/g.

Synthesis

As will be appreciated, the compounds provided herein, including salts thereof, can be prepared using known organic synthesis techniques and can be synthesized according to any of numerous possible synthetic routes.

The compounds provided herein (e.g., compounds of any of Formulas I-IX) can be prepared, for example, according to the procedure shown in Scheme 1. For example, reaction of an appropriately substituted acetylacetone with and appropriately substituted boron etherate compound (e.g. $BF_3.O(C_2H_5)_2$) affords a boronate-diketone (e.g., Intermediate 1), which can be further reacted with an appropriately substituted aldehyde (e.g., in the presence of 1,2,3,4-tetrahydroisoquinoline, AcOH, and a solvent such as acetonitrile) to form a compound of Formula I.

Scheme 1.

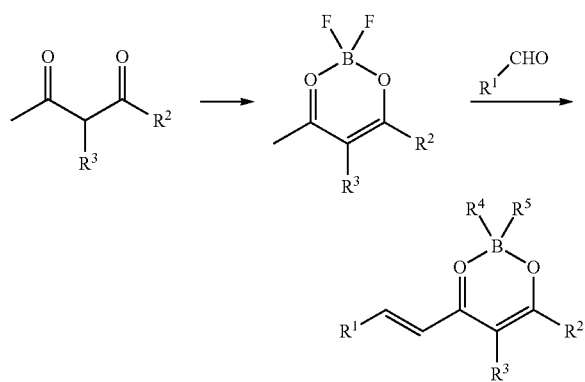

The compounds provided herein (e.g., compounds of any of Formulas I-IX) can also be prepared, for example, according to the procedure shown in Scheme 2. For example, compound (i) is reacted with an appropriately substituted boronate-diketone (e.g., Intermediate 1, in the presence of 1,2,3,4-tetrahydroisoquinoline, AcOH, and a solvent such as acetonitrile) to form a compound of Formula I.

Scheme 2.

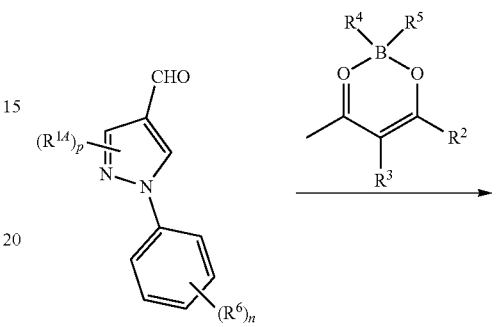

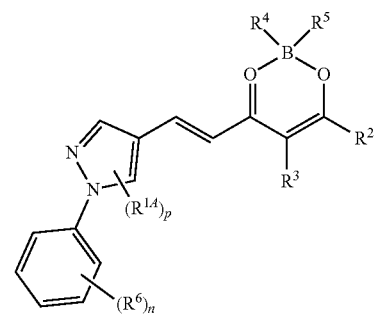

The compounds provided herein (e.g., compounds of any of Formulas I-IX) can also be prepared, for example, according to the procedures shown in Schemes 3-4. For example, a methoxy group of compound (i) is reacted in the presence of a demethylating agent (e.g., $BBr_3$) to form hydroxyl compound (ii), which can be further reacted with an appropriately substituted hydroxyl compound (e.g., 3-iodopropan-1-ol) to form compound (iii). Subsequent reaction of the hydroxyl group (e.g., via reaction with a suitable leaving group such as 4-methylbenzene-1-sulfonyl chloride (i.e., tosyl chloride, —OTs), affords compound (iv) (where LG is the leaving group), which can be further reacted with a nucleophile (e.g., fluoride) to form compound (v), which is then reacted according to the procedures shown in Scheme 2 to afford the desired compound (vi), where n is an integer from 0 to 4, p is an integer from 1 to 2, and variables $R^{14}$, $R^2$, $R^3$, $R^4$, and $R^5$ are defined according to the definitions provided herein for compounds of Formula I.

Scheme 3.
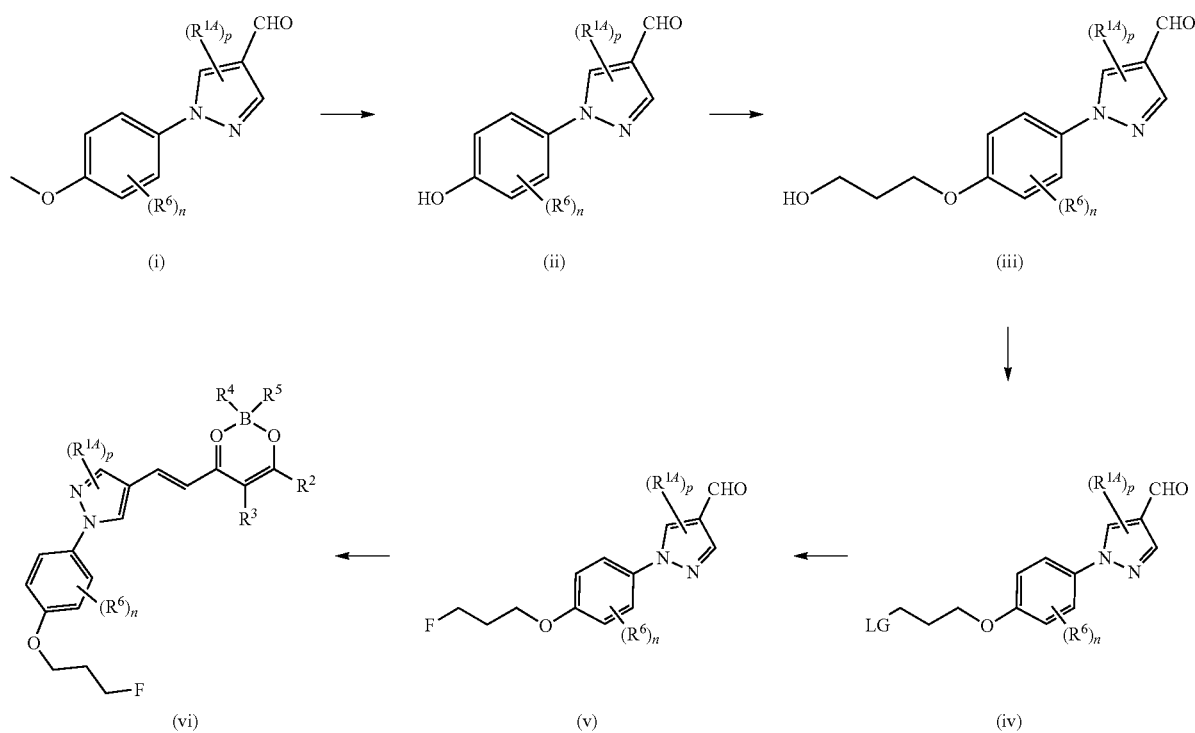
Scheme 4.
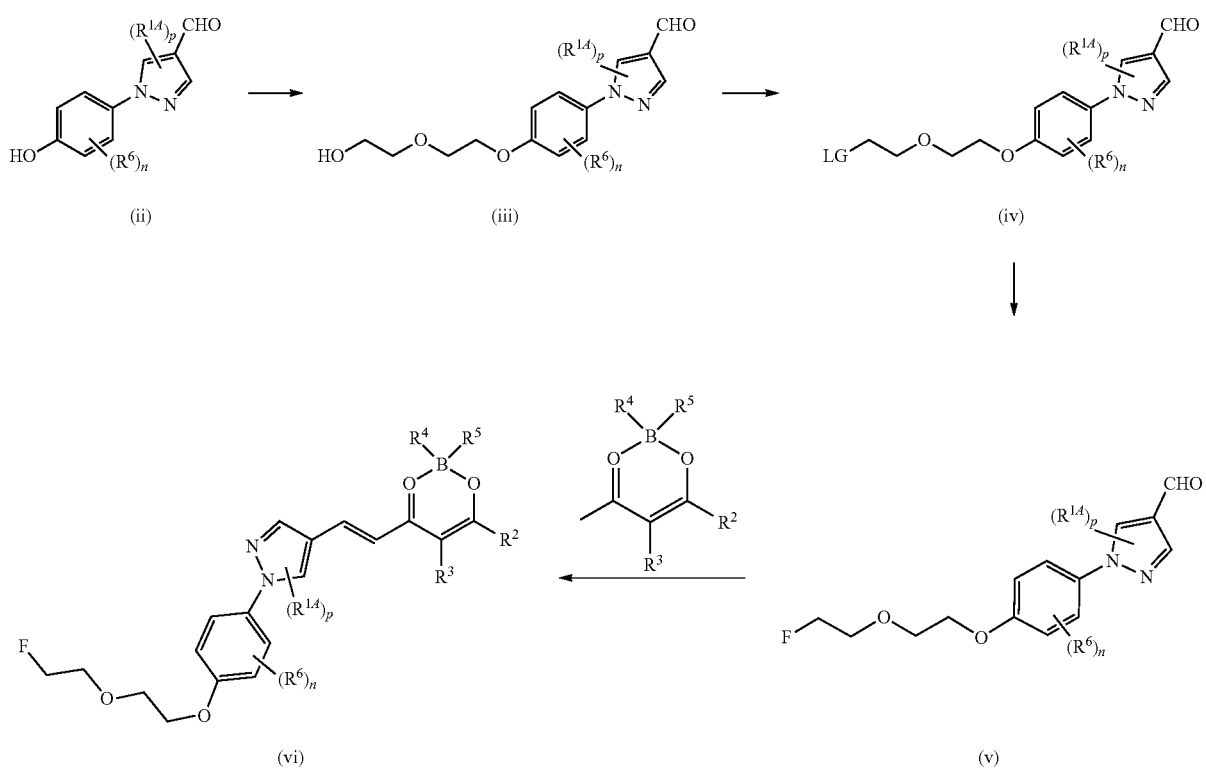

The radiolabeled compounds provided herein (e.g., a radiolabeled compound of any of Formulas I-IX) can also be prepared according to any of Schemes 1-4 using appropriately radiolabeled starting materials, or, alternatively, according to the procedure shown in Scheme 5. For example, a compound (i) having an appropriate leaving group (LG) (e.g. a tosylate or mesylate group) can be reacted with a $^{18}$F-source (e.g., tetraethylammonium bicarbonate $^{18}$fluoride) to afford the radiolabeled aldehyde (ii), which is then reacted according to the procedures shown in Scheme 2 to afford the desired compound (iii), where variables $R^{N1}$, $R^1$, $R^2$, $R^3$, $R^4$, and $R^5$ are defined according to the definitions provided herein for compounds of Formula I.

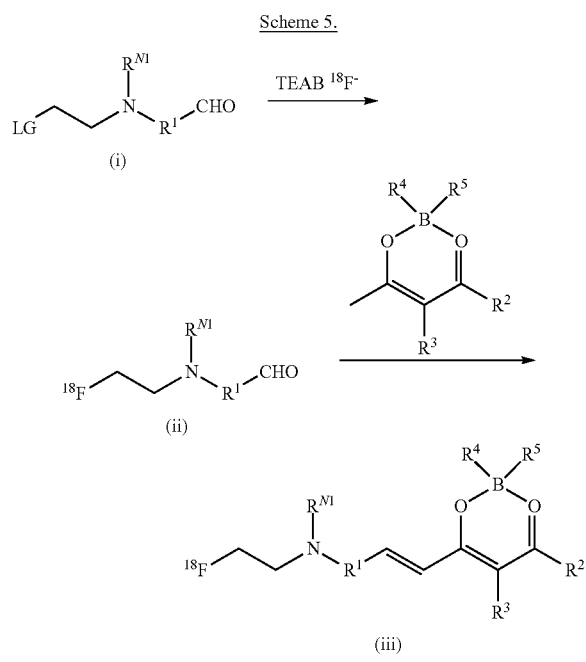

Scheme 5.

The radiolabeled compounds provided herein can also be prepared, for example, according to the procedure shown in Scheme 6, wherein a boronate-diketone substituted with an appropriate leaving group (LG) (e.g., a tosylate or mesylate group) can be reacted with a $^{18}$F-source (e.g., tetraethylammonium bicarbonate $^{18}$fluoride) to afford the desired compound (ii), where variables $R^{N1}$, $R^1$, $R^2$, $R^3$, $R^4$, and $R^5$ are defined according to the definitions provided herein for compounds of Formula I.

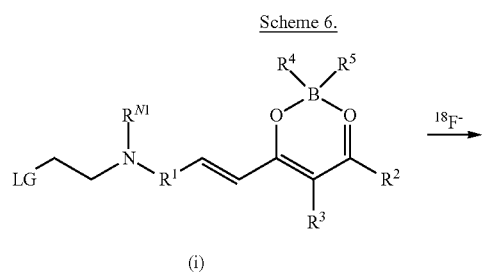

Scheme 6.

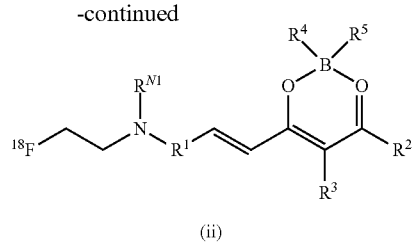

It will be appreciated by one skilled in the art that the processes described are not the exclusive means by which compounds provided herein may be synthesized and that a broad repertoire of synthetic organic reactions is available to be potentially employed in synthesizing compounds provided herein. The person skilled in the art knows how to select and implement appropriate synthetic routes. Suitable synthetic methods of starting materials, intermediates and products may be identified by reference to the literature, including reference sources such as: *Advances in Heterocyclic Chemistry*, Vols. 1-107 (Elsevier, 1963-2012); *Journal of Heterocyclic Chemistry* Vols. 1-49 (Journal of Heterocyclic Chemistry, 1964-2012); Carreira, et al. (Ed.) *Science of Synthesis*, Vols. 1-48 (2001-2010) and Knowledge Updates KU2010/1-4; 2011/1-4; 2012/1-2 (Thieme, 2001-2012); Katritzky, et al. (Ed.) *Comprehensive Organic Functional Group Transformations*, (Pergamon Press, 1996); Katritzky et al. (Ed.); *Comprehensive Organic Functional Group Transformations II* (Elsevier, 2$^{nd}$ Edition, 2004); Katritzky et al. (Ed.), *Comprehensive Heterocyclic Chemistry* (Pergamon Press, 1984); Katritzky et al., *Comprehensive Heterocyclic Chemistry II*, (Pergamon Press, 1996); Smith et al., *March's Advanced Organic Chemistry*: Reactions, Mechanisms, and Structure, 6$^{th}$ Ed. (Wiley, 2007); Trost et al. (Ed.), *Comprehensive Organic Synthesis* (Pergamon Press, 1991).

Preparation of compounds described herein can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, *Protective Groups in Organic Synthesis, 3$^{rd}$* Ed., Wiley & Sons, Inc., New York (1999).

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high performance liquid chromatography (HPLC), liquid chromatography-mass spectroscopy (LCMS), or thin layer chromatography (TLC). Compounds can be purified by those skilled in the art by a variety of methods, including high performance liquid chromatography (HPLC) and normal phase silica chromatography.

At various places in the present specification, divalent linking substituents are described. It is specifically intended that each divalent linking substituent include both the forward and backward forms of the linking substituent. For example, —NR(CR'R")$_n$-includes both —NR(CR'R")$_n$— and —(CR'R")$_n$NR—. Where the structure clearly requires a linking group, the Markush variables listed for that group are understood to be linking groups.

As used herein, the phrase "optionally substituted" means unsubstituted or substituted. As used herein, the term "substituted" means that a hydrogen atom is removed and replaced by a substituent. It is to be understood that substitution at a given atom is limited by valency.

Throughout the definitions, the term "$C_{n-m}$" indicates a range which includes the endpoints, wherein n and m are integers and indicate the number of carbons. Examples include $C_{1-4}$, $C_{1-6}$, and the like.

As used herein, the term "$C_{n-m}$ alkyl", employed alone or in combination with other terms, refers to a saturated hydrocarbon group that may be straight-chain or branched, having n to m carbons. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl, and the like. In some embodiments, the alkyl group contains from 1 to 6 carbon atoms, from 1 to 4 carbon atoms, from 1 to 3 carbon atoms, or 1 to 2 carbon atoms.

As used herein, "$C_{n-m}$ alkenyl" refers to an alkyl group having one or more double carbon-carbon bonds and having n to m carbons. Example alkenyl groups include, but are not limited to, ethenyl, n-propenyl, isopropenyl, n-butenyl, sec-butenyl, and the like. In some embodiments, the alkenyl moiety contains 2 to 6, 2 to 4, or 2 to 3 carbon atoms.

As used herein, "$C_{n-m}$ alkynyl" refers to an alkyl group having one or more triple carbon-carbon bonds and having n to m carbons. Example alkynyl groups include, but are not limited to, ethynyl, propyn-1-yl, propyn-2-yl, and the like. In some embodiments, the alkynyl moiety contains 2 to 6, 2 to 4, or 2 to 3 carbon atoms.

As used herein, the term "$C_{n-m}$ alkoxy", employed alone or in combination with other terms, refers to a group of formula —O-alkyl, wherein the alkyl group has n to m carbons. Example alkoxy groups include methoxy, ethoxy, propoxy (e.g., n-propoxy and isopropoxy), tert-butoxy, and the like. In some embodiments, the alkyl group has 1 to 6, 1 to 4, or 1 to 3 carbon atoms.

As used herein, the term "aryl," employed alone or in combination with other terms, refers to an aromatic hydrocarbon group, which may be monocyclic or polycyclic (e.g., having 2, 3 or 4 fused rings). The term "$C_{n-m}$ aryl" refers to an aryl group having from n to m ring carbon atoms. Aryl groups include, e.g., phenyl, naphthyl, anthracenyl, phenanthrenyl, indanyl, indenyl, and the like. In some embodiments, aryl groups have from 6 to about 20 carbon atoms, from 6 to about 15 carbon atoms, or from 6 to about 10 carbon atoms. In some embodiments, the aryl group is a substituted or unsubstituted phenyl.

As used herein, "halo" refers to F, Cl, Br, or I. In some embodiments, the halo is F, Cl, or Br. In some embodiments, the halo is F. In some embodiments, the halo is $^{18}$F.

As used herein, the term "$C_{n-m}$ haloalkyl", employed alone or in combination with other terms, refers to an alkyl group having from one halogen atom to 2s+1 halogen atoms which may be the same or different, where "s" is the number of carbon atoms in the alkyl group, wherein the alkyl group has n to m carbon atoms. In some embodiments, the haloalkyl group is fluorinated only (e.g, a $C_{1-6}$ fluoroalkyl group). In some embodiments, the alkyl group has 1 to 6, 1 to 4, or 1 to 3 carbon atoms. In some embodiments, the haloalkyl group comprises one or more $^{18}$F radioisotope. In some embodiments, the haloalkyl group comprises one $^{18}$F radioisotope.

As used herein, "$C_{n-m}$ haloalkoxy" refers to a group of formula —O-haloalkyl having n to m carbon atoms. An example haloalkoxy group is $OCF_3$. In some embodiments, the haloalkoxy group is fluorinated only. In some embodiments, the haloalkoxy group has 1 to 6, 1 to 4, or 1 to 3 carbon atoms. In some embodiments, the haloalkoxy group comprises one or more $^{18}$F radioisotopes. In some embodiments, the haloalkoxy group comprises one $^{18}$F radioisotope.

As used herein, "cycloalkyl" refers to non-aromatic cyclic hydrocarbons including cyclized alkyl and/or alkenyl groups. Cycloalkyl groups can include mono- or polycyclic (e.g., having 2, 3 or 4 fused rings) groups and spirocycles. Cycloalkyl groups can have 3, 4, 5, 6, 7, 8, 9, or 10 ring-forming carbons ($C_{3-10}$). Ring-forming carbon atoms of a cycloalkyl group can be optionally substituted by oxo or sulfido (e.g., C(O) or C(S)). Cycloalkyl groups also include cycloalkylidenes. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, and the like. In some embodiments, cycloalkyl is cyclopropyl, cyclobutyl, cyclopentyl, cyclohexyl, cyclopentyl, or adamantyl. In some embodiments, the cycloalkyl has 6-10 ring-forming carbon atoms (e.g., a $C_{6-10}$ cycloalkyl group). In some embodiments, cycloalkyl is adamantyl. In some embodiments, the cycloalkyl has 3-6 ring-forming carbon atoms (e.g., a $C_{3-6}$ cycloalkyl). Also included in the definition of cycloalkyl are moieties that have one or more aromatic rings fused (i.e., having a bond in common with) to the cycloalkyl ring, for example, benzo or thienyl derivatives of cyclopentane, cyclohexane, and the like. A cycloalkyl group containing a fused aromatic ring can be attached through any ring-forming atom including a ring-forming atom of the fused aromatic ring.

As used herein, the term "heteroaryl" refers to a monocyclic aromatic heterocycle having at least one heteroatom ring member selected from sulfur, oxygen, and nitrogen. In some embodiments, the heteroaryl ring has 1, 2, 3, or 4 heteroatom ring members independently selected from nitrogen, sulfur and oxygen. In some embodiments, the heteroaryl ring has 1, 2, 3, or 4 heteroatom ring members independently selected from nitrogen and sulfur. In some embodiments, any ring-forming N in a heteroaryl moiety can form an N-oxide. In some embodiments, the heteroaryl has 5-6 ring atoms and 1, 2, 3, or 4 heteroatom ring members independently selected from nitrogen, sulfur and oxygen. In some embodiments, the heteroaryl has 5-6 ring atoms and 1, 2, 3, or 4 heteroatom ring members independently selected from nitrogen and sulfur. In some embodiments, the heteroaryl has 5-6 ring atoms and 1 or 2 heteroatom ring members independently selected from nitrogen and sulfur. Exemplary five-membered ring heteroaryl groups include, but are not limited to, thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl. Exemplary six-membered ring heteroaryl groups include, but are not limited to, pyridyl, pyrazinyl, pyrimidinyl, triazinyl and pyridazinyl.

As used herein, "heterocycloalkyl" refers to non-aromatic monocyclic or polycyclic heterocycles having one or more ring-forming heteroatoms selected from O, N, or S. Included in heterocycloalkyl are monocyclic 4-, 5-, 6-, and 7-membered heterocycloalkyl groups. Heterocycloalkyl groups can also include spirocycles. Example heterocycloalkyl groups include pyrrolidin-2-one, 1,3-isoxazolidin-2-one, pyranyl, tetrahydropuran, oxetanyl, azetidinyl, morpholino, thiomorpholino, piperazinyl, tetrahydrofuranyl, tetrahydrothienyl, piperidinyl, pyrrolidinyl, isoxazolidinyl, isothiazolidinyl, pyrazolidinyl, oxazolidinyl, thiazolidinyl, imidazolidinyl, azepanyl, benzazapene, and the like. Ring-forming carbon atoms and heteroatoms of a heterocycloalkyl group can be optionally substituted by oxo or sulfido (e.g., C(O), S(O), C(S), or S(O)2, etc.). The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds. Also included in the definition of heterocycloalkyl are moieties that have one or more aromatic rings fused (i.e., having a bond in common with) to the cycloalkyl ring, for example, benzo or thienyl derivatives of piperidine, morpholine, azepine, etc. A heterocycloalkyl group containing a fused aromatic ring can be attached through any ring-forming atom including a ring-forming atom of the fused aromatic ring. In some embodiments, the heterocycloalkyl has 4-10, 4-7 or 4-6 ring atoms with 1 or 2 heteroatoms independently selected from nitrogen, oxygen, or sulfur and having one or more oxidized ring members.

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas a pyridin-3-yl ring is attached at the 3-position.

The term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified.

Compounds provided herein also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

All compounds, and pharmaceutically acceptable salts thereof, can be found together with other substances such as water and solvents (e.g. hydrates and solvates) or can be isolated.

In some embodiments, preparation of compounds can involve the addition of acids or bases to affect, for example, catalysis of a desired reaction or formation of salt forms such as acid addition salts.

Example acids can be inorganic or organic acids and include, but are not limited to, strong and weak acids. Some example acids include hydrochloric acid, hydrobromic acid, sulfuric acid, phosphoric acid, p-toluenesulfonic acid, 4-nitrobenzoic acid, methanesulfonic acid, benzenesulfonic acid, trifluoroacetic acid, and nitric acid. Some weak acids include, but are not limited to acetic acid, propionic acid, butanoic acid, benzoic acid, tartaric acid, pentanoic acid, hexanoic acid, heptanoic acid, octanoic acid, nonanoic acid, and decanoic acid.

Example bases include lithium hydroxide, sodium hydroxide, potassium hydroxide, lithium carbonate, sodium carbonate, potassium carbonate, and sodium bicarbonate. Some example strong bases include, but are not limited to, hydroxide, alkoxides, metal amides, metal hydrides, metal dialkylamides and arylamines, wherein; alkoxides include lithium, sodium and potassium salts of methyl, ethyl and t-butyl oxides; metal amides include sodium amide, potassium amide and lithium amide; metal hydrides include sodium hydride, potassium hydride and lithium hydride; and metal dialkylamides include lithium, sodium, and potassium salts of methyl, ethyl, n-propyl, iso-propyl, n-butyl, tert-butyl, trimethylsilyl and cyclohexyl substituted amides.

In some embodiments, the compounds and salts provided herein are substantially isolated. By "substantially isolated" is meant that the compound is at least partially or substantially separated from the environment in which it was formed or detected. Partial separation can include, for example, a composition enriched in the compounds provided herein. Substantial separation can include compositions containing at least about 50%, at least about 60%, at least about 70%, at least about 80%, at least about 90%, at least about 95%, at least about 97%, or at least about 99% by weight of the compounds provided herein, or salt thereof. Methods for isolating compounds and their salts are routine in the art.

The term, "room temperature" or "RT" as used herein, are understood in the art, and refer generally to a temperature (e.g., a reaction temperature) that is about the temperature of the room in which the reaction is carried out, for example, a temperature from about 20° C. to about 30° C.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present application also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present application include the conventional non-toxic salts of the parent compound formed, for example, from non-toxic inorganic or organic acids. The pharmaceutically acceptable salts of the present application can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (MeCN) are preferred. Lists of suitable salts are found in *Remington's Pharmaceutical Sciences,* 17th ed., Mack Publishing Company, Easton, Pa., 1985, p. 1418 and *Journal of Pharmaceutical Science,* 66, 2 (1977). Conventional methods for preparing salt forms are described, for example, in *Handbook of Pharmaceutical Salts: Properties, Selection, and Use,* Wiley-VCH, 2002.

Methods of Use

The present application further provides a method of imaging amyloid beta. In some embodiments, the method comprises imaging amyloid beta in a cell sample or a tissue sample. In some embodiments, the method includes imaging amyloid beta in a subject. As used herein, the term "subject," refers to any animal, including mammals. Example subjects include, but are not limited to, mice, rats, rabbits, dogs, cats, swine, cattle, sheep, horses, primates, and humans. In some embodiments, the subject is a human.

The present application further provides a method of diagnosing a disease associated with amyloid beta in a subject. In some embodiments, the method comprises:

i) contact a cell sample or tissue sample of the subject with a compound provided herein (e.g. a compound of any of Formulas I-IX), a pharmaceutically acceptable salt thereof, or a tautomer thereof; and ii) imaging the cell sample or tissue sample with an imaging technique.

In some embodiments, the method comprises:

i) administering to the subject a compound provided herein (e.g. a compound of any of Formulas I-IX), a pharmaceutically acceptable salt thereof, or a tautomer thereof; and ii) imaging the subject with an imaging technique.

In some embodiments, the method is an in vitro method. In some embodiments, the method is an in vivo method.

In some embodiments, the disease is associated with amyloid beta plaque formation. In some embodiments, the disease is associated with amyloid beta crosslinking. In some embodiments, the disease is associated with copper-induced amyloid beta crosslinking.

In some embodiments, the disease is a disease of the central nervous system or a neurodegenerative disease. Example diseases of the central nervous system and neurodegenerative diseases include, but are not limited to, Alzheimer's Disease, attention deficit/hyperactivity disorder (ADHD), Bell's Palsy, bipolar disorder, catalepsy, Cerebal Palsy, epilepsy, encephalitis, Huntington's disease, locked-in syndrome, meningitis, migraine, multiple sclerosis (MS), Parkinson's disease, schizophrenia, tropical spastic paraparesis, Tourette's syndrome, senile dementia of AD type (SDAT), Parkinson's disease, Lewis body dementia, vascular dementia, mild cognitive impairment (MCI), age-associated memory impairment (AAMI) and problems associated with ageing, post-encephalitic Parkinsonism, Amyotrophic lateral sclerosis (ALS), and Down syndrome.

In some embodiments, the disease is selected from the group consisting of Alzheimer's Disease, senile dementia of AD type (SDAT), Parkinson's disease, Lewis body dementia, vascular dementia, mild cognitive impairment (MCI), age-associated memory impairment (AAMI) and problems associated with ageing, post-encephalitic Parkinsonism, Amyotrophic lateral sclerosis (ALS), multiple sclerosis (MS) and Down syndrome. In some embodiments, the disease is Alzheimer's Disease.

In some embodiments, the imaging technique is a non-invasive imaging technique. In some embodiments, the imaging technique is a minimally invasive imaging technique. As used herein, the term "minimally invasive imaging technique" comprises imaging techniques employing the use of an internal probe or injection of a compound (e.g. a radiolabeled compound) via syringe.

Example imaging techniques include, but are not limited to, fluorescence imaging, X-ray imaging, magnetic resonance imaging (MRI), scintigraphic imaging, ultrasound imaging, elastographic imaging, tomographic imaging, echocardiographic imaging, positron emission tomography (PET) imaging, single-photon emission computed tomography (SPECT), positron emission tomography with computed tomography imaging, positron emission tomography with magnetic resonance imaging, and ultrasound imaging.

In some embodiments, the imaging technique is selected from the group consisting of fluorescence imaging, positron emission tomography (PET) imaging, magnetic resonance imaging (MRI), single-photon emission computed tomography (SPECT), positron emission tomography with computed tomography imaging, and positron emission tomography with magnetic resonance imaging.

In some embodiments, the imaging technique is selected from the group consisting of fluorescence imaging, position emission tomography imaging, and single-photon emission computed tomography.

In some embodiments, the amyloid beta comprises soluble amyloid beta (e.g., monomeric, dimeric, and/or oligomeric amyloid beta). In some embodiments, the amyloid beta is soluble amyloid beta (e.g., monomeric, dimeric, and/or oligomeric amyloid beta). In some embodiments, the amyloid beta is insoluble amyloid beta (e.g., aggregated amyloid beta). In some embodiments, the amyloid beta comprises soluble and insoluble amyloid beta.

The present application further provides a method for treating a disease associated with amyloid beta in a subject. In some embodiments, the method comprises administering to the subject a therapeutically effective amount of a compound provided herein (e.g., a compound of any of Formulas I-IX), a pharmaceutically acceptable salt thereof, or a tautomer thereof. In some embodiments, the compound provided herein reduces amyloid beta crosslinking.

In some embodiments, the disease is associated with amyloid beta plaque formation. In some embodiments, the disease is associated with amyloid beta crosslinking. In some embodiments, the disease is associated with copper-induced amyloid beta crosslinking.

In some embodiments, the disease is selected from the group consisting of senile dementia of AD type (SDAT), Parkinson's disease, Lewis body dementia, vascular dementia, mild cognitive impairment (MCI), age-associated memory impairment (AAMI) and problems associated with ageing, post-encephalitic Parkinsonism, Amyotrophic lateral sclerosis (ALS), multiple sclerosis, (MS) and Down syndrome. In some embodiments, the disease is Alzheimer's Disease.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician.

As used herein, the term "treating" or "treatment" refers to one or more of (1) inhibiting the disease; for example, inhibiting a disease, condition or disorder in an individual who is experiencing or displaying the pathology or symptomatology of the disease, condition or disorder (i.e., arresting further development of the pathology and/or symptomatology); and (2) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease or reducing or alleviating one or more symptoms of the disease.

In some embodiments, the treating refers to inhibiting or ameliorating one or more symptoms of a disease provided herein (e.g., Alzheimer's Disease). In some embodiments, the symptom is selected from the group consisting of loss of memory, disorientation and misinterpreting special relationships, difficulty speaking and writing, trouble concentrating, thinking, and/or reasoning, difficulty making judgments or decisions, trouble planning and performing familiar tasks (e.g., cooking a meal, playing a favorite game, or dressing and bathing), and changes in personality and behavior (e.g., depression, social withdrawal, mood swings, distrust in others, irritability and aggressiveness, changes in sleeping habits, wandering, loss of inhibitions, and/or delusions), or any combination thereof, thus, a treatment can result in a reduction in one or more of these symptoms. Administration of a therapeutically effective amount of a compound provided herein for the treatment of a condition associated with amyloid beta plaque (e.g., amyloid beta plaque formation) will result in increased mental function and neuronal protection.

Combination Therapies

One or more additional therapeutic agents such as, for example, anti-inflammatory agents, steroids, immunosuppressants, anesthetics (e.g., for use in combination with a surgical procedure), agents for treating diseases of the central nervous system or neurodegenerative disease, or other agents useful for treating diseases associated with amyloid beta (e.g., a disease of the central nervous system or a neurodegenerative disease) can be used in combination with the compounds and salts provided herein.

Example anti-inflammatory agents include, but are not limited to, aspirin, choline salicylates, celecoxib, diclofenac potassium, diclofenac sodium, diclofenac sodium with misoprostol, diflunisal, etodolac, fenoprofen, flurbiprofen, ibuprofen, ketoprofen, meclofenamate sodium, mefenamic acid, nabumetone, naproxen, naproxen sodium, oxaprozin, piroxican, rofecoxib, salsalate, sodium salicylate, sulindac, tolmetin sodium, and valdecoxib.

Example steroids include, but are not limited to, corticosteroids such as cortisone, dexamethasone, hydrocortisone, methylprednisolone, prednisolone, and prednisone.

Example immunosuppressants include, but are not limited to, azathioprine, chlorambucil, cyclophosphamide, cyclosporine, daclizumab, infliximab, methotrexate, and tacrolimus.

Example anesthetics include, but are not limited to, local anesthetics (e.g., lidocaine, procain, ropivacaine) and general anesthetics (e.g., desflurane, enflurane, halothane, isoflurane, methoxyflurane, nitrous oxide, sevoflurane, mmobarbital, methohexital, thiamylal, thiopental, diazepam, lorazepam, midazolam, etomidate, ketamine, propofol, alfentanil, fentanyl, remifentanil, buprenorphine, butorphanol, hydromorphone levorphanol, meperidine, methadone, morphine, nalbuphine, oxymorphone, pentazocine).

Examples of agents for treating diseases of the central nervous system or neurodegenerative disease include, but are not limited to, cholinesterase inhibitors (e.g., donepezil, galantamine, and rivastigmine), dopamine agonsists (e.g., apomorphine hydrochloride, bromocriptine, pramipexole, and ropinirole), anticholinergics (e.g., benzotropine mesylate and trihexyphenidyl HCl), MAO-B inhibitors (e.g., selegiline, and rasagiline); COMT inhibitors (e.g., entacapone and tolcapone), methylphenidate, and amantadine.

Examples of agents useful for treating diseases associated with amyloid beta may be found, for example, in U.S. Application Publication Nos.: 2011/0208064, 2011/0208064, 2012/0183474, 2015/0158841, and 2016/0193363, the disclosures of each of which are incorporated herein by reference in their entireties. In some embodiments, the agent useful for treating diseases associated with amyloid beta is selected from the group consisting of:

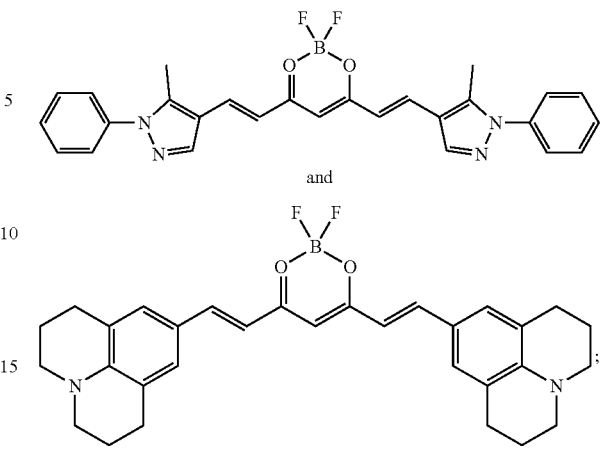

a pharmaceutically acceptable salt thereof, or a tautomer thereof.

In some embodiments, the additional therapeutic agent is administered simultaneously with a compound or salt provided herein. In some embodiments, the additional therapeutic agent is administered after administration of the compound or salt provided herein. In some embodiments, the additional therapeutic agent is administered prior to administration of the compound or salt provided herein. In some embodiments, the compound or salt provided herein is administered during a surgical procedure. In some embodiments, the compound or salt provided herein is administered in combination with an additional therapeutic agent during a surgical procedure.

Pharmaceutical Compositions and Formulations

When employed as pharmaceuticals, the compounds and salts provided herein can be administered in the form of pharmaceutical compositions. These compositions can be prepared as described herein or elsewhere, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral, or parenteral. Parenteral administration includes intravenous, intraarterial, subcutaneous, intraperitoneal intramuscular or injection or infusion; or intracranial, (e.g., intrathecal or intraventricular, administration). Parenteral administration can be in the form of a single bolus dose, or may be, for example, by a continuous perfusion pump. In some embodiments, the compounds, salts, and pharmaceutical compositions provided herein are suitable for parenteral administration. In some embodiments, the compounds, salts, and pharmaceutical compositions provided herein are suitable for intravenous administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Also provided are pharmaceutical compositions which contain, as the active ingredient, a compound provided herein, or a pharmaceutically acceptable salt thereof, in combination with one or more pharmaceutically acceptable carriers (e.g., excipients). In making the compositions provided herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments, soft and hard gelatin capsules, suppositories, sterile injectable solutions, and sterile packaged powders.

Some examples of suitable excipients include, without limitation, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include, without limitation, lubricating agents such as talc, magnesium stearate, and mineral oil; wetting agents; emulsifying and suspending agents; preserving agents such as methyl- and propylhydroxy-benzoates; sweetening agents; flavoring agents, or combinations thereof.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual subject, the severity of the subject's symptoms, and the like.

EXAMPLES

The following examples are offered for illustrative purposes, and are not intended to limit the invention.

Starting materials and solvents used in the Examples were purchased from commercial vendors and used without further purification, unless otherwise noted. The pH of the PBS buffer was 7.4. Column chromatography was performed on silica gel (SiliCycle Inc., 60 Å, 40-63 mm) slurry packed into glass columns. Synthetic Aβ peptides (1-40/42) were purchased from rPeptide (Bogart, Ga., 30622). Aggregates for in vitro studies were generated by the slow stirring of Aβ40 in PBS buffer for 3 days at room temperature. CRANAD-101F (Example 1) was dissolved in DMSO to prepare a 25.0 μM stock solution. $^1$H and $^{13}$C NMR spectra were recorded at 300 and 125 MHz, respectively, and reported in ppm downfield from tetramethylsilane (TMS). Fluorescence measurements were performed using an F-4500 fluorescence spectrophotometer (Hitachi). Transgenic female APP-PS1 mice and age matched wild-type female mice were purchased from Jackson Laboratory.

In vivo PET imaging was conducted with 14-month old APP/PS1 mice (Charles River Laboratories, MA) and age-matched wild-type (WT) mice. Mice were injected via tail-vein with 100 μL of 20-30 μCi of [$^{18}$F]CRANAD-101 (Example 2) in 10% ethanol saline. MicroPET imaging experiments were performed on a Sophie Biosciences microPET G4 scanner (Culver City, Calif., USA). 60-Minute dynamic imaging was performed under general anesthesia (isoflurane/O$_2$). Imaging analysis was conducted with Amide.

Intermediate 1. 4-cyclobutyl-2,2-difluoro-6-methyl-2H-1,3λ$^3$,2λ$^4$-dioxaborinine

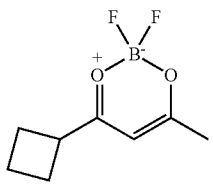

To a solution of 1-cyclobutylbutane-1,3-dione (1 g, 7.13 mmol) in 10 mL DCM, BF$_3$.Et$_2$O (2 eq.) was added dropwise at room temperature. The mixture was stirred for 12 h, at which time no starting material was observed via thin layer chromatography (TLC). The reaction mixture was concentrated and purified with silica column chromatography (hexanes/ethyl acetate=2/1) to afford compound Intermediate 1 as a pale yellow liquid (740 mg, yield: 90%). $^1$H NMR (CDCl$_3$) δ (ppm) 1.89-2.12 (m, 2H), 2.28 (s, 3H), 2.30-2.41 (m, 4H), 3.30-3.36 (m, 1H), 5.92 (s, 1H); $^{13}$C NMR (CDCl$_3$) δ (ppm) 17.97, 24.14, 25.71, 40.85, 99.58, 192.17, 196.42; $^{19}$F NMR (CDCl$_3$) δ (ppm) 138.75, 138.69; ESI-MS (M+H$_2$O) m/z=206.1, (M+Na$^+$)=211.0

Example 1. CRANAD-101

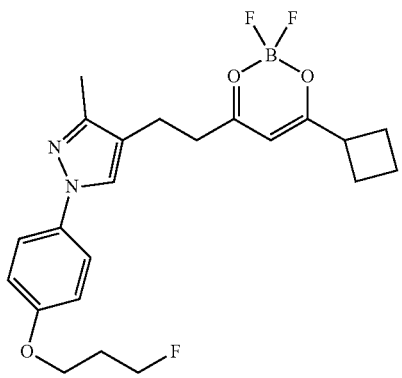

Step 1. 1-(4-hydroxyphenyl)-3-methyl-1H-pyrazole-4-carbaldehyde

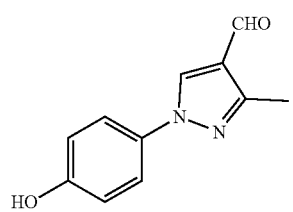

To a solution of 1-(4-methoxyphenyl)-3-methyl-1H-pyrazole-4-carbaldehyde (1 g, 4.624 mmol) in 10 mL anhydrous dichloromethane (DCM), BBr$_3$ (1M, 9.248 mmol, 2 eq.) was added drop-wise at −78° C. under N$_2$. The resulting mixture was stirred at −78° C. for 30 min, then warmed to room temperature and stirred for 2 h. Next, the mixture was quenched with water, and the pH of the resulting solution was adjusted with Na$_2$CO$_3$ to pH=8. The organic layer was separated and the aqueous phase was extracted with ethyl acetate (EtOAc) two times, and the organic layers were combined and dried over anhydrous Na$_2$SO$_4$. After removing the solvent, the resulting residue was purified with silica column chromatography (hexanes/ethyl acetate=1/1) to afford 1-(4-hydroxyphenyl)-3-methyl-1H-pyrazole-4-carbaldehyde as a gray solid (740 mg, yield: 79.1%). $^1$H NMR (CDCl$_3$) δ (ppm) 2.54 (s, 3H), 6.84 (d, J=8.7 Hz, 2H), 7.19 (d, J=8.7 Hz, 2H), 8.06 (s, 1H), 9.96 (s, 1H); $^{13}$C NMR (CDCl$_3$) δ (ppm) 11.46, 116.28, 121.35, 127.01, 130.28, 141.96, 143.91, 156.97, 185.01; ESI-MS (M+H) m/z=203.0.

Step 2. 1-(4-(3-hydroxypropoxy)phenyl)-3-methyl-1H-pyrazole-4-carbaldehyde

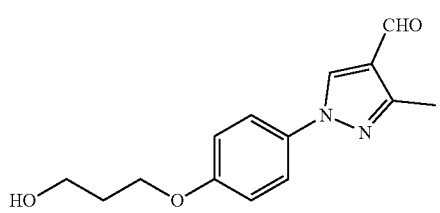 [SMILES: Cc1nn(-c2ccc(OCCCO)cc2)cc1C=O]

A mixture of 1-(4-hydroxyphenyl)-3-methyl-1H-pyrazole-4-carbaldehyde (214 mg, 1.057 mmol, 1 eq.), 3-iodopropan-1-ol (1.27 g, 1.268 mmol, 1.2 eq), K$_2$CO$_3$ (292 mg, 2.114 mmol, 2 eq.) in 5 mL CH$_3$CN was heated at reflux for 24 h. The mixture was then filtered, and the remaining solid was washed with EtOAc twice (10 mL each time). The organic layers were concentrated and purified using silica column chromatography to afford 1-(4-(3-hydroxypropoxy)phenyl)-3-methyl-1H-pyrazole-4-carbaldehyde as a yellow solid (190 mg, yield: 69%). $^1$H NMR (CDCl$_3$) δ (ppm) 2.04-2.12 (m, 2H), 2.55 (s, 3H), 3.86-3.90 (t, 2H), 4.15-4.19 (t, 2H), 7.03 (d, J=9.0 Hz, 2H), 7.34 (d, J=9.0 Hz, 2H), 8.03 (s, 1H), 9.96 (s, 1H); $^{13}$C NMR (CDCl$_3$) δ (ppm) 11.55, 31.88, 59.94, 65.77, 114.97, 121.48, 126.74, 131.18, 142.13, 143.41, 159.13, 184.94; ESI-MS (M+H) m/z=261.0.

Step 3. 3-(4-(4-formyl-3-methyl-1H-pyrazol-1-yl)phenoxy)propyl 4-methylbenzenesulfonate

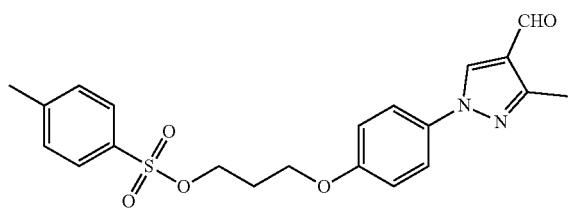

To a solution of 1-(4-(3-hydroxypropoxy)phenyl)-3-methyl-1H-pyrazole-4-carbaldehyde (190 mg, 0.731 mmol, 1 eq.) in 5 mL anhydrous DCM, Et$_3$N (305 μL, 2 eq.) was added, followed by the addition of 4-dimethylaminopyridine (DMAP, 90 mg, 0.931 mmol, 1 eq.). To the resulting mixture, 4-methylbenzene-1-sulfonyl chloride (167 mg, 0.877 mmol, 1.2 eq.) was added portion-wise at 0° C., and the reaction mixture was warmed to room temperature and stirred for 4 h. The solution was then concentrated and the resulting residue was purified using silica column chromatography (hexanes/ethyl acetate=1/1) to afford 3-(4-(4-formyl-3-methyl-1H-pyrazol-1-yl)phenoxy)propyl 4-methylbenzenesulfonate as a yellow solid (210 mg, yield: 69.4%). $^1$H NMR (CDCl$_3$) δ (ppm) 2.11-2.19 (m, 2H), 2.39 (s, 3H), 2.54 (s, 3H), 4.0-4.04 (t, 2H), 4.23-4.27 (t, 2H), 6.87 (d, J=9 Hz, 2H), 7.27 (m, 2H), 7.75 (d, J=8.1 Hz, 2H), 8.02 (s, 1H), 9.96 (s, 1H); $^{13}$C NMR (CDCl$_3$) δ (ppm) 11.54, 21.60, 28.76, 63.53, 66.77, 114.88, 121.52, 126.67, 127.82, 129.83, 131.34, 132.75, 142.11, 143.37, 144.87, 158.73, 184.91; ESI-MS (M+H) m/z=415.0.

Step 4. 1-(4-(3-fluoropropoxy)phenyl)-3-methyl-1H-pyrazole-4-carbaldehyde

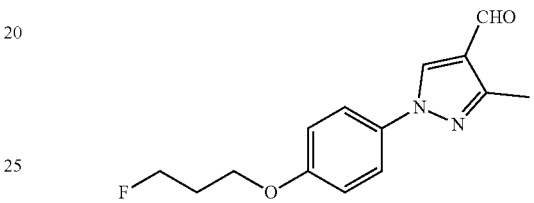

To a solution of 3-(4-(4-formyl-3-methyl-1H-pyrazol-1-yl)phenoxy)propyl 4-methylbenzenesulfonate (210 mg, 0.507 mmol, 1 eq.) in 5 mL anhydrous THF, triethylammonium bicarbonate (TEAB, 1M in toluene, 1.2 eq.) was added, and the resulting mixture was heated at reflux for 4 h. The solvent was then removed, and the resulting residue was purified with silica column chromatography (hexanes/ethyl acetate=1/1) to afford 1-(4-(3-fluoropropoxy)phenyl)-3-methyl-1H-pyrazole-4-carbaldehydeas a yellow solid (69 mg, yield: 51.9%). $^1$H NMR (CDCl$_3$) δ (ppm) 2.12-2.29 (m, 2H), 2.54 (s, 3H), 4.13-4.17 (t, 2H), 4.57-4.61 (t, 1H), 4.72-4.76 (t, 1H) 6.98 (m, 2H), 7.31 (m, 2H), 8.02 (s, 1H), 9.96 (s, 1H); $^{13}$C NMR (CDCl$_3$) δ (ppm) 11.54, 30.14, 30.40, 63.85, 63.91, 79.37, 81.56, 114.96, 121.49, 126.74, 131.27, 142.13, 143.37, 159.04, 184.92; $^{19}$F NMR (CDCl$_3$) δ (ppm) 218.26, 218.35, 218.43, 218.52, 218.59, 218.69. ESI-MS (M+H) m/z=223.0.

Step 5. (E)-4-(2-(6-cyclobutyl-2,2-difluoro-2H-1,3,2$^4$-dioxaborinin-4-yl)vinyl)-1-(4-(3-fluoropropoxy)phenyl)-3-methyl-1H-pyrazole (CRANAD-101)

A mixture of 1-(4-(3-fluoropropoxy)phenyl)-3-methyl-1H-pyrazole-4-carbaldehyde (69 mg, 0.2633 mmol, 1 eq.), Intermediate 1 (49.5 mg, 0.2633 mmol, 1 eq.), 1,2,3,4-tetrahydroisoquinoline (8 μL), and AcOH (40 μL) in 3 mL CH$_3$CN was heated at reflux for 15 min, and the reaction mixture was then cooled to room temperature. The reaction mixture was concentrated, and the resulting residue was purified with silica gel column chromatography (hexanes/ethyl acetate=1/1) to afford CRANAD-101 as a yellow solid (30 mg, yield: 26.4%). $^1$H NMR (CDCl$_3$) δ (ppm) 2.12-2.44 (m, 10H), 2.39 (s, 3H), 3.33-3.39 (m, 1H) 4.14-4.18 (t, 2H), 4.57-4.61 (t, 1H), 4.73-4.77 (t, 1H), 5.87 (s, 1H), 6.39 (d, J=15.3 Hz 1H), 6.99 (d, J=9.0 Hz 1H), 7.31 (d, J=9.0 Hz, 2H), 7.94 (s, 1H), 7.97 (d, J=15.3 Hz, 1H); $^{13}$C NMR (CDCl$_3$) δ (ppm) 10.94, 18.05, 25.94, 30.15, 30.42, 41.12, 63.86, 63.93, 79.38, 81.56, 98.69, 114.97, 116.61, 117.34, 126.49, 131.75, 138.74, 138.98, 142.01, 158.93, 180.52, 194.19; ¹⁹F NMR (CDCl₃) δ (ppm) 136.29, 136.35, 218.45, 218.52, 218.62, 218.69, 218.78. ESI-MS (M+H) m/z=433.0.

Example 2. [¹⁸F]CRANAD-101

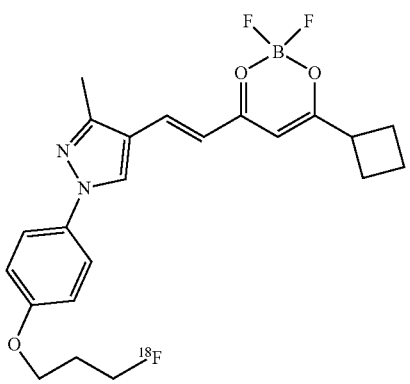

[¹⁸F]Fluoride was trapped on an ion exchange cartridge from ¹⁸O-enriched water and subsequently released with a solution of TEAB (2 mg) in 1 mL of MeCN/H2O (v/v 7/3) into a 5 mL sealed vial. The solution was evaporated at 110° C. under a stream of nitrogen. The evaporation was repeated three times with addition of dry acetonitrile (1 mL) each time. The dried [¹⁸F]fluoride was then re-dissolved in 0.2 mL of dry acetonitrile. To an oven-dried vial containing 3-(4-(4-formyl-3-methyl-1H-pyrazol-1-yl)phenoxy)propyl 4-methylbenzenesulfonate (Example 1, Step 3, 4.15 mg) and a magnetic stirrer bar, anhydrous acetonitrile (0.3 mL) was added, followed by the addition of 0.1 mL of tetraethylammonium [¹⁸F]fluoride ([¹⁸F]TEAF) in acetonitrile. The vial was sealed and heated at 80° C. for 10 min. An aliquot (approximately 2-5 μL) was taken for analysis by radioTLC (eluent: ethyl acetate) using a Bioscan AR-2000 radio-TLC imaging scanner and WinScan software to calculate radiochemical conversion (RCC). Tetrahydroisoquinoline (0.015 mL), AcOH (0.05 mL) and Intermediate 1 (0.01 mL) were added to the reaction mixture, and the resulting mixture was heated at 80° C. for 10 min. The mixture was cooled and diluted with mobile phase (EtOAc, 4 mL). The radiolabeled [¹⁸F]CRANAD-101 was purified using semi-prep radio-HPLC. The identity of the compound was determined via co-injection with the non-radioactive standard (Example 1). The purified [¹⁸F]-CRANAD-101 was then reformulated in 10% ethanol saline solution for use intravenous injection.

Analytical radio-HPLC conditions: Column: Luna® 5 μm C18 100 Å 250×4.6 mm. Mobile phase: 60% CH₃CN, 40% 0.1 M NH₄.HCO₂ (aq); Flow rate: 1.0 mL/min, RT=18 min. Semi-prep radio-HPLC conditions: Column: Luna® 5 μm C18 (2) 100 Å 250×10.00 mm. Mobile phase: 60% CH₃CN, 40% 0.1 M NH₄.HCO₂ (aq); Flow rate: 5.0 mL/min, RT=18 min. RCC: ~51%.

Example 3. CRANAD-104F

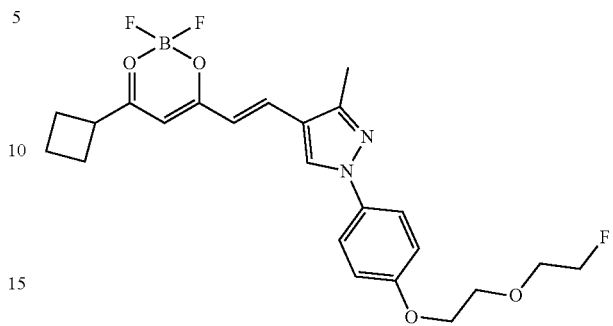

The title compound was prepared according to procedures similar to the methods provided in Example 1. ¹H NMR (CDCl₃) δ (ppm) 2.03-2.14 (m, 2H), 2.26-2.39 (m, 4H), 2.44 (s, 3H), 3.33-3.36 (m, 1H), 3.77-3.79 (t, 1H), 3.78-3.80 (t, 1H), 3.88-3.94 (m, 2H), 4.18-4.22 (m, 2H), 4.51-4.54 (m, 1H), 4.67-4.70 (m, 1H), 5.87 (s, 1H), 6.39 (d, J=15.3 Hz 1H), 7.01 (d, J=9.0 Hz, 2H), 7.31 (d, J=9.0 Hz, 2H), 7.93 (s, 1H), 8.02 (d, J=15.3 Hz, 1H); ¹³C NMR (CDCl₃) δ (ppm) 10.95, 18.05, 25.93, 41.12, 67.82, 69.77, 70.49, 70.75, 82.00, 84.24, 98.69, 115.15, 116.60, 117.34, 126.43, 131.84, 138.74, 138.99, 142.01, 158.89, 180.52, 194.17. ESI-MS (M+H) m/z=463.1.

Example 4. CRANAD-108F

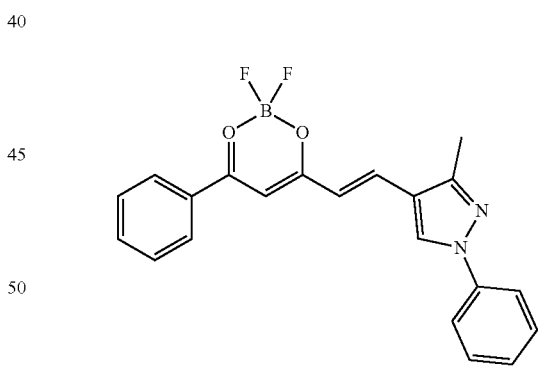

The title compound was prepared according to procedures similar to the methods provided in Example 1. ¹H NMR (CDCl₃) δ (ppm) 2.49 (s, 3H), 6.58 (s, 1H), 6.63 (s, 1H), 7.43-7.56 (m, 7H), 7.63-7.68 (t, 1H), 8.02 (s, 1H), 8.06-8.12 (t, 3H); ¹³C NMR (CDCl₃) 11.12, 97.31, 117.36, 117.82, 125.04, 128.56, 128.77, 129.02, 129.36, 132.17, 134.62, 138.67, 139.33, 142.08, 180.88, 181.07 δ (ppm)¹⁹F NMR (CDCl₃) δ (ppm) 140.48, 140.55. ESI-MS (M+H) m/z=379.0.

Example 5. CRANAD-109F

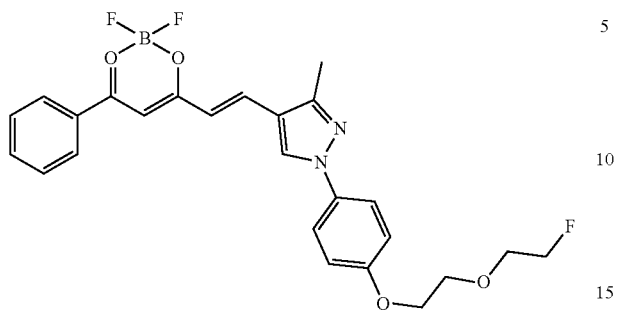

The title compound was prepared according to procedures similar to the methods provided in Example 1. $^1$H NMR (CDCl$_3$) δ (ppm) 2.43 (s, 3H), 3.78-3.81 (t, 1H) 3.88-3.91 (t, 1H), 3.92-3.95 (t, 2H), 4.19-4.22 (t, 2H), 4.52-4.54 (t, 1H), 4.68-4.70 (t, 1H), 6.57 (s, 1H), 6.61 (s, 1H), 7.03-7.06 (d, J=9.0 Hz, 2H), 7.33-7.36 (d, J=9.0 Hz, 2H), 7.50-7.55 (t, 2H), 7.62-7.67 (t, 1H), 7.99 (s, 1H), 8.05-8.10 (m, 3H); $^{13}$C NMR (CDCl$_3$) δ (ppm) 10.99, 67.83, 69.78, 70.50, 70.76, 82.01, 84.25, 97.27, 115.17, 117.12, 117.50, 126.45, 128.54, 129.00, 131.82, 132.18, 134.56, 138.87, 139.10, 142.22, 158.92, 180.92; 19F NMR (CDCl$_3$) δ (ppm) 136.59, 136.53, 218.60-219.04. ESI-MS (M+H) m/z=485.0.

Example 6. CRANAD-97

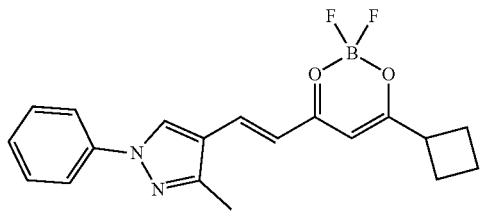

The title compound was prepared according to procedures similar to the methods provided in Example 1. $^1$H NMR (CDCl$_3$) δ (ppm) 2.01-2.07 (m, 2H), 2.23-2.37 (m, 4H), 2.45 (s, 3H), 3.34-3.39 (m, 1H), 5.89 (s, 1H), 6.41 (d, J=15.6 Hz, 1H), 7.41-7.54 (m, 5H), 7.97 (s, 1H), 8.03 (d, J=15.9 Hz, 1H) $^{13}$C NMR (CDCl$_3$) δ (ppm) 11.08, 18.05, 25.94, 41.13, 98.75, 116.86, 117.67, 125.02, 128.73, 129.24, 129.34, 138.54, 138.63, 139.23, 141.87, 180.48, 194.36 ESI-MS (M+H) m/z=357.1.

Example 7. CRANAD-93

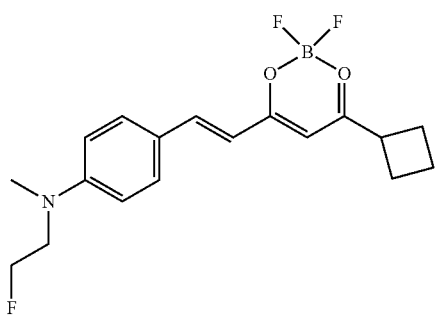

The title compound was prepare according to procedures similar to the methods provided in Example 1. ESI-MS (M+H) m/z=352.1.

Example 8. CRANAD-92

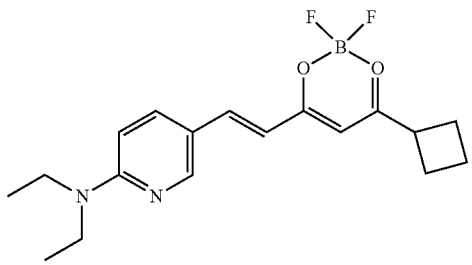

The title compound was prepared according to procedures similar to the methods provided in Example 1. ESI-MS (M+H) m/z=349.1.

Example 9. CRANAD-111

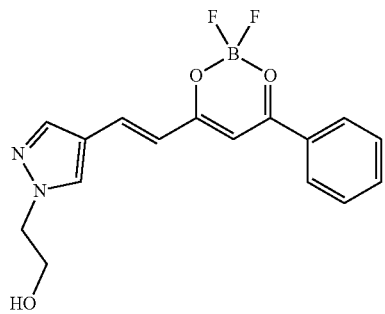

The title compound was prepared according to procedures similar to the methods provided in Example 1. $^1$H NMR (DMSO) δ (ppm) 3.71-3.76 (m, 2H), 4.18-4.21 (m, 2H), 4.96 (m, 1H), 6.85 (d, J=15.6 Hz, 1H), 7.23 (s, 1H), 7.60 (t, 2H), 7.73 (t, 1H), 8.06 (s, 1H), 8.15 (t, 2H), 8.22 (s, 1H), 8.34 (s, 1H); $^{13}$C NMR (DMSO) δ (ppm) 55.02, 60.00, 97.17, 118.04, 118.76, 128.78, 129.81, 132.06, 134.69, 135.35, 140.67, 141.86, 179.31, 182.48. ESI-MS (M+H) m/z=333.0.

Example 10. CRANAD-99

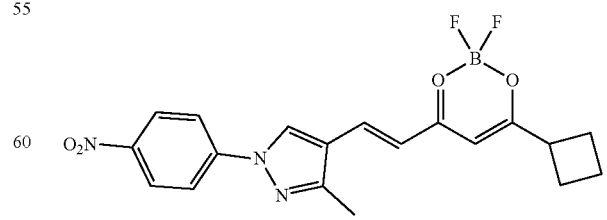

The title compound was prepared according to procedures similar to the methods provided in Example 1. ESI-MS (M+H) m/z=402.1.

Example 11. CRANAD-98

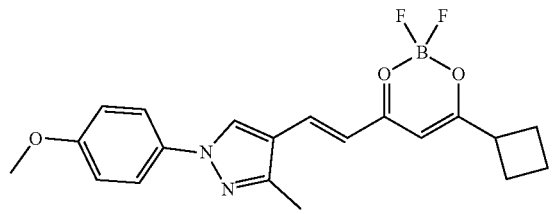

The title compound was prepared according to procedures similar to the methods provided in Example 1. $^1$H NMR (CDCl$_3$) δ (ppm) 2.01-2.07 (m, 2H), 2.23-2.37 (m, 4H), 2.43 (s, 3H), 3.32-3.39 (m, 1H), 3.86 (s, 1H), 5.88 (s, 1H), 6.40 (d, J=15.3 Hz, 1H), 6.99-7.01 (q, 2H), 7.31-7.34 (q, 2H), 7.94 (s, 1H), 8.02 (d, J=15.3 Hz, 1H) $^{13}$C NMR (CDCl$_3$) δ (ppm) 10.94, 18.05, 25.93, 41.10, 55.57, 98.69, 114.44, 116.58, 117.32, 126.46, 131.60, 138.76, 138.98, 142.03, 159.74, 180.53, 194.15. ESI-MS (M+H) m/z=387.1.

Example 12. Fluorescence Spectral Testing of CRANAD-101 with Aβs

To record the fluorescence response of CRANAD-101 with Aβs, the following procedure was used. Step 1: 1.0 mL of PBS buffer was added to a quartz cuvette as a blank control and its fluorescence was recorded with the same parameters as for CRANAD-101. Step 2: The fluorescence emission spectrum of a CRANAD-101 solution (1.0 mL, 250 nM) was recorded with excitation at 420 nm and emission from 450 to 800 nm. Step 3: To the CRANAD-101 solution from Step 2, 10 μL Aβs (25 μM) was added (final concentration 250 nM). The emission spectra was recorded (Excitation=420 nm, Emission=450-800 nm). The final spectra from Steps 2 and 3 were corrected using the blank control from Step 1.

Figure 2:
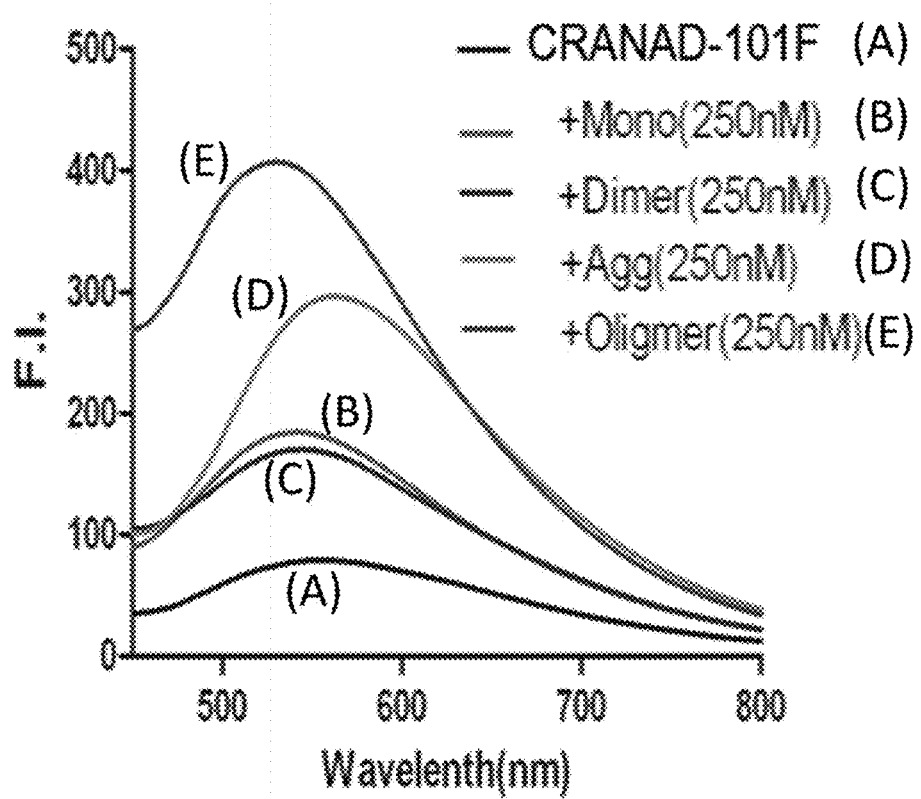
FIG. 2 shows the fluorescence responses of CRANAD-101 in the absence of Aβ (Trace A), with Aβ42 monomers (Trace B), Aβ42 dimers (Trace C), Aβ40 aggregates (Trace D), and Aβ42 oligomers (Trace E).

The emission peak of CRANAD-101 was approximately 550 nm, and its excitation peak was approximately 420 nm. To confirm whether CRANAD-101 was responsive to Aβs, including monomers, dimers, oligomers, and aggregates, PBS buffer was used as a blank, CRANAD-101 (250 nM, final concentration) was added in PBS buffer and the fluorescence intensity was recorded. Next, Aβ monomer (250 nM, final concentration) was added, and the fluorescence intensity was recorded. The same procedure was then performed for Aβ dimers, Aβ oligomers, and Aβ aggregates. It was observed that CRANAD-101 had strong responses to Aβs, as shown in FIG. 2. The binding constant (Kd) of CRANAD-101 was also measured for Aβs. Aβ aggregates, Kd=188.5±104.4 nM; Aβ42 oligomers, Kd=780±173.4 nM; Aβ42 dimers, Kd=44.01±18.9 nM; and Aβ42 monomers, Kd=11.6±11.0 nM. Together, the solution tests suggested that CRANAD-101 was binding to insoluble Aβ aggregates and to soluble Aβs, including monomers, dimers, and oligomers.

Example 13. Brain Slice Testing

Figure 3A:
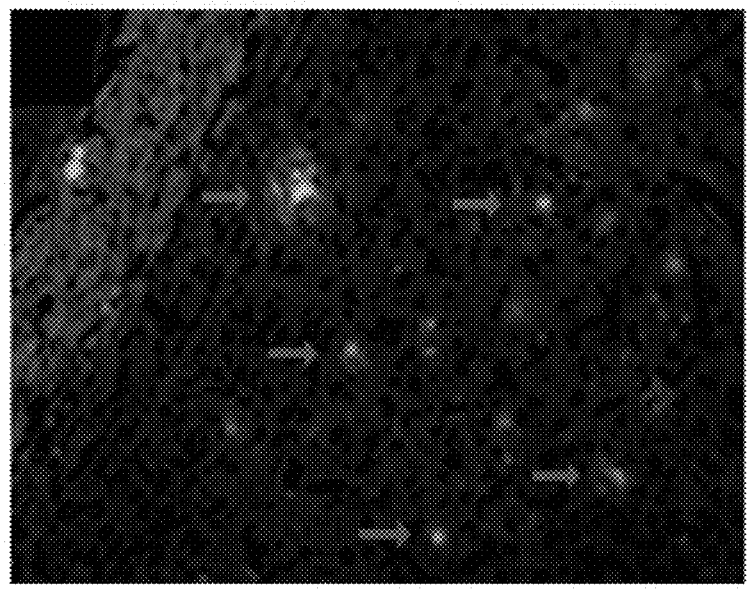
FIG. 3A shows a representative fluorescence microscopic image of APP/PS1 mouse brain slices with CRANAD-101F.

A brain slice of 11-month old APP/PS1 mouse was washed with double-distilled water for 5 minutes, then fixed with 4% formalin for 5 minutes, and washed with double-distilled water. First, a background image of a brain slice was taken using a fluorescence microscope. Next, an image was taken after the slice was incubated with CRANAD-101 (25 μM) for 30 minutes. It was found that Aβ plaques could be imaged after the incubation, as shown in FIG. 3A, suggesting that CRANAD-101 was capable of staining Aβ species.

Example 14. [$^{18}$F]CRANAD-101 Autoradiograph Test

Brain slices from a 14-month APP/PS1 mouse and wild type (WT) mice (an age-matched control) were washed with double-distilled water for 5 minutes, then fixed with 4% formalin for 5 minutes, and washed with double-distilled water. The slices were subsequently dried, then incubated with [$^{18}$F]CRANAD-101 (5 μCi) for 30 min. The slices were then washed with 20% ethanol PBS buffer and dried. The dried slices were exposed to an imaging plate for 1 hour, and the plate was scanned with autoradiography system Cyclone (Perkin Elmer).

Figure 3B:
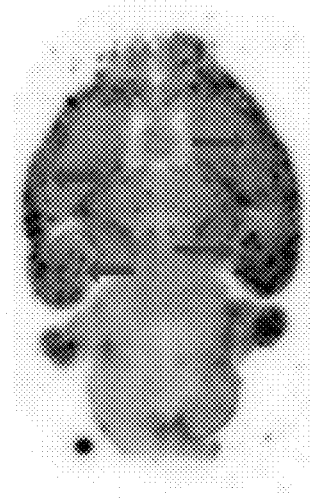
FIG. 3B shows representative autoradiography images of APP/PS1 and wild type (WT) mice brain slices with CRANAD-101[$^{18}$F]. The images show that CRANAD-101F stains Aβ deposits in the cortex and hippocampus areas (arrows).
Figure 3B:
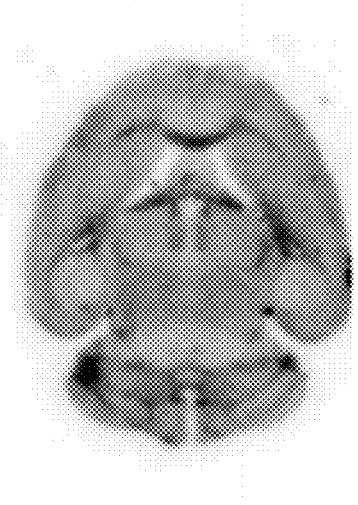
Figures 3C, 3D:
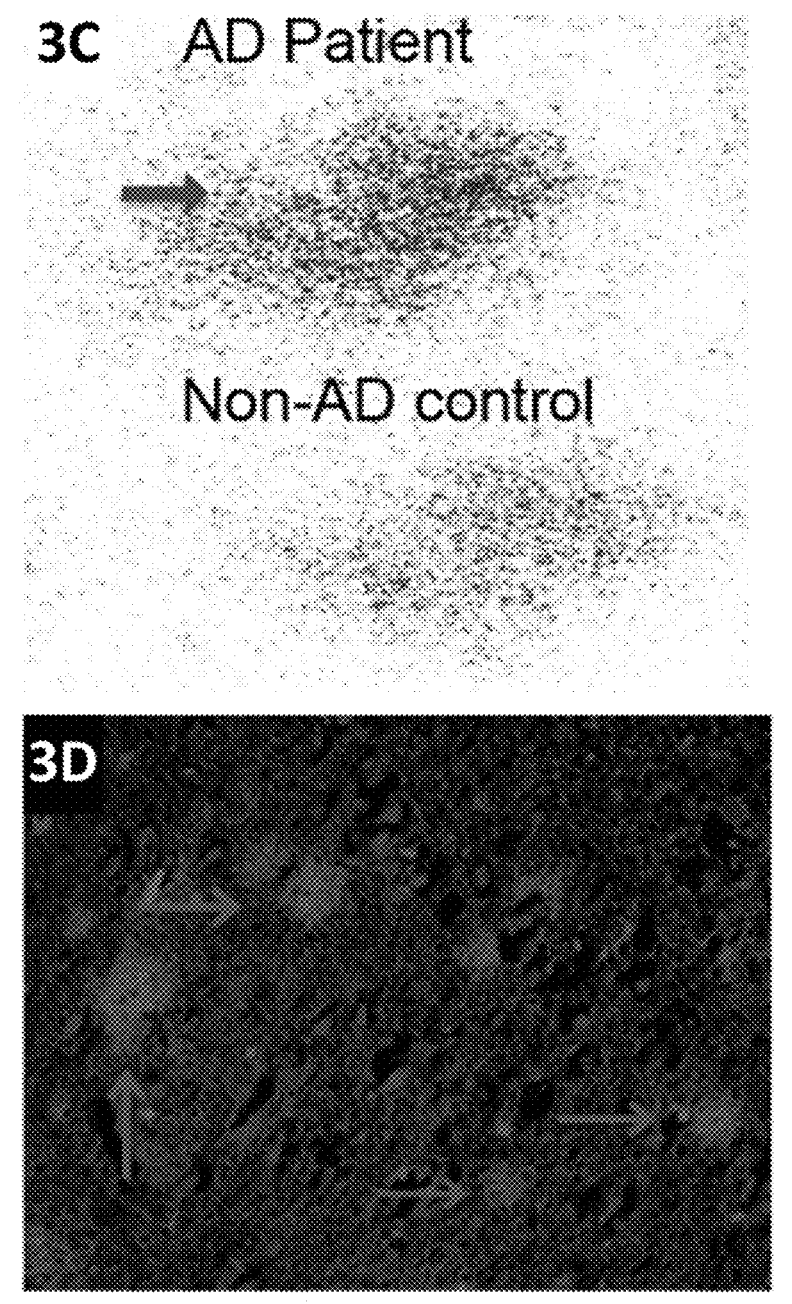

The autoradiography images showed higher retention on the AD slice (from the APP/PS1 mouse), while no apparent staining was observed for the control slice, as shown in FIG. 3B. The [$^{18}$F]CRANAD-101F stained areas of the AD slice were consistent with the accumulation areas of Aβ deposits, as shown in FIG. 3B. In addition, [$^{18}$F]CRANAD-101F also showed higher retention in human AD brain slice than that in health control slice, as shown in FIGS. 3C-3D.

Example 15. In Vivo PET Imaging

In vivo PET imaging was conducted with 14-month old APP/PS1 mice and age-matched WT mice. Mice were injected (i.v.) with 100 μL of 20-30 μCi of [$^{18}$F]CRANAD-101 in 10% ethanol saline. The specific activity was determined to be 1.19 μCi/μmol at the time of injection. PET imaging results indicated that APP/PS1 mice had higher probe retention in brain than the control wild type mice, as shown in FIGS. 4A-4B, and the peak of uptake reached 4.5 RE:% ID/cc, as shown in FIG. 4C. When compared to other reported $^{18}$F labeled curcumin analogues (see e.g., Ryu et al, *Journal of Medicinal Chemistry*, 2006, 49:6111-6119), CRANAD-101F showed much higher penetration of the blood-brain barrier (BBB) and brain accumulation, suggesting that half-curcuminoid CRANAD-101F a useful PET tracers for imaging Aβ. Moreover, [$^{18}$F]CRANAD-101 showed a good clearance rate (% ID/g$_{(2\ min)}$/% ID/g$_{(30\ min)}$=3.2). Quantitative analysis showed that the differences between APP/PS1 mice and control mice were 1.22-, 1.34-, 1.43-, and 1.39-folds at 5-, 18-, 30-, and 60-minutes post-injection, respectively. Compared to WT mice, the probe retention in the cortex and hippocampus areas were higher in the APP/PS1 mice, indicating that [$^{18}$F]CRANAD-101 is useful for in vivo PET imaging.

The over-accumulation of soluble Aβs is an important phenomenon at the early stage of AD pathology, and the in vitro fluorescence tests described herein suggest that CRANAD-101 was also responsive to soluble Aβs. To examine whether [$^{18}$F]CRANAD-101 was capable of detecting soluble Aβs in vivo, PET imaging was performed with 5-month old APP/PS1 mice, in which soluble Aβs are the dominant Aβ sub-species in brains. It was found that the [$^{18}$F]CRANAD-101 had higher retention (1.09-, 1.16-, 1.09-folds at 15-, 30-, and 60-minutes post i.v.), as shown in FIG. 4D. This data shows that [$^{18}$F]-CRANAD-101 was capable of imaging Aβs in vivo.

Example 16. Two-Photon Imaging of Wild-Type and Alzheimer's Disease Mice with CRANAD-101

To investigate whether CRANAD-101 was capable of penetrating brain blood barrier (BBB), two-photon microscopic imaging was conducted using a 15-month old wild type (WT) mouse. A mouse (19-months old) was anesthetized with Ketamine/xylazine (70 mg/kg) and a cranial imaging window was surgically prepared. CRANAD-101 (2.0 mg/kg in a fresh solution containing 15% CREMOPHOR EL®, 15% DMSO and 70% PBS) was injected intravenously at time=0 min by a bolus injection during image acquisition. Two-photon fluorescence excitation was performed with a 900-nm laser (Prairie Ultima). Imaging was performed using a two-photon microscope (Prairie Technologies) equipped with a 20× water immersion objective (N.A. 1.0, Zeiss). Images were collected for 15 seconds per frame 512×512 μm matrix for 45 min with a green (500-550 nm) channel.

Figure 5A:
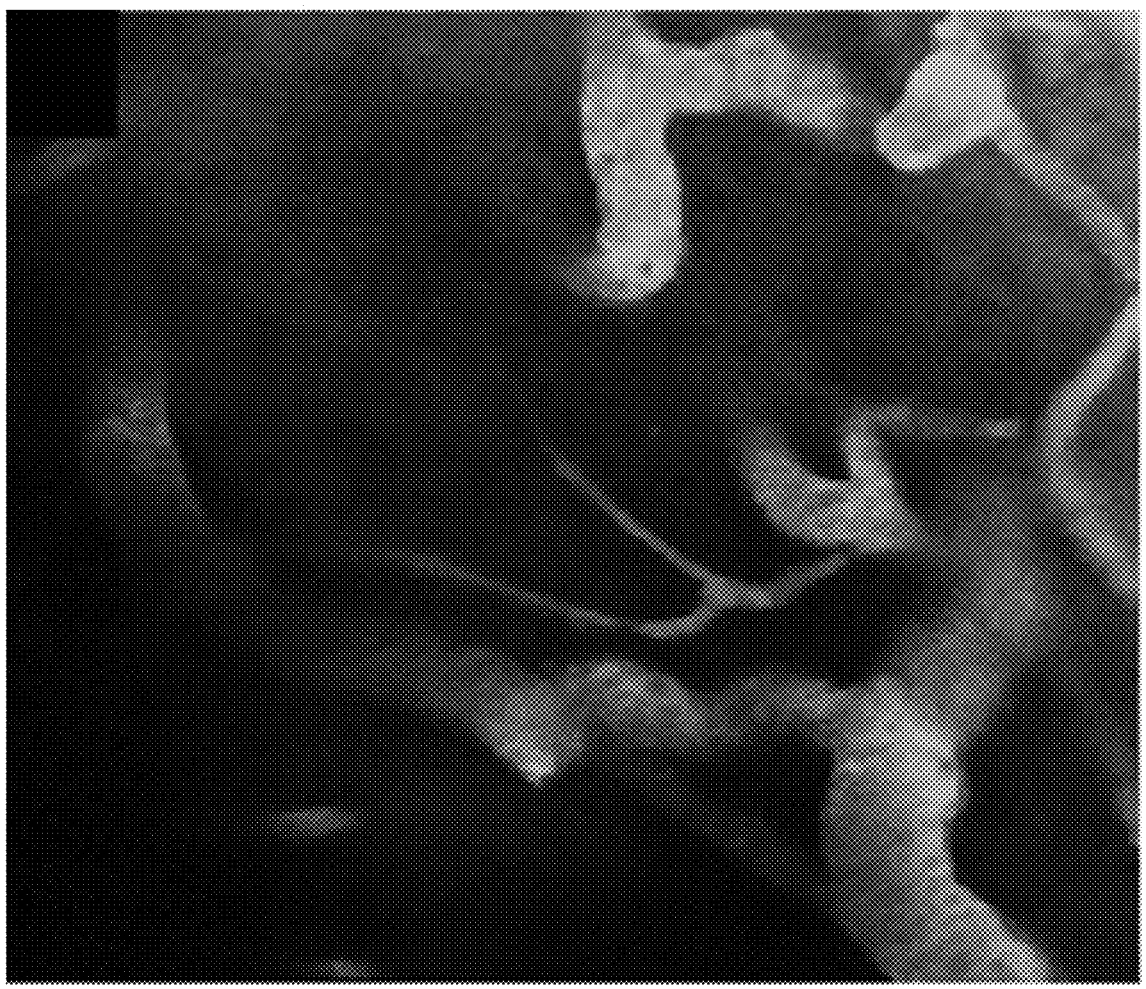
FIGS. 5A-5B shows in vivo two-photo microscopic images of a WT mouse (FIG. 5A) and APP/PS1 mouse (FIG. 5B) using CRANAD-101. The white arrows of FIG. 5B indicate Aβ plaques.
Figure 5B:
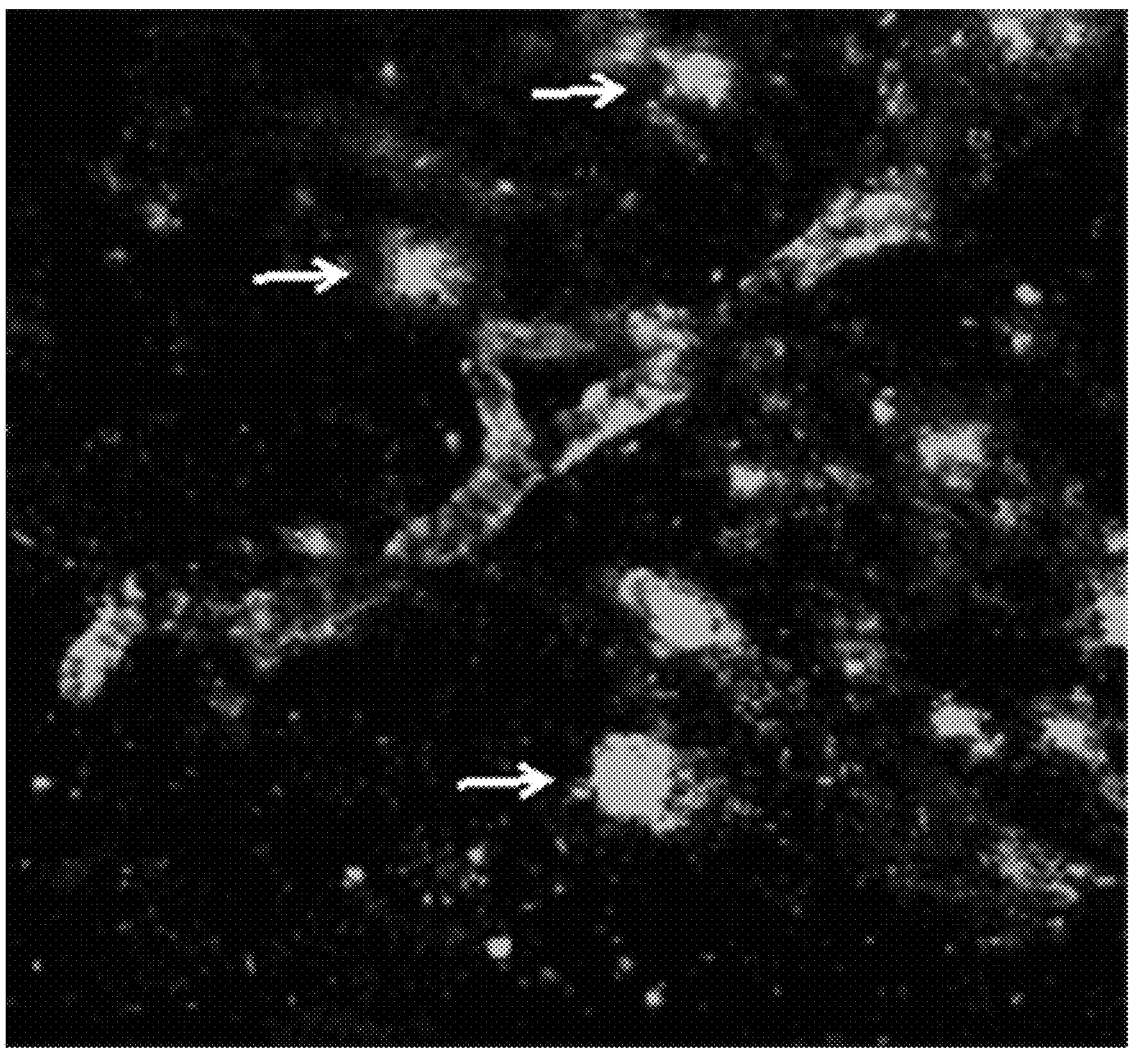
Figure 5C:
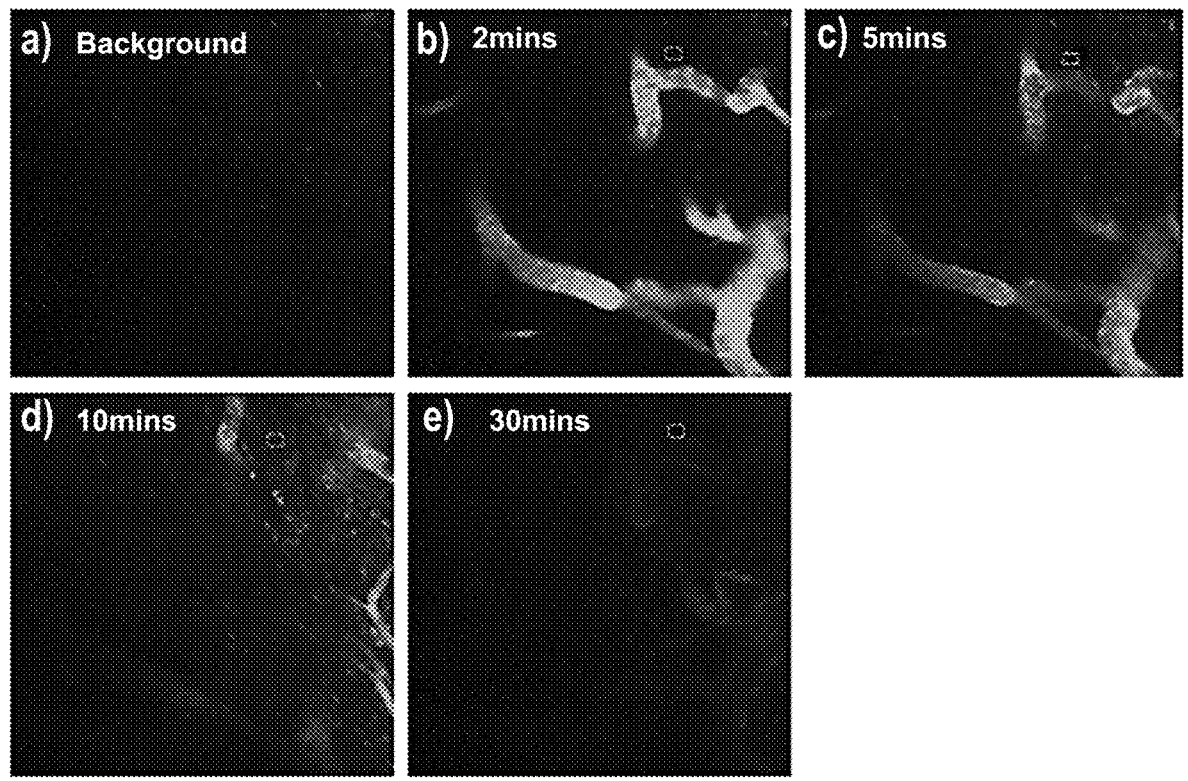
FIG. 5C shows time-lapse two-photon imaging of a WT mouse using CRANAD-101 (panels a-e) and an accumulation time course of CRANAD-101 across the blood brain barrier (panel f).

It was found that CRANAD-101 quickly crossed the BBB, as evidenced by the blurred signals outside of the vessels (FIG. 5A and FIG. 5C, panels a-e). The accumulation of CRANAD-101 in the brain reached a peak at 10 minutes after i.v. injection (FIG. 5C, panel f). To examine whether CRANAD-101 could label Aβ plaques and cerebral amyloid angiopathy (CAA) in vivo, a similar two-photo microscopic imaging procedure was performed with a 15-month old APP/PS1 mouse. CRANAD-101 clearly highlighted Aβ plaques and CAAs (FIG. 5B), indicating CRANAD-101 is a promising candidate for PET tracer development.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of imaging amyloid beta in a subject, comprising:

i) administering to the subject a compound of Formula (I):

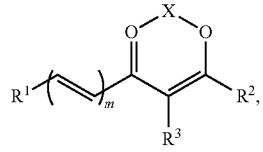

a pharmaceutically acceptable salt thereof, or a tautomer thereof, wherein:

X is $BR^4R^5$;

$R^1$ is selected from the group consisting of $C_{3-10}$ cycloalkyl, $C_{6-10}$ aryl, 4-10 membered heterocycloalkyl, and 5-10 membered heteroaryl, each of which may be optionally substituted by 1, 2, 3, or 4 independently selected $R^{1A}$ groups;

each $R^{1A}$ is independently selected from the group consisting of halo, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, $NR^{N1}R^{N2}$, $C_{3-10}$ cycloalkyl, $C_{6-10}$ aryl, 4-10 membered heterocycloalkyl, and 5-10 membered heteroaryl, wherein the $C_{1-6}$ alkyl, $C_{1-6}$ alkoxy, $C_{3-10}$ cycloalkyl, $C_{6-10}$ aryl, 4-10 membered heterocycloalkyl, and 5-10 membered heteroaryl are each optionally substituted by 1, 2, 3, or 4 independently selected $R^6$ groups;

$R^2$ is selected from the group consisting of $C_{1-6}$ alkyl, $C_{3-10}$ cycloalkyl, $C_{6-10}$ aryl, 4-10 membered heterocycloalkyl, and 5-10 membered heteroaryl, each of which may be optionally substituted by 1, 2, 3, or 4 independently selected $R^{2A}$ groups;

each $R^{2A}$ is independently selected from the group consisting of halo, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, $NR^{N1}R^{N2}$, $C_{3-10}$ cycloalkyl, $C_{6-10}$ aryl, 4-10 membered heterocycloalkyl, and 5-10 membered heteroaryl, wherein the $C_{1-6}$ alkyl, $C_{3-10}$ cycloalkyl, $C_{6-10}$ aryl, 4-10 membered heterocycloalkyl, and 5-10 membered heteroaryl are each optionally substituted by 1, 2, 3, or 4 independently selected $R^6$ groups;

$R^3$ is selected from the group consisting of H, $C_{1-6}$ alkyl, $C_{2-6}$ alkenyl, $C_{2-6}$ alkynyl, $C_{1-6}$ haloalkyl, $C_{1-6}$ alkoxy, and $C_{1-6}$ haloalkoxy;

$R^4$ and $R^5$ are each independently selected from the group consisting of H, halo, and $C_{1-6}$ alkoxy;

each $R^6$ is independently selected from the group consisting of OH, $NO_2$, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, and —($C_{1-6}$ alkoxy)-($C_{1-6}$ haloalkoxy);

each $R^{N1}$ is independently selected from the group consisting of H and $C_{1-6}$ alkyl;

each $R^{N2}$ is independently selected from the group consisting of $C_{2-6}$ alkyl, $C_{2-6}$ alkenyl, $C_{2-6}$ alkynyl, $C_{1-6}$ haloalkyl, $C_{1-6}$ alkoxy, and $C_{1-6}$ haloalkoxy; and m is 1 or 2; and ii) imaging the cell or tissue with an imaging technique.

2. The method of claim 1, wherein the imaging technique is selected from the group consisting of fluorescence imaging, positron emission tomography imaging, magnetic resonance imaging, single-photon emission computed tomography, positron emission tomography with computed tomography imaging, and positron emission tomography with magnetic resonance imaging.

3. The method of claim 1, wherein the imaging technique is selected from the group consisting of fluorescence imaging, position emission tomography imaging, and single-photon emission computed tomography.

4. The method of claim 1, wherein the compound is a Formula (Ia):

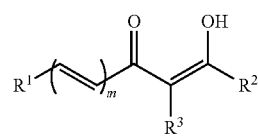

a pharmaceutically acceptable salt thereof, or a tautomer thereof.

5. The method of claim 1, wherein:

X is BR⁴R⁵;

$R^1$ is selected from the group consisting of $C_{6-10}$ aryl and 5-10 membered heteroaryl, each of which may be optionally substituted by 1, 2, 3, or 4 independently selected $R^{1A}$ groups;

each $R^{1A}$ is independently selected from the group consisting of halo, $C_{1-6}$ alkyl, $C_{1-6}$ haloalkyl, $C_{1-6}$ alkoxy, $C_{1-6}$ haloalkoxy, $NR^{N1}R^{N2}$, and $C_{6-10}$ aryl, wherein the $C_{1-6}$ alkyl, $C_{1-6}$ alkoxy, and $C_{6-10}$ aryl are each optionally substituted by 1, 2, 3, or 4 independently selected $R^6$ groups;

$R^2$ is selected from the group consisting of $C_{1-6}$ alkyl, $C_{3-6}$ cycloalkyl, and phenyl, each of which may be optionally substituted by 1, 2, 3, or 4 independently selected $R^{2A}$ groups;

$R^3$ is H;

$R^4$ and $R^5$ are each halo; and m is 1.

6. The method of claim 5, wherein:

$R^1$ is selected from the group consisting of phenyl and 5-6 membered heteroaryl, each of which may be optionally substituted by 1, 2, 3, or 4 independently selected $R^{1A}$ group;

$R^{1A}$ is independently selected from the group consisting of $C_{1-6}$ alkyl, $C_{1-6}$ alkoxy, $C_{1-6}$ haloalkoxy, $NR^{N1}R^{N2}$, and phenyl, wherein the $C_{1-6}$ alkyl, $C_{1-6}$ alkoxy, and phenyl are each optionally substituted by 1 or 2 independently selected $R^6$ groups; and $R^2$ is selected from the group consisting of $C_{1-6}$ alkyl, $C_{3-6}$ cycloalkyl, and phenyl.

7. The method of claim 6, wherein:

$R^1$ is selected from the group consisting of phenyl, imidazolyl, pyrazolyl, triazolyl, and pyridyl, each of which may be optionally substituted by 1 or 2 independently selected $R^{1A}$ groups;

each $R^{1A}$ is independently selected from the group consisting of $C_{1-6}$ alkyl, $C_{1-6}$ alkoxy, $C_{1-6}$ haloalkoxy, $NR^{N1}R^{N2}$, and phenyl, wherein the $C_{1-6}$ alkyl, $C_{1-6}$ alkoxy, and phenyl are each optionally substituted by 1 or 2 independently selected $R^6$ groups; and $R^2$ is selected from the group consisting of methyl, cyclobutyl, and phenyl.

8. The method of claim 1, wherein the compound of Formula I, a pharmaceutically acceptable salt thereof, or a tautomer thereof, comprises at least one radioisotope.

9. The method of claim 1, wherein the compound of Formula (I) is selected from the group consisting of:

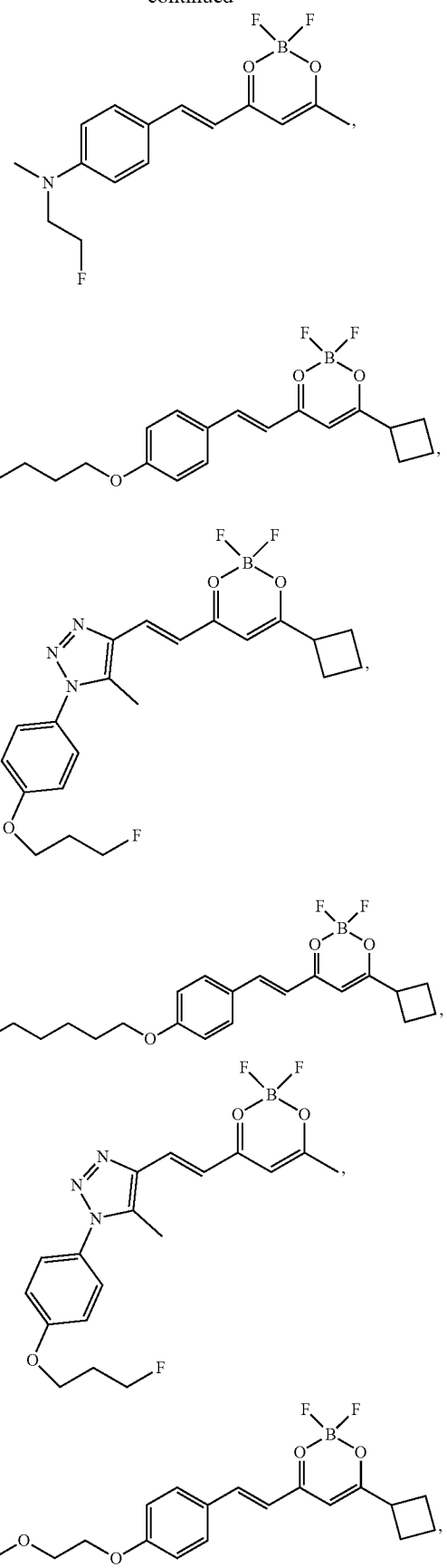

61
-continued
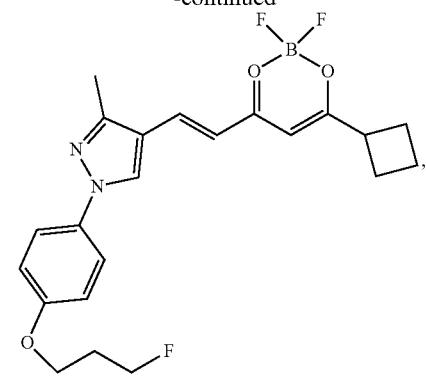
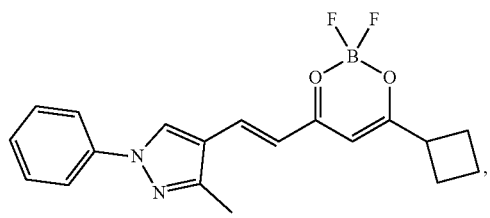
62
-continued
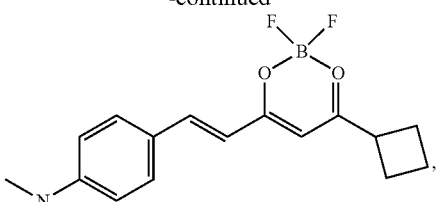
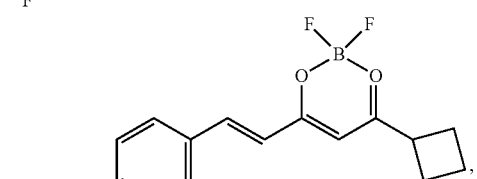
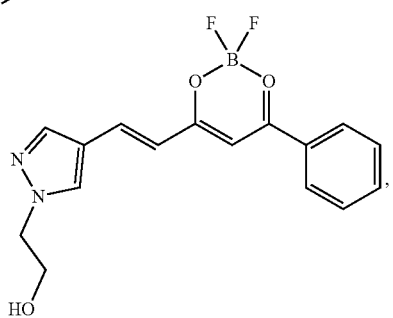
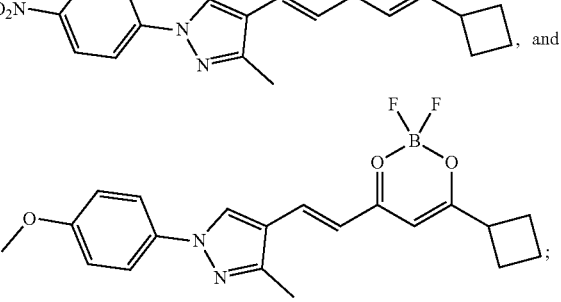
a pharmaceutically acceptable salt thereof, or a tautomer thereof.
10. The method of claim 8, wherein the compound of Formula (I) is selected from the group consisting of:
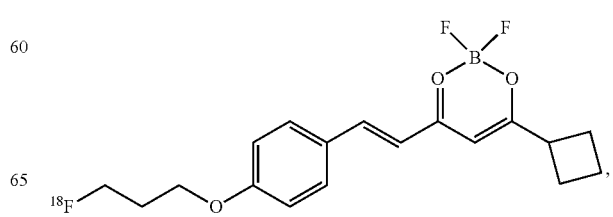

-continued
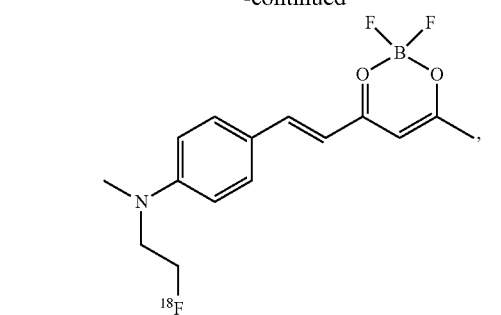
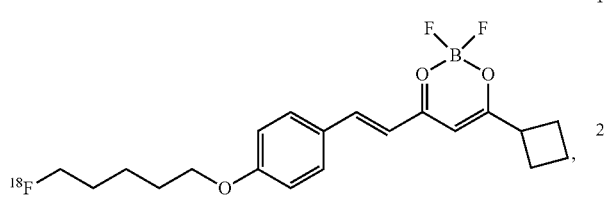
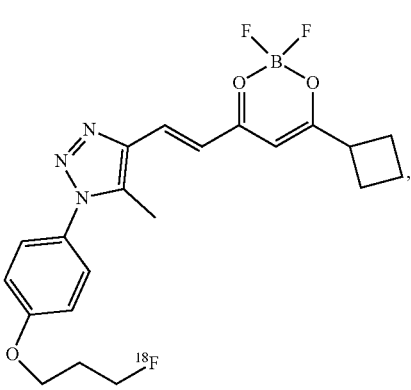
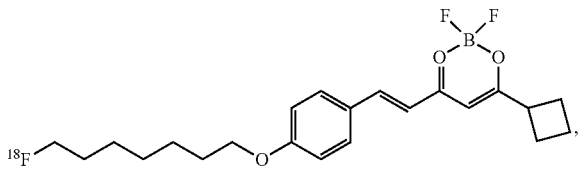
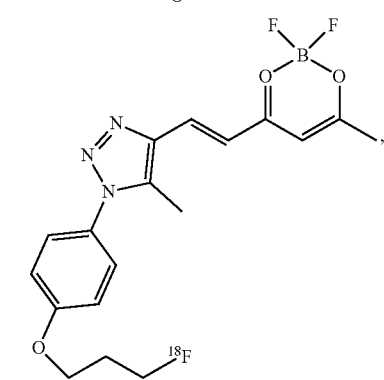
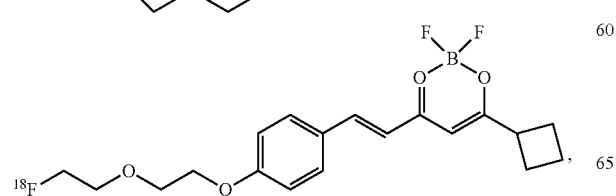
-continued
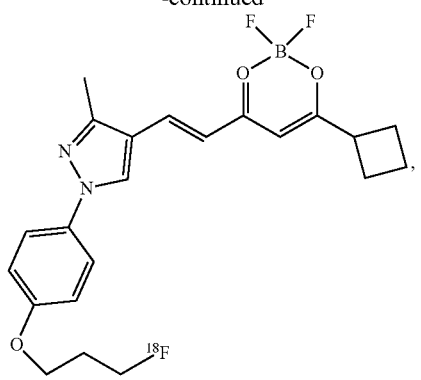
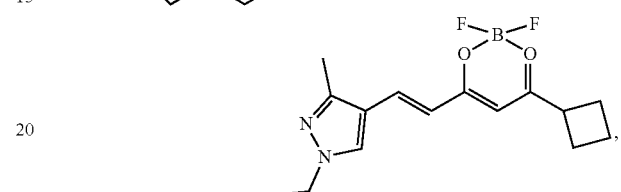
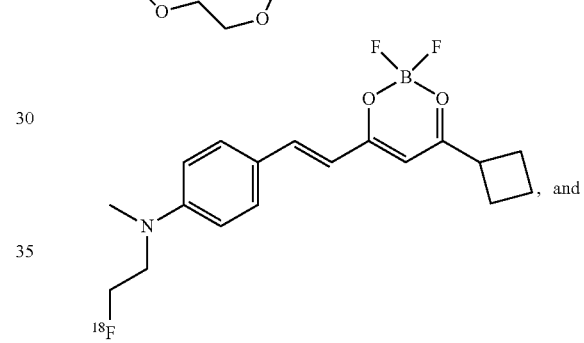
, and
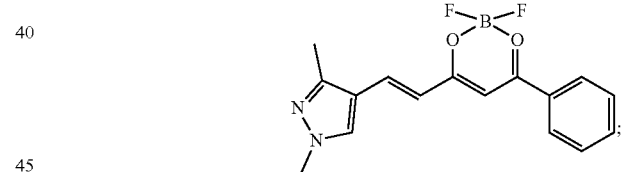
;
a pharmaceutically acceptable salt thereof, or a tautomer thereof.
11. A method of diagnosing a disease associated with amyloid beta, comprising:
i) administering to the subject a compound of Formula (I):
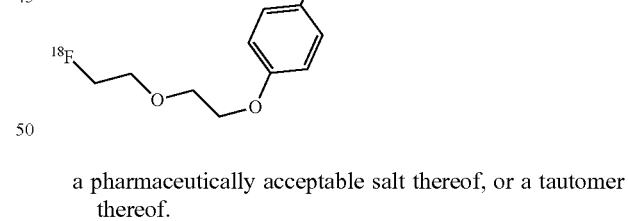
I a pharmaceutically acceptable salt thereof, or a tautomer thereof, wherein:

X is $BR^4R^5$;

$R^1$ is selected from the group consisting of $C_{3-10}$ cycloalkyl, $C_{6-10}$ aryl, 4-10 membered heterocycloalkyl, and 5-10 membered heteroaryl, each of which may be optionally substituted by 1, 2, 3, or 4 independently selected $R^{1A}$ groups;

each $R^{1A}$ is independently selected from the group consisting of halo, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, $NR^{N1}R^{N2}$, $C_{3-10}$ cycloalkyl, $C_{6-10}$ aryl, 4-10 membered heterocycloalkyl, and 5-10 membered heteroaryl, wherein the $C_{1-6}$ alkyl, $C_{1-6}$ alkoxy, $C_{3-10}$ cycloalkyl, $C_{6-10}$ aryl, 4-10 membered heterocycloalkyl, and 5-10 membered heteroaryl are each optionally substituted by 1, 2, 3, or 4 independently selected $R^6$ groups;

$R^2$ is selected from the group consisting of $C_{1-6}$ alkyl, $C_{3-10}$ cycloalkyl, $C_{6-10}$ aryl, 4-10 membered heterocycloalkyl, and 5-10 membered heteroaryl, each of which may be optionally substituted by 1, 2, 3, or 4 independently selected $R^{2A}$ groups;

each $R^{2A}$ is independently selected from the group consisting of halo, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, $NR^{N1}R^{N2}$, $C_{3-10}$ cycloalkyl, $C_{6-10}$ aryl, 4-10 membered heterocycloalkyl, and 5-10 membered heteroaryl, wherein the $C_{1-6}$ alkyl, $C_{3-10}$ cycloalkyl, $C_{6-10}$ aryl, 4-10 membered heterocycloalkyl, and 5-10 membered heteroaryl are each optionally substituted by 1, 2, 3, or 4 independently selected $R^6$ groups;

$R^3$ is selected from the group consisting of H, $C_{1-6}$ alkyl, $C_{2-6}$ alkenyl, $C_{2-6}$ alkynyl, $C_{1-6}$ haloalkyl, $C_{1-6}$ alkoxy, and $C_{1-6}$ haloalkoxy;

$R^4$ and $R^5$ are each independently selected from the group consisting of H, halo, and $C_{1-6}$ alkoxy;

each $R^6$ is independently selected from the group consisting of OH, $NO_2$, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, and —($C_{1-6}$ alkoxy)-($C_{1-6}$ haloalkoxy);

each $R^{N1}$ is independently selected from the group consisting of H and $C_{1-6}$ alkyl;

each $R^{N2}$ is independently selected from the group consisting of $C_{2-6}$ alkyl, $C_{2-6}$ alkenyl, $C_{2-6}$ alkynyl, $C_{1-6}$ haloalkyl, $C_{1-6}$ alkoxy, and $C_{1-6}$ haloalkoxy; and m is 1 or 2; and ii) imaging the cell or tissue with an imaging technique.

12. The method of claim 11, wherein the disease is associated with amyloid beta plaque formation, amyloid beta crosslinking, or copper-induced amyloid beta crosslinking.

13. The method of claim 11, wherein the disease is a disease of the central nervous system or a neurodegenerative disease.

14. The method of claim 11, wherein the disease is selected from the group consisting of Alzheimer's Disease, senile dementia of AD type (SDAT), Parkinson's disease, Lewis body dementia, vascular dementia, mild cognitive impairment (MCI), age-associated memory impairment (AAMI) and problems associated with ageing, post-encephalitic Parkinsonism, Amyotrophic lateral sclerosis (ALS), multiple sclerosis (MS) and Down syndrome.

15. The method of claim 11, wherein the disease is Alzheimer's Disease.

16. The method of claim 11, wherein the imaging technique is selected from the group consisting of fluorescence imaging, position emission tomography imaging, and single-photon emission computed tomography.

17. A method for treating a disease selected from the group consisting of senile dementia of AD type (SDAT), Parkinson's disease, Lewis body dementia, vascular dementia, mild cognitive impairment (MCI), age-associated memory impairment (AAMI) and problems associated with ageing, post-encephalitic Parkinsonism, Amyotrophic lateral sclerosis (ALS), multiple sclerosis, (MS) and Down syndrome in a subject, the method comprising administering to the subject a therapeutically effective amount of a compound of Formula (I):

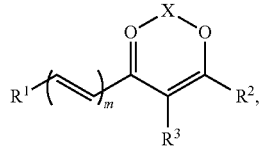

a pharmaceutically acceptable salt thereof, or a tautomer thereof, wherein:

X is $BR^4R^5$;

$R^1$ is selected from the group consisting of $C_{3-10}$ cycloalkyl, $C_{6-10}$ aryl, 4-10 membered heterocycloalkyl, and 5-10 membered heteroaryl, each of which may be optionally substituted by 1, 2, 3, or 4 independently selected $R^{1A}$ groups;

each $R^{1A}$ is independently selected from the group consisting of halo, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, $NR^{N1}R^{N2}$, $C_{3-10}$ cycloalkyl, $C_{6-10}$ aryl, 4-10 membered heterocycloalkyl, and 5-10 membered heteroaryl, wherein the $C_{1-6}$ alkyl, $C_{1-6}$ alkoxy, $C_{3-10}$ cycloalkyl, $C_{6-10}$ aryl, 4-10 membered heterocycloalkyl, and 5-10 membered heteroaryl are each optionally substituted by 1, 2, 3, or 4 independently selected $R^6$ groups;

$R^2$ is selected from the group consisting of $C_{1-6}$ alkyl, $C_{3-10}$ cycloalkyl, $C_{6-10}$ aryl, 4-10 membered heterocycloalkyl, and 5-10 membered heteroaryl, each of which may be optionally substituted by 1, 2, 3, or 4 independently selected $R^{2A}$ groups;

each $R^{2A}$ is independently selected from the group consisting of halo, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, $NR^{N1}R^{N2}$, $C_{3-10}$ cycloalkyl, $C_{6-10}$ aryl, 4-10 membered heterocycloalkyl, and 5-10 membered heteroaryl, wherein the $C_{1-6}$ alkyl, $C_{3-10}$ cycloalkyl, $C_{6-10}$ aryl, 4-10 membered heterocycloalkyl, and 5-10 membered heteroaryl are each optionally substituted by 1, 2, 3, or 4 independently selected $R^6$ groups;

$R^3$ is selected from the group consisting of H, $C_{1-6}$ alkyl, $C_{2-6}$ alkenyl, $C_{2-6}$ alkynyl, $C_{1-6}$ haloalkyl, $C_{1-6}$ alkoxy, and $C_{1-6}$ haloalkoxy;

$R^4$ and $R^5$ are each independently selected from the group consisting of H, halo, and $C_{1-6}$ alkoxy;

each $R^6$ is independently selected from the group consisting of OH, $NO_2$, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, and —($C_{1-6}$ alkoxy)-($C_{1-6}$ haloalkoxy);

each $R^{N1}$ is independently selected from the group consisting of H and $C_{1-6}$ alkyl;

each $R^{N2}$ is independently selected from the group consisting of $C_{2-6}$ alkyl, $C_{2-6}$ alkenyl, $C_{2-6}$ alkynyl, $C_{1-6}$ haloalkyl, $C_{1-6}$ alkoxy, and $C_{1-6}$ haloalkoxy; and m is 1 or 2.

18. The method of claim 17, wherein the disease is Alzheimer's Disease.
19. The method of claim 17, wherein the compound of Formula (I) is selected from the group consisting of:
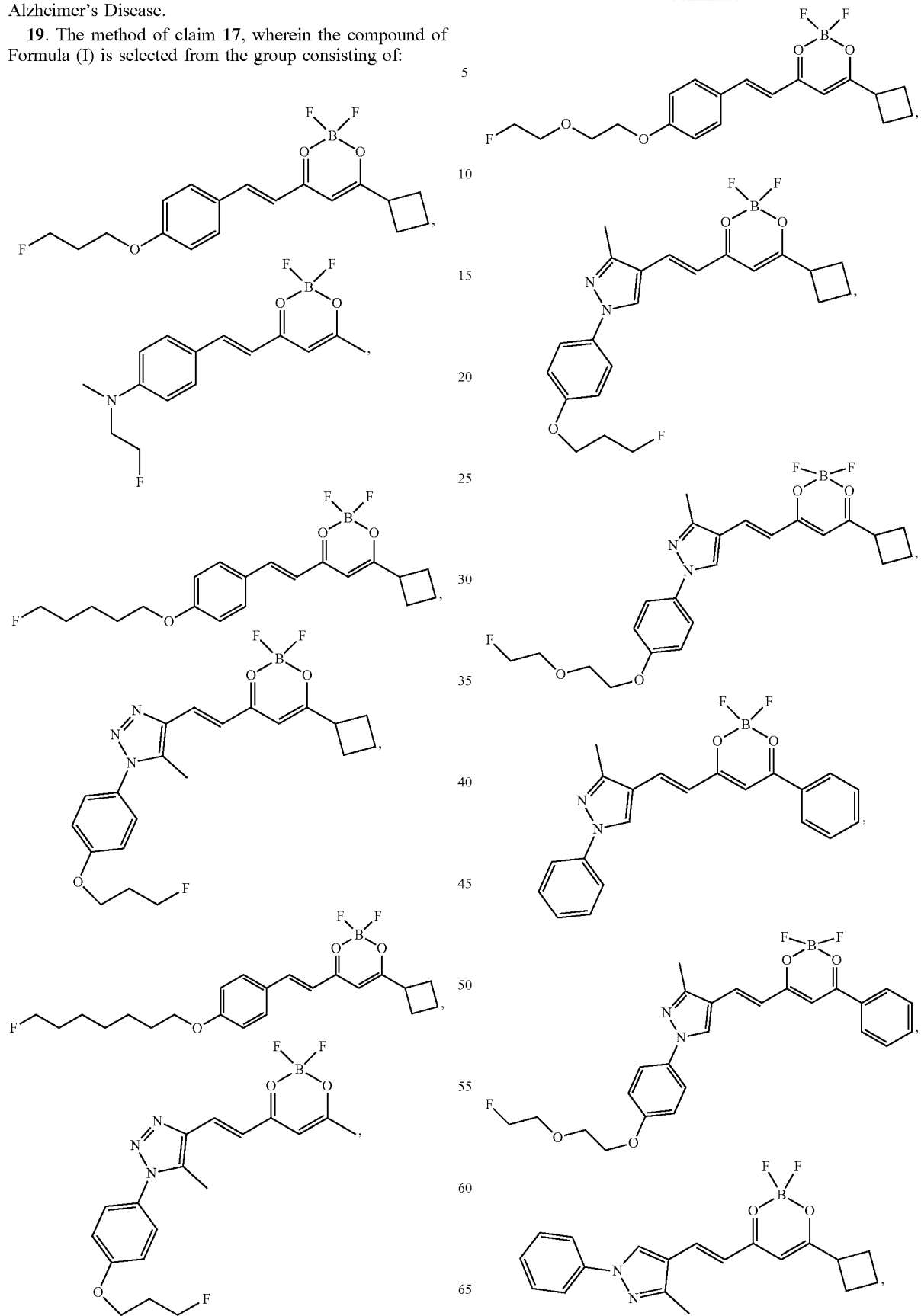

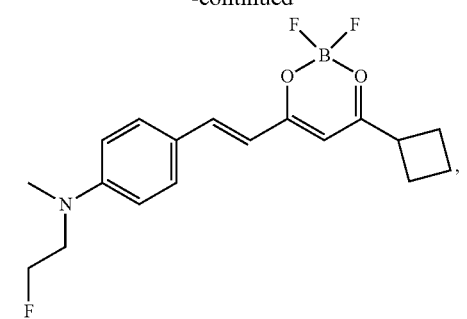
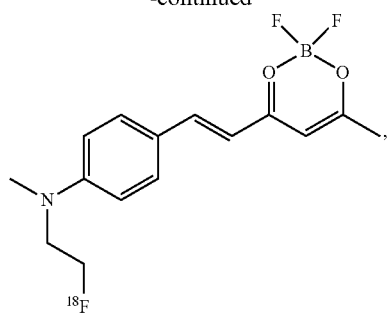
a pharmaceutically acceptable salt thereof, or a tautomer thereof.
20. The method of claim 17, wherein the compound of Formula (I) is selected from the group consisting of:

71
-continued
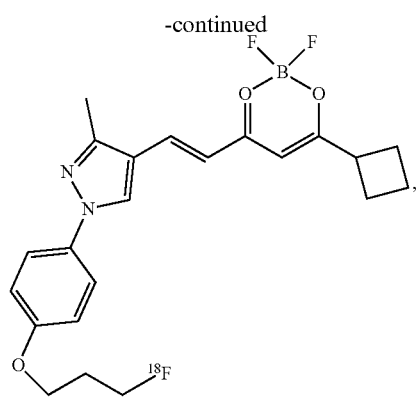
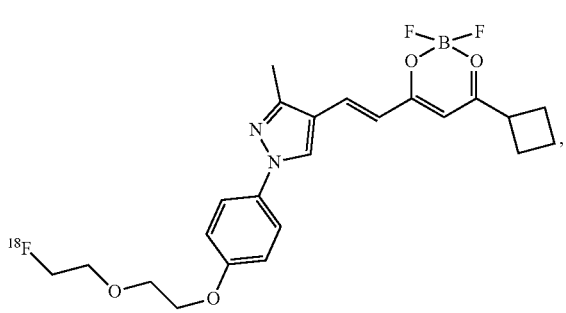
72
-continued
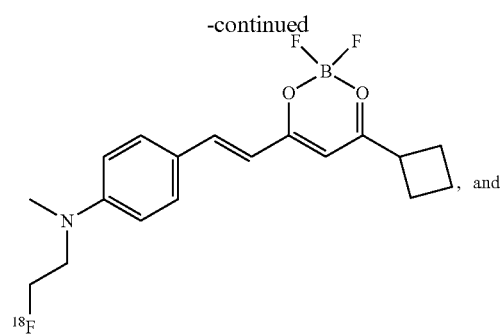
a pharmaceutically acceptable salt thereof, or a tautomer thereof.
* * * * *

UNITED STATES PATENT AND TRADEMARK OFFICE
CERTIFICATE OF CORRECTION

PATENT NO. : 12,102,695 B2  
APPLICATION NO. : 17/480924  
DATED : October 1, 2024  
INVENTOR(S) : Chongzhao Ran, Anna Moore and Jian Yang Page 1 of 1

It is certified that error appears in the above-identified patent and that said Letters Patent is hereby corrected as shown below:

In the Claims

In Column 57, Line 40, Claim 1, delete "Formula (I):" and insert -- Formula (I) or Formula (Ia): --

In Column 59, Line 45, Claim 7, delete "$NR^{N1} R^{N2}$," and insert -- $NR^{N1}R^{N2}$, --

In Column 67, Lines 53-65 (approx.), Claim 19, delete

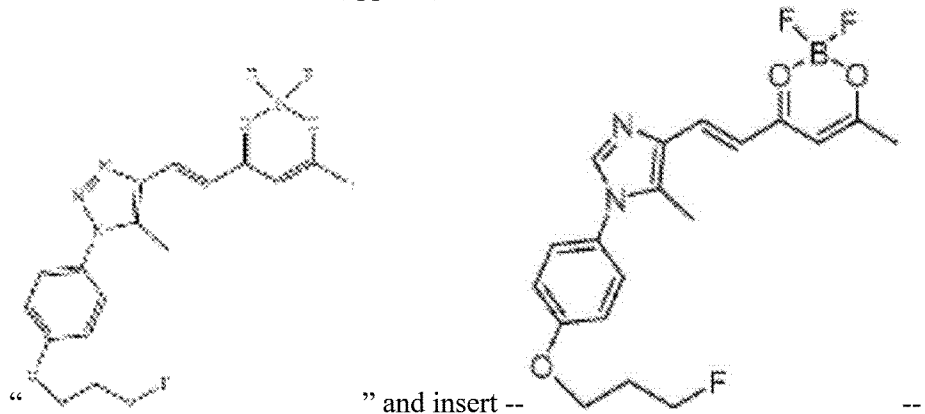

Signed and Sealed this  
Third Day of December, 2024

Katherine Kelly Vidal  
*Director of the United States Patent and Trademark Office*